(12) United States Patent
Crowell et al.

(10) Patent No.: US 12,084,686 B2
(45) Date of Patent: *Sep. 10, 2024

(54) ANTIBODIES WITH MODULATED GLYCAN PROFILES

(71) Applicant: Amgen Inc., Thousand Oaks, CA (US)

(72) Inventors: Christopher Kenyon Crowell, Thousand Oaks, CA (US); Jian Wu, Acton, MA (US); Neil Kitchen, Alberta (CA); Alison Jean Gillespie, Seattle, WA (US); Simina Crina Petrovan, Lynnwood, WA (US); Michael Charles Brandenstein, Woodinville, WA (US)

(73) Assignee: AMGEN INC., Thousand Oaks, CA (US)

( * ) Notice: Subject to any disclaimer, the term of this patent is extended or adjusted under 35 U.S.C. 154(b) by 877 days.

This patent is subject to a terminal disclaimer.

(21) Appl. No.: 17/051,528

(22) PCT Filed: Apr. 30, 2019

(86) PCT No.: PCT/US2019/029850
§ 371 (c)(1),
(2) Date: Oct. 29, 2020

(87) PCT Pub. No.: WO2019/213043
PCT Pub. Date: Nov. 7, 2019

(65) Prior Publication Data
US 2021/0062156 A1   Mar. 4, 2021

Related U.S. Application Data

(60) Provisional application No. 62/665,045, filed on May 1, 2018.

(51) Int. Cl.
| C12P 21/00 | (2006.01) |
| C07K 16/00 | (2006.01) |
| C07K 16/28 | (2006.01) |
| C12N 1/38  | (2006.01) |
| C12N 5/071 | (2010.01) |
| C12N 5/16  | (2006.01) |

(52) U.S. Cl.
CPC ........ *C12N 5/0682* (2013.01); *C07K 16/2875* (2013.01); *C07K 2317/14* (2013.01); *C07K 2317/92* (2013.01); *C12N 2500/34* (2013.01)

(58) Field of Classification Search
CPC ....... C12P 21/005; C12N 1/38; C12N 5/0037; C07K 16/00; C07K 2317/14
See application file for complete search history.

(56) References Cited

U.S. PATENT DOCUMENTS

| 4,499,064 A | 2/1985 | Shive |
| 4,695,623 A | 9/1987 | Stabinsky |
| 4,897,471 A | 1/1990 | Stabinsky |
| 4,968,607 A | 11/1990 | Dower |
| 5,075,222 A | 12/1991 | Hannum |
| 5,149,792 A | 9/1992 | Thomason |
| 5,272,064 A | 12/1993 | Thomason |
| 5,395,760 A | 3/1995 | Smith |
| 5,610,279 A | 3/1997 | Brockhaus |
| 5,767,064 A | 6/1998 | Sims |
| 5,856,296 A | 1/1999 | Mosley |
| 5,981,713 A | 11/1999 | Colotta |
| 6,015,938 A | 1/2000 | Boyle |
| 6,096,728 A | 8/2000 | Collins |
| 6,204,363 B1 | 3/2001 | Zsebo |
| 6,235,883 B1 | 5/2001 | Jakobovits |
| 6,271,349 B1 | 8/2001 | Dougall |
| 6,337,072 B1 | 1/2002 | Ford |
| 6,544,424 B1 | 4/2003 | Shevitz |
| 7,332,303 B2 | 2/2008 | Schilling |
| 8,354,105 B2 | 1/2013 | Wu |
| 9,822,388 B2 | 11/2017 | Wu |
| 10,655,156 B2 | 5/2020 | Gupta et al. |
| 10,894,972 B2 | 1/2021 | Huang et al. |
| 11,319,568 B2 | 5/2022 | Wu |
| 2004/0048368 A1 | 3/2004 | Chen |
| 2011/0086411 A1 | 4/2011 | Grillberger |
| 2016/0281124 A1 | 9/2016 | Pande et al. |
| 2020/0087698 A1 | 3/2020 | Wu et al. |

FOREIGN PATENT DOCUMENTS

| EP | 183350 A | 6/1986 |
| EP | 367566 A | 5/1990 |
| EP | 460846 A | 12/1991 |
| EP | 2248831 A1 | 11/2010 |
| JP | 06292592 A | 10/1994 |

(Continued)

OTHER PUBLICATIONS

Anonymous: "A Double-blind Study to Assess the Efficacy and Safety of Denosumab Produced by Two Different Processes in Postmenopausal Women With Osteoporosis—Full Text View—ClinicalTrials.gov", , Aug. 16, 2017 (Aug. 16, 2017), XP055607901, Retrieved from the Internet: URL:https://clinicaltrials.gov/ct2/show/NCT02157948 [retrieved on Jul. 23, 2019].

Feng Li et al: "Cell culture processes for monoclonal antibody production", MABS, vol. 2, No. 5, Sep. 1, 2010 (Sep. 1, 2010), pp. 466-479, XP055166177, ISSN: 1942-0862, DOI: 10.4161 /mabs.2.5.12720.

Flynn, et al., "Naturally occurring glycan forms of human immunoglobulins G1 and G2", Molecular Immunology 47 (2010) 2074-2082.

(Continued)

*Primary Examiner* — Maryam Monshipouri

(57) ABSTRACT

This invention relates to recombinantly-expressed denosumab molecules and methods for modulating glycan profiles of denosumab molecules.

10 Claims, 26 Drawing Sheets

Specification includes a Sequence Listing.

(56) References Cited

FOREIGN PATENT DOCUMENTS

| WO | 9305145 W | 3/1993 |
|---|---|---|
| WO | 1994010308 A1 | 5/1994 |
| WO | 1994028391 A1 | 12/1994 |
| WO | 9524484 W | 9/1995 |
| WO | 1997001633 A1 | 1/1997 |
| WO | 9845411 W | 10/1998 |
| WO | 1999028455 A1 | 6/1999 |
| WO | 2001036637 A1 | 5/2001 |
| WO | 2002101019 W | 12/2002 |
| WO | 03027248 W | 4/2003 |
| WO | 2004008100 A2 | 1/2004 |
| WO | 2006026445 A1 | 3/2006 |
| WO | 2006128908 W | 12/2006 |
| WO | 2012145682 A1 | 10/2012 |
| WO | 2012149197 A2 | 11/2012 |
| WO | 2013006479 A2 | 1/2013 |
| WO | 2013/181575 A2 | 12/2013 |
| WO | 2014/159259 A1 | 10/2014 |
| WO | 159259 * | 10/2014 |

OTHER PUBLICATIONS

Goetze, et al., "High-mannose glycans on the Fc region of therapeutic IgG antibodies increase serum clearance in humans" Glycobiology vol. 21 No. 7 pp. 949-959, 2011.

Ellen Gustafsson et al: "Evaluation of gene amplification for development of high producing biopharmaceutical cell lines", , Jan. 1, 2010 (Jan. 1, 2010), XP055607994, Retrieved from the Internet: URL:http://www.diva-portal.se/smash/get/diva2:356035/ FULL TEXT01.pdf.

Huang, et al., "A Robust Method for Increasing Fc Glycan High Mannose Level of Recombinant Antibodies" Biotechnology and Bioengineering, vol. 112, No. 6, Jun. 2015.

International Preliminary Report on Patentability & Written Opinion mailed Nov. 3, 2020 for PCT/US2019/029850.

International Search Report mailed Aug. 21, 2019 for PCT/US2019/029850.

Liming Liu: "Antibody Glycosylation and Its Impact on the Pharmacokinetics and Pharmacodynamics of Monoclonal Antibodies and Fc-Fusion Proteins", Journal of Pharmaceutical Sciences, vol. 104, No. 6, Jun. 1, 2015 (Jun. 1, 2015), pp. 1866-1884, XP055295176, us ISSN: 0022-3549, DOI: 10.1002/jps.24444.

Therapeutic Goods Administration: "Australian Public Assessment Report for Denosumab Proprietary Product Name: Prolia Sponsor: Amgen Australia Pty Ltd", , Jan. 1, 2011 (Jan. 1, 2011), XP055607935, Retrieved from the Internet: URL:https://www.tga.gov.au/sites/default/files/auspar-prolia.pdf [retrieved on Jul. 23, 2019].

Ahn et al., Effect of Culture Temperature on Erythropoietin Production and Glycosylation in a Perfusion Culture of Recombinant CHO Cells, Biotechnol. Bioeng (2008) 101:1234-1244.

Brasel et al. (1996), Blood 88:2004-2012.

Butler, "Animal cell cultures: recent achievements and perspectives in the production of biopharmaceuticals", Appl Microbiol Biotechnol., vol. 68 (3), pp. 283-291 (2005).

Carvalhal, et al., "Cell Growth Arrest by Nucleotides, Nucleosides and Bases as a Tool for Improved Production of Recombinant Proteins" Biotechnol. Frog, 19, 69-83, 2003.

Chen et al., "Temperature shift as a process optimization step for the production of pro-urokinase by a recombinant Chinese hamster ovary cell line in high-density perfusion culture", J Biosci Bioeng., vol. 97 (4), pp. 239-243 (2004).

Chu et al., "Industrial choices for protein production by large-scale cell culture," Curr Opin Biotechnol., vol. 12 (2), pp. 180-187 (2001).

Do et al., Mechanism of BLyS Action in B Cell Immunity, Cytokine Growth Factor Rev. (2002), 13:1; 19-25.

Efren et al., Effects of Cell Culture Conditions on Antibody N-Linked Glycosylation-What Effects High Mannose 5 Glycoform, Biotechnol. Bioeng (2011) 108(10):2348-2358.

Grammer et al., Modulation of Antibody Galactosylation Through Feeding of Uridine, Manganese Chloride, and Galactose, Biotechnol. Bioeng (2011) 108(7):1591-1602.

Håkansson, "Crystal structure of the trimeric α-helical coiled-coil and the three lectin domains of human lung surfactant protein D", Structure, vol. 7 (3), pp. 255-264 (1999).

Hansen and Emborg, "Extra- and intracellular amino acid concentrations in continuous Chinese hamster ovary cell culture" Appl Microbial Biotechnol, Jul. 1994;41(5):560-4.

Harbury et al., "A Switch Between Two-, Three-, and Four-Stranded Coiled Coils in GCN4 Leucine Zipper Mutants", Science, vol. 262 (5138), pp. 1401-1407 (1993).

Harbury et al., "Crystal structure of an isoleucine-zipper trimer", Nature, vol. 371 (6492), pp. 80-83 (1994).

Hayter et al., "Chinese hamster ovary cell growth and interferon production kinetics in stirred batch culture", Appl Microbiol Biotechnol., vol. 34 (5), pp. 559-564 (1991).

Hills et al., "Metabolic Control of Recombinant Monoclonal Antibody N-Glycosylation in GS-NSo Cells", Biotechnol Bioeng., vol. 75 (2), pp. 239-251 (2001).

Hubbard, "Synthesis and processing of asparagine-linked oligosaccharides", Annu Rev Biochem., vol. 50, pp. 555-583 (1981).

James et al., Glucose Starvation Alters Lipid-Linked Oligosaccharide Biosynthesis in Chinese Hamster Ovary Cells, The Journal of Biological Chemistry (1981) 256(12):6255-6261.

Jeng-Dar, Yang et al., "Achievement of high cell density and high antibody productivity by a controlled-fed perfusion bioreactor process," Biotech. and Bioeng. vol. 69, No. 1, pp. 74-82 (2000).

Kaufman et al., "Synthesis, Processing, and Secretion of Recombinant Human Factor VIII Expressed in Mammalian Cells", (1988), J. Biol Chem 263:6352-6362.

Kaufman, "Selection and coamplification of heterologous genes in mammalian cells", Methods Enzymol., vol. 185, pp. 537-566 (1990).

Kim et al., "CHO cells in biotechnology for production of recombinant proteins: current state and further potential", Appl Microbiol Biotechnol., vol. 93 (3), pp. 917-930 (2012).

Lipscomb et al., "Production of a Secreted Glycoprotein from an Inducible Promoter System in a Perfusion Bioreactor", Biotechnol Prog., vol. 20 (5), pp. 1402-1407 (2004).

Lloyd et al., "The role of the cell cycle in determining gene expression and productivity in CHO cells" Cytotechnology, 1999.

Lovejoy et al., "Crystal structure of a synthetic triple-stranded alpha-helical bundle", Science, vol. 259 (5099), pp. 1288-1293 (1993).

Maisonpierre et al., "Angiopoietin-2, a natural antagonist for Tie2 that disrupts in vivo angiogenesis", Science, vol. 277 (5322), pp. 55-60 (1997).

McKinnon et al., "Expression, purification and characterization of secreted recombinant human insulin-like growth factor-I (IGF-I) and the potent variant des(1-3) IGF-I in Chinese hamster ovary cells", (1991), J Mol Endocrinol 6:231-239.

Nahrgang, "Influence of cell-line and process conditions on the glycosylation of recombinant proteins", Infoscience EPFL Scientific Publications, 159 pages (2002).

NCBI Accession No. NM_00682.

Rodriguez et al., "High productivity of human recombinant beta-interferon from a low-temperature perfusion culture", J Biotechnol., vol. 150 (4), pp. 509-518 (2010).

Rüegg et al., "Sequence of a human transcript expressed in T-lymphocytes and encoding a fibrinogen-like protein", Gene, vol. 160 (2), pp. 257-262 (1995).

Sauer et al., "A High-Yielding, Generic Fed-Batch Cell Culture Process for Production of Recombinant Antibodies", Biotechnology and Bioengineering, vol. 67 (5), pp. 585-597 (2000).

Schmelzer et al., "Effects of osmoprotectant compounds on NCAM polysialylation under hyperosmotic stress and elevated pCO2," Biotechnology and Bioengineering, vol. 77 (4), pp. 359-368 (2002).

Schmelzer et al., "Hyperosmotic stress and elevated pCO2 alter monoclonal antibody charge distribution and monosaccharide content," Biotechnol Prog., vol. 18 (2), pp. 346-353 (2002).

Stanners et al., "Effect of extreme amino acid starvation on the protein synthetic machinery of CHO cells" J Cell Dhysiol, 1978.

(56) References Cited

OTHER PUBLICATIONS

Stettler et al., "New Disposable Tubes for Rapid and Precise Biomass Assessment for Suspension Cultures of Mammalian Cells", Biotechnol Bioeng, vol. 95 (6), pp. 1228-1233 (2006).
Sunley et al., "Strategies for the enhancement of recombinant protein production from mammalian cells by growth arrest", Biotechnol Adv., vol. 28 (3), pp. 385-394 (2010).
Torpier et al., "Synchronisation de cellules BHK 21 par carence partielle en L-Asparagine" Experimental Cell Research, 1974 (abstract in English).
Urlaub and Chasin, "Isolation of Chinese hamster cell mutants deficient in dihydrofolate reductase activity," Proc. Natl. Acad. Sci. USA, vol. 77 (7), pp. 4216-4220 (1980).
Voisard et al., "Potential of cell retention techniques for large-scale high-density perfusion culture of suspended mammalian cells", Biotechnol Bioeng., vol. 82 (7), pp. 751-765 (2003).
Whitford, et al., "Interest in Hollow-Fiber Perfusion Bioreactors is Growing" BioProcess International, 7(9), pp. 54-63, Oct. 2009.
Wong et al., Impact of Dynamic Online Fed-Batch Strategies on Metabolism, Productivity and N-Glycosylation Quality in CHO Cell Cultures, Biotechnol. & Bioeng., Wiley & Sons, NJ (2005) 89(2):164-177.
Wood et al., "High level synthesis of immunoglobulins in Chinese hamster ovary cells", (1990), J. Immunol. 145:3011-3016).
Yu et al., Production, Characterization and Pharmacokinetic Properties of Antibodies with N-Linked Mannose-5 Glycans, MAbs (2012), 4 :475-487.

\* cited by examiner

FIG. 3B

Relative Distributions of the N-glycans in Denosumab from CP2 and CP3 lots

| Sample Type | Lot No. | % A1F-G0[a] | % A2F-G0[b] | % A1-G0[c] | % A2F-G1[d] | % A2-G0[e] | % A2F-G2[f] | % Man5[g] | % A2-G1[h] | % Minor Species[i] | % Sialylated[j] |
|---|---|---|---|---|---|---|---|---|---|---|---|
| CP3 | 1 | 0.2 | 41.1 | 0.1 | 35.8 | 7.1 | 7.4 | 0.7 | 3.9 | 1.7 | 2.0 |
|  | 2 | 0.2 | 40.7 | 0.2 | 35.8 | 7.1 | 7.5 | 0.7 | 4.0 | 1.8 | 2.1 |
|  | 3 | 0.2 | 42.6 | 0.1 | 35.6 | 6.8 | 7.1 | 0.7 | 3.6 | 1.5 | 2.0 |
| CP2 | 1 | 2.0 | 61.0 | 1.6 | 16.2 | 5.6 | 1.4 | 8.4 | 0.8 | 2.0 | 1.0 |
|  | 2 | 1.7 | 61.8 | 1.4 | 16.6 | 5.5 | 1.5 | 7.6 | 0.7 | 1.9 | 1.2 |
|  | 3 | 1.6 | 62.3 | 1.3 | 16.8 | 5.5 | 1.4 | 7.5 | 0.7 | 1.9 | 0.8 |
| Reference Standard | ref | 2.1 | 58.8 | 1.8 | 17.6 | 5.7 | 1.6 | 8.6 | 0.9 | 1.9 | 1.1 | a A1FG-G0: asialo-, agalacto-, monoantennary, core-fucosylated
b 2F-G0: asialo-, agalacto, biantennary, core-fucosylated
c A1-G0: asialo-, agalacto-, monoantennary
d A2F-G1: asialo-, monogalacto-, biantennary, core fucosylated
e A2-G0: asialo-, agalacto-, biantennary
f A2F-G2: asialo-, bigalacto-, biantennary, core-fucosylated
g Man5: high mannose 5
h A2-G1: asialo-, monogalacto-, biantennary
i minor species: predominantly high mannose 6 and high mannose 7
j sialylated species: mono- and bi-sialylated structures with varying degrees of galactosylation and core fucose incorporation

| Sample Type | %Galactosylated | % Sialylated | % Man-5 | % Monoantennary |
|---|---|---|---|---|
| CP3 (Average) | 46.9 | 2.0 | 0.7 | 0.3 |
| CP2 (Average) | 18.7 | 1.0 | 7.8 | 3.2 |
| Reference Standard | 20.1 | 1.1 | 8.6 | 3.9 |

FIG. 6A

```
  M   E   F   G   L   S   W   L   F   L   V   A   I   L   K   G   V   Q   C
ATGGAGTTTGGGCTGAGCTGGCTTTTTCTTGTGGCTATTTTAAAAGGTGTCCAGTGT
  E   V   Q   L   L   E   S   G   G   G   L   V   Q   P   G   G   S   L   R
GAGGTGCAGCTGTTGGAGTCTGGGGGAGGCTTGGTACAGCCTGGGGGGTCCCTGAGA
  L   S   C   A   A   S   G   F   T   F   S   S   Y   A   M   S   W   V   R
CTCTCCTGTGCAGCCTCTGGATTCACCTTTAGCAGCTATGCCATGAGCTGGGTCCGC
  Q   A   P   G   K   G   L   E   W   V   S   G   I   T   G   S   G   G   S
CAGGCTCCAGGGAAGGGGCTGGAGTGGGTCTCAGGTATTACTGGGAGTGGTGGTAGT
  T   Y   Y   A   D   S   V   K   G   R   F   T   I   S   R   D   N   S   K
ACATACTACGCAGACTCCGTGAAGGGCCGGTTCACCATCTCCAGAGACAATTCCAAG
  N   T   L   Y   L   Q   M   N   S   L   R   A   E   D   T   A   V   Y   Y
AACACGCTGTATCTGCAAATGAACAGCCTGAGAGCCGAGGACACGGCCGTATATTAC
  C   A   K   D   P   G   T   T   V   I   M   S   W   F   D   P   W   G   Q
TGTGCGAAAGATCCAGGGACTACGGTGATTATGAGTTGGTTCGACCCCTGGGGCCAG
  G   T   L   V   T   V   S   S   A   S   T   K   G   P   S   V   F   P   L
GGAACCCTGGTCACCGTCTCCTCAGCCTCCACCAAGGGCCCATCGGTCTTCCCCCTG
  A   P   C   S   R   S   T   S   E   S   T   A   A   L   G   C   L   V   K
GCGCCCTGCTCCAGGAGCACCTCCGAGAGCACAGCGGCCCTGGGCTGCCTGGTCAAG
  D   Y   F   P   E   P   V   T   V   S   W   N   S   G   A   L   T   S   G
GACTACTTCCCCGAACCGGTGACGGTGTCGTGGAACTCAGGCGCTCTGACCAGCGGC
  V   H   T   F   P   A   V   L   Q   S   S   G   L   Y   S   L   S   S   V
GTGCACACCTTCCCAGCTGTCCTACAGTCCTCAGGACTCTACTCCCTCAGCAGCGTG
  V   T   V   P   S   S   N   F   G   T   Q   T   Y   T   C   N   V   D   H
GTGACCGTGCCCTCCAGCAACTTCGGCACCCAGACCTACACCTGCAACGTAGATCAC
  K   P   S   N   T   K   V   D   K   T   V   E   R   K   C   C   V   E   C
AAGCCCAGCAACACCAAGGTGGACAAGACAGTTGAGCGCAAATGTTGTGTCGAGTGC
```

FIG. 6A (Continued)

```
  P   P   C   P   A   P   P   V   A   G   P   S   V   F   L   F   P   P   K
CCACCGTGCCCAGCACCACCTGTGGCAGGACCGTCAGTCTTCCTCTTCCCCCCAAAA
  P   K   D   T   L   M   I   S   R   T   P   E   V   T   C   V   V   V   D
CCCAAGGACACCCTCATGATCTCCCGGACCCCTGAGGTCACGTGCGTGGTGGTGGAC
  V   S   H   E   D   P   E   V   Q   F   N   W   Y   V   D   G   V   E   V
GTGAGCCACGAAGACCCCGAGGTCCAGTTCAACTGGTACGTGGACGGCGTGGAGGTG
  H   N   A   K   T   K   P   R   E   E   Q   F   N   S   T   F   R   V   V
CATAATGCCAAGACAAAGCCACGGGAGGAGCAGTTCAACAGCACGTTCCGTGTGGTC
  S   V   L   T   V   V   H   Q   D   W   L   N   G   K   E   Y   K   C   K
AGCGTCCTCACCGTTGTGCACCAGGACTGGCTGAACGGCAAGGAGTACAAGTGCAAG
  V   S   N   K   G   L   P   A   P   I   E   K   T   I   S   K   T   K   G
GTCTCCAACAAAGGCCTCCCAGCCCCCATCGAGAAAACCATCTCCAAAACCAAAGGG
  Q   P   R   E   P   Q   V   Y   T   L   P   P   S   R   E   E   M   T   K
CAGCCCCGAGAACCACAGGTGTACACCCTGCCCCCATCCCGGGAGGAGATGACCAAG
  N   Q   V   S   L   T   C   L   V   K   G   F   Y   P   S   D   I   A   V
AACCAGGTCAGCCTGACCTGCCTGGTCAAAGGCTTCTACCCCAGCGACATCGCCGTG
  E   W   E   S   N   G   Q   P   E   N   N   Y   K   T   T   P   P   M   L
GAGTGGGAGAGCAATGGGCAGCCGGAGAACAACTACAAGACCACACCTCCCATGCTG
  D   S   D   G   S   F   F   L   Y   S   K   L   T   V   D   K   S   R   W
GACTCCGACGGCTCCTTCTTCCTCTACAGCAAGCTCACCGTGGACAAGAGCAGGTGG
  Q   Q   G   N   V   F   S   C   S   V   M   H   E   A   L   H   N   H   Y
CAGCAGGGGAACGTCTTCTCATGCTCCGTGATGCATGAGGCTCTGCACAACCACTAC
  T   Q   K   S   L   S   L   S   P   G   K
ACGCAGAAGAGCCTCTCCCTGTCTCCGGGTAAA
```

FIG. 6B

```
  M   E   T   P   A   Q   L   L   F   L   L   L   L   W   L   P   D   T   T
ATGGAAACCCCAGCGCAGCTTCTCTTCCTCCTGCTACTCTGGCTCCCAGATACCACC
  G   E   I   V   L   T   Q   S   P   G   T   L   S   L   S   P   G   E   R
GGAGAAATTGTGTTGACGCAGTCTCCAGGCACCCTGTCTTTGTCTCCAGGGGAAAGA
  A   T   L   S   C   R   A   S   Q   S   V   R   G   R   Y   L   A   W   Y
GCCACCCTCTCCTGTAGGGCCAGTCAGAGTGTTCGCGGCAGGTACTTAGCCTGGTAC
  Q   Q   K   P   G   Q   A   P   R   L   L   I   Y   G   A   S   S   R   A
CAGCAGAAACCTGGCCAGGCTCCCAGGCTCCTCATCTATGGTGCATCCAGCAGGGCC
  T   G   I   P   D   R   F   S   G   S   G   S   G   T   D   F   T   L   T
ACTGGCATCCCAGACAGGTTCAGTGGCAGTGGGTCTGGGACAGACTTCACTCTCACC
  I   S   R   L   E   P   E   D   F   A   V   F   Y   C   Q   Q   Y   G   S
ATCAGCAGACTGGAGCCTGAAGATTTTGCAGTGTTTTACTGTCAGCAGTATGGTAGT
  S   P   R   T   F   G   Q   G   T   K   V   E   I   K   R   T   V   A   A
TCACCTCGGACGTTCGGCCAAGGGACCAAGGTGGAAATCAAACGAACTGTGGCTGCA
  P   S   V   F   I   F   P   P   S   D   E   Q   L   K   S   G   T   A   S
CCATCTGTCTTCATCTTCCCGCCATCTGATGAGCAGTTGAAATCTGGAACTGCCTCT
  V   V   C   L   L   N   N   F   Y   P   R   E   A   K   V   Q   W   K   V
GTTGTGTGCCTGCTGAATAACTTCTATCCCAGAGAGGCCAAAGTACAGTGGAAGGTG
  D   N   A   L   Q   S   G   N   S   Q   E   S   V   T   E   Q   D   S   K
GATAACGCCCTCCAATCGGGTAACTCCCAGGAGAGTGTCACAGAGCAGGACAGCAAG
  D   S   T   Y   S   L   S   S   T   L   T   L   S   K   A   D   Y   E   K
GACAGCACCTACAGCCTCAGCAGCACCCTGACGCTGAGCAAAGCAGACTACGAGAAA
  H   K   V   Y   A   C   E   V   T   H   Q   G   L   S   S   P   V   T   K
CACAAAGTCTACGCCTGCGAAGTCACCCATCAGGGCCTGAGCTCGCCCGTCACAAAG
  S   F   N   R   G   E   C
AGCTTCAACAGGGGAGAGTGT
```

HILIC M5

FIG. 12
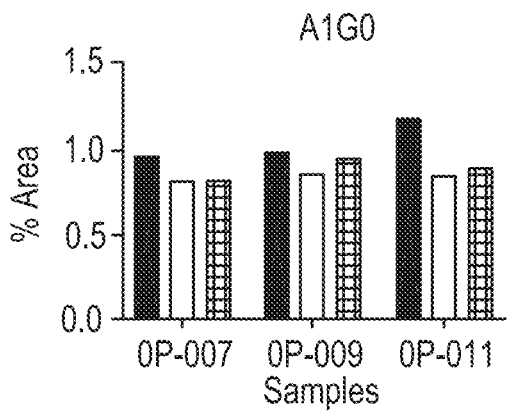
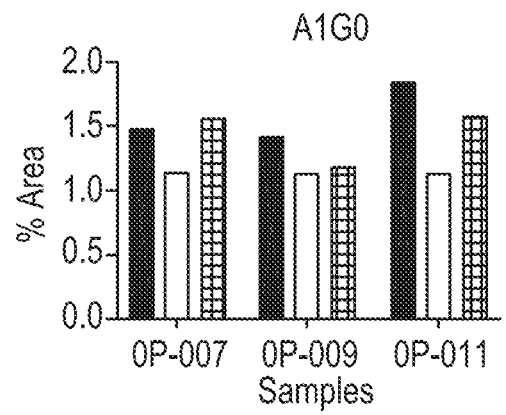
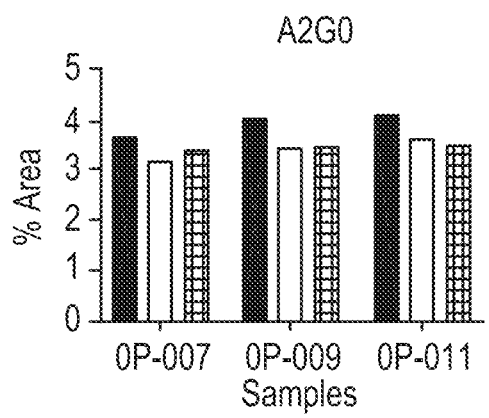
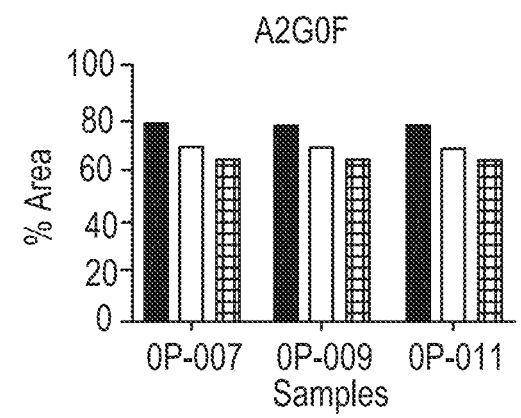
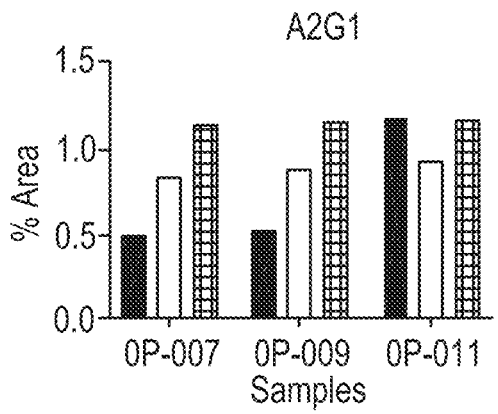
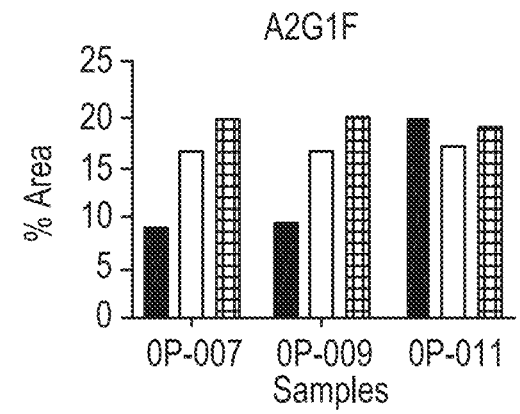

FIG.13

| Process Steps | CP2 Process (2,000 L) | CP3 Process (2,000 L) | Differences |
|---|---|---|---|
| Cell Thaw | WCB Vial Thaw 70S cell line | WCB Vial Thaw 25B12 cell line | Different cell lines. CP2: 70S (AM1-D parent. Does not contain MTX) CP3: 25B12 (CS-9 parent. Contains 2 µM MTX) |
| Culture Expansion | Shake Flasks, 12 - 13 days | Shake Flasks, 18 - 21 days | Culture Medium. CP3 contains MTX |
| Seed bioreactor (N-4) | | 10 L Culture Bag Bioreactor, 3 days | No culture bag stage in CP2. CP3 medium contains MTX |
| Seed bioreactor (N-3) | 20 L Bioreactor, 3 days | 50 L Bioreactor, 3 days | Culture medium |
| Seed bioreactor (N-2) | 60 L Bioreactor, 3 days | 100 L Bioreactor, 3 days | Culture medium |
| Seed bioreactor (N-1) | 300 L Bioreactor, 3-4 days | 500 L Bioreactor, 3 days | Culture medium |
| Production Bioreactor | 2,000 L Bioreactor, 13-14 days d3, d9 bolus feeds | 2,000 L Bioreactor, 10 days d4, d7, d9 bolus feeds | Seed VCD, pH and dissolved oxygen control. Media recipes and number of feeds. CP3 process contains yeast extract and betaine. Duration |
| In-Process Pool | Harvest Broth | Harvest Broth | |

FIG. 15

| Process Steps | CP2 Process (16,000 L) | CP4 Process (2,000 L) | Differences |
|---|---|---|---|
| Cell thaw | WCB vial thaw<br>CHO cell line | WCB vial thaw<br>CHO cell line | Cell lines:<br>CP2: AM-1/D parent (not MTX amplified)<br>CP4: CS-9 parent (MTX) |
| Culture expansion | Shake flasks,<br>12 to 13 days | Shake flasks,<br>12 to 14 days | Medium formulation:<br>CP4 contains MTX |
| Expansion bioreactors (N-4, N-3) | N-4: 20 L bioreactor, 3 days<br>N-3: 100 L bioreactor, 3 days | 50 L 2-stage culture bag bioreactor<br>Stage 1 (N-4): 3 days<br>Stage 2 (N-3): 3 days | No culture bag stage in CP2<br>Medium formulation: CP4 contains MTX |
| Expansion bioreactors (N-2, N-1) | N-2: 500 L bioreactor, 3 days<br>N-1: 2.5 kL bioreactor, 3-4 days | 500 L 2-stage SUB<br>Stage 1 (N-2): 3 days<br>Stage 2 (N-1): 4 days | Medium formulation:<br>CP4 N-1 stage fed on day 2 |
| Production bioreactor | 16 kL bioreactor, 14 days<br>Bolus feeds on days 3 and 9<br>Fed-batch mode | 2 kL bioreactor, 18 days<br>Bolus feeds on days 3 and 6<br>Perfusion mode started day 7<br>Perfusion media change day 11 | Production mode<br>Process set points<br>CP4 uses chemically defined media formulations |
| Harvest | Separation by disc stack centrifugation | Separation by flocculation, using PDADMAC* and PEG*, and settling | Separation method |

ANTIBODIES WITH MODULATED GLYCAN PROFILES

RELATED APPLICATIONS

This application is the U.S. National Phase of International Application No. PCT/US2019/029850, filed Apr. 30, 2019 and published in English, which claims the benefit under 35 U.S.C. § 119(e) to U.S. Provisional Application No. 62/665,045, filed May 1, 2018 which is incorporated herein by reference in its entirety.

SEQUENCE LISTING

The instant application contains a sequence listing which has been submitted electronically in ASCII format and is hereby incorporated by reference in its entirety. Said ASCII copy, created on Oct. 28, 2020, is named a-2256-us-pct_st25.txt and is 15,116 bytes in size.

FIELD OF THE INVENTION

This invention relates to recombinantly-expressed antibodies and methods for modulating glycan profiles of such antibodies.

BACKGROUND OF THE INVENTION

The structure and composition of the glycan moieties of a glycoprotein can affect the safety and efficacy of therapeutic proteins, including its immunogenicity, solubility and half-life. Proteins produced in mammalian cell cultures may contain varied levels of high-mannose glycoforms such as Mannose5 (Man-5), Mannose6 (Man-6), Mannose7 (Man-7), Mannose8 (Man-8) and Mannose9 (Man-9). Antibodies with high-mannose content have become of interest because of the differences in therapeutic activities and clearance rates exhibited by antibodies bearing Man-5 glycans and Man-7, 8 or 9 glycans. For example, high mannose antibodies that were generated with kifunensine treatment showed higher ADCC activity and greater affinity to FCγRIIIA (Zhou et al., (2008), Biotechnol Bioeng 99(3):652-665). Similarly, Yu et al. report that Man-5 and Man-8/9 glycoforms appeared to have increased ADCC activity, decreased CDC activity, increased binding affinity to FcγRIIIA, and decreased binding affinity to FcγRIIA and IIB (Yu et al., MAbs. 2012 Jul. 1; 4(4): 475-487. doi:10.4161/mabs.20737). Therefore, antibody composition with increased high-mannose glycans (such as Man-5) can offer certain therapeutic benefits.

On the other hand, it has also been reported that Man-5 and Man-6 glycoforms also exhibit more rapid clearance rate than the complex-fucosylated glycoform (Yu et al., supra). Therefore, high levels of Man-5 glycans could lead to decreased half-life and rapid clearance of an antibody. Accordingly, there is a need to control and modulate high-mannose content of an antibody, to achieve a desired balance between PK properties and therapeutic activities (such as ADCC).

SUMMARY OF THE INVENTION

As disclosed and exemplified herein, a method for modulating the level of high-mannose glycan on denosumab has been developed. In particular, by reducing the amount of glucose and increasing the amount of galactose in culture medium during production phase, the level of high-mannose glycan was increased. Also disclosed and exemplified herein are recombinantly-produced denosumab comprising various glycan profiles.

Based on the disclosure provided herein, those skilled in the art will recognize, or be able to ascertain using no more than routine experimentation, many equivalents to the specific embodiments of the invention described herein. Such equivalents are intended to be encompassed by the following embodiments (E).

E1. A method of increasing the level of high-mannose present on denosumab molecules, wherein said denosumab molecules are recombinantly-expressed by a mammalian host cell, comprising:
(a) incubating said mammalian host cell in a first culture medium during growth phase until the cell density is at least $1 \times 10^6$ viable cells/mL, wherein said first culture medium comprises from about 1 g/L to about 20 g/L glucose; and subsequently
(b) incubating host cells from step (a) in a second culture medium during production phase to express said denosumab molecules, wherein said second culture medium comprises from about 0 g/L to about 10 g/L glucose and from about 5 g/L to about 20 g/L galactose;
wherein from about 2% to about 14% of the denosumab molecules comprise high-mannose glycan at N-298 site.

E2. A method of increasing the level of high-mannose present on denosumab molecules, wherein said denosumab molecules are recombinantly-expressed by a mammalian host cell, comprising:
(a) incubating said mammalian host cell in a first culture medium during growth phase until the cell density is at least $1 \times 10^6$ viable cells/mL, wherein said first culture medium comprises from about 1 g/L to about 20 g/L glucose; and subsequently
(b) incubating host cells from step (a) in a second culture medium during production phase to express said denosumab molecules, wherein said second culture medium comprises from about 0 g/L to about 10 g/L glucose and from about 5 g/L to about 20 g/L galactose;
wherein the percentage of denosumab molecules comprising high-mannose at N-298 site is increased, as compared to a control.

E3. The method of E2, wherein from about 2% to about 14% of the denosumab molecules comprise high-mannose glycan at N-298 site.

E4. The method of any one of E1-E3, wherein during the growth phase, the glucose concentration is maintained at from about 1 g/L to about 20 g/L by bolus feed or perfusion.

E5. The method of any one of E1-E3, wherein during the growth phase, the glucose concentration is maintained at from about 4 g/L to about 20 g/L by bolus feed or perfusion.

E6. The method of any one of E1-E5, wherein during the production phase, the host cells are initially maintained in the first culture medium for about 3 to about 15 days, and subsequently transitioned into the second culture medium by perfusion or bolus feed.

E7. The method of any one of E1-E6, wherein when the host cells are incubated in the second culture medium during the production phase, the glucose concentration is maintained at from about 0 g/L to about 10 g/L, or from about 0 g/L to about 8 g/L, by bolus feed or perfusion.

E8. The method of any one of E1-E7, wherein when the host cells are incubated in the second culture medium during the production phase, the galactose concentration is maintained at from about 5 g/L to about 20 g/L, or from about 7 g/L to about 15 g/L, by bolus feed or perfusion.

E9. The method of any one of E1-E8, wherein when the host cells are incubated in the second culture medium during the production phase, the glucose concentration is maintained at from about 0 g/L to about 10 g/L, and the galactose concentration is maintained at from about 5 g/L to about 20 g/L, by bolus feed or perfusion.

E10. The method of any one of E1-E9, wherein when the host cells are incubated in the second culture medium during the production phase, the glucose concentration is maintained at from about 0 g/L to about 8 g/L, and the galactose concentration is maintained at from about 7 g/L to about 15 g/L, by bolus feed or perfusion.

E11. The method of any one of E1-E10, comprising:
(a) incubating said mammalian host cell in a first culture medium during growth phase, and supplementing the culture with one or more bolus feeds, wherein the glucose concentration is maintained at from about 1 g/L to about 20 g/L during the growth phase;
(b) transitioning host cells from step (a) from growth phase to production phase, and maintaining the glucose concentration at from about 1 g/L to about 20 g/L for about 3 days to about 15 days; and subsequently
(c) transitioning the host cells of (b) into a second culture medium, wherein said second culture medium comprises from about 0 g/L to about 10 g/L glucose and from about 5 g/L to about 20 g/L galactose.

E12. The method of E11, wherein in steps (a) and (b), the glucose concentration is maintained at from about 1 g/L to about 20 g/L by bolus feed or perfusion.

E13. The method of E11 or E12, wherein in steps (a) and (b), the glucose concentration is maintained at from about 4 g/L to about 20 g/L by bolus feed or perfusion.

E14. The method of any one of E11-E13, wherein in step (c), the glucose concentration is maintained at from about 0 g/L to about 10 g/L, or from about 0 g/L to about 8 g/L, by bolus feed or perfusion.

E15. The method of any one of E11-E14, wherein in step (c), the galactose concentration is maintained at from about 5 g/L to about 20 g/L, or from about 7 g/L to about 15 g/L, by bolus feed or perfusion.

E16. The method of any one of E11-E15, wherein in step (c), the glucose concentration is maintained at from about 0 g/L to about 8 g/L, and the galactose concentration is maintained at from about 7 g/L to about 15 g/L, by bolus feed or perfusion.

E17. The method of any one of E1-E16, wherein said first and second culture media are chemically-defined culture media.

E18. The method of any one of E1-E17, wherein said first culture medium comprises from about 4 g/L to about 18 g/L glucose.

E19. The method of any one of E1-E18, wherein said second culture medium comprises from about 1 g/L to about 8 g/L, from about 1 g/L to about 7 g/L, from about 1 g/L to about 6 g/L, from about 1 g/L to about 5/L glucose.

E20. The method of any one of E1-E19, wherein said second culture medium comprises from about 1 g/L to about 5/L glucose.

E21. The method of any one of E1-E20, wherein said second culture medium comprises from about 8 g/L to about 14 g/L, from about 9 g/L to about 13 g/L, or from about 10 g/L to about 12 g/L galactose.

E22. The method of any one of E1-E21, wherein said second culture medium comprises from about 10 g/mL to about 12 g/mL galactose.

E23. The method of any one of E1-E21, wherein said second culture medium comprises from about 1 g/L to about 5/L glucose, and from about 10 g/mL to about 12 g/mL galactose.

E24. The method of any one of E1-E23, wherein in step (a), said cell density is at least about $2\times10^6$ viable cells/mL, at least about $5\times10^6$ viable cells/mL, or at least about $10\times10^6$ viable cells/mL.

E25. The method of any one of E1-E24, wherein from about 4% to about 11% of the denosumab molecules comprise high-mannose at the N-298 site.

E25b. The method of any one of E1-E24, wherein from about 4% to about 14% of the denosumab molecules comprise high-mannose at the N-298 site.

E25c. The method of any one of E1-E24, wherein from about 5% to about 14% of the denosumab molecules comprise high-mannose at the N-298 site.

E25d. The method of any one of E1-E24, wherein from about 5% to about 11% of the denosumab molecules comprise high-mannose at the N-298 site.

E26. The method of any one of E1-E25, wherein from 2% to 6.5%, or from 8.5% to 14%, of the denosumab molecules comprise high-mannose at the N-298 site.

E27. The method of any one of E1-E26, wherein from 4% to 6.5%, or from 8.5% to 11%, of the denosumab molecules comprise high-mannose at the N-298 site.

E27b. The method of any one of E1-E25, wherein from 4% to 6.5%, or from 8.5% to 14%, of the denosumab molecules comprise high-mannose at the N-298 site.

E27c. The method of any one of E1-E25, wherein from 5% to 6.5%, or from 8.5% to 14%, of the denosumab molecules comprise high-mannose at the N-298 site.

E27d. The method of any one of E1-E25, wherein from 5% to 6.5%, or from 8.5% to 11%, of the denosumab molecules comprise high-mannose at the N-298 site.

E28. The method of any one of E1-E27, with the proviso that the percentage of the denosumab molecules comprising high-mannose at the N-298 site is not from 6.5% to 7.5%.

E29. The method of any one of E1-E27, with the proviso that the percentage of the denosumab molecules comprising high-mannose at the N-298 site is not from 6.5% to 8.5%.

E30. The method of any one of E1-E27, with the proviso that the percentage of the denosumab molecules comprising high-mannose at the N-298 site is not from 7.5% to 8.5%.

E31. The method of any one of E1-E30, wherein said host cells are transitioned from the first culture medium into the second culture medium by perfusion.

E32. The method of any one of E1-E30, wherein said host cells are transitioned from the first culture medium into the second culture medium by bolus feed.

E33. A method of increasing the level of high-mannose present on denosumab molecules, wherein said denosumab molecules are recombinantly-expressed by a mammalian host cell, comprising:

(a) establishing an initial cell culture, wherein the density of said mammalian host cells is at least $1 \times 10^6$ viable cells/mL; and subsequently (b) incubating host cells from step (a) in a culture medium during production phase to express said denosumab molecules, wherein said culture medium comprises from about 0 g/L to about 10 g/L glucose and from about 5 g/L to about 20 g/L galactose;

wherein from about 2% to about 14% of the denosumab molecules comprise high-mannose glycan at N-298 site.

E34. A method of increasing the level of high-mannose present on denosumab molecules, wherein said denosumab molecules are recombinantly-expressed by a mammalian host cell, comprising:

(a) establishing an initial cell culture, wherein the density of said mammalian host cells is at least $1 \times 10^6$ viable cells/mL; and subsequently (b) incubating host cells from step (a) in a culture medium during production phase to express said denosumab molecules, wherein said culture medium comprises from about 0 g/L to about 10 g/L glucose and from about 5 g/L to about 20 g/L galactose;

wherein the percentage of denosumab molecules comprising high-mannose at N-298 site is increased, as compared to a control.

E35. The method of E34, wherein from about 2% to about 14% of the denosumab molecules comprise high-mannose glycan at N-298 site.

E36. The method of any one of E33-E35, wherein in step (b), the glucose concentration is maintained at from about 0 g/L to about 10 g/L by bolus feed or perfusion.

E37. The method of any one of E33-E36, wherein in step (b), the galactose concentration is maintained at from about 5 g/L to about 20 g/L by bolus feed or perfusion.

E38. The method of any one of E33-E37, wherein said culture medium is a chemically-defined culture medium.

E39. The method of any one of E33-E38, wherein said culture medium comprises from 1 g/L to about 8 g/L, from about 1 g/L to about 7 g/L, from about 1 g/L to about 6 g/L, from about 1 g/L to about 5/L glucose.

E40. The method of any one of E33-E39, wherein said culture medium comprises from about 1 g/L to about 5/L glucose.

E41. The method of any one of E33-E40, wherein said culture medium comprises from about from about 8 g/L to about 14 g/L, from about 9 g/L to about 13 g/L, or from about 10 g/L to about 12 g/L galactose.

E42. The method of any one of E33-E41, wherein said second culture medium comprises from about 10 g/mL to about 12 g/mL galactose.

E43. The method of any one of E33-E42, wherein in step (a), said cell density is at least about $2 \times 10^6$ viable cells/mL, at least about $5 \times 10^6$ viable cells/mL, or at least about $10 \times 10^6$ viable cells/mL.

E44. The method of any one of E33-E43, wherein from about 4% to about 11% of the denosumab molecules comprise high-mannose at the N-298 site.

E44b. The method of any one of E33-E43, wherein from about 4% to about 14% of the denosumab molecules comprise high-mannose at the N-298 site.

E44c. The method of any one of E33-E43, wherein from about 5% to about 14% of the denosumab molecules comprise high-mannose at the N-298 site.

E44d. The method of any one of E33-E43, wherein from about 5% to about 11% of the denosumab molecules comprise high-mannose at the N-298 site.

E45. The method of any one of E33-E44, wherein from 2% to 6.5%, or from 8.5% to 14%, of the denosumab molecules comprise high-mannose at the N-298 site.

E46. The method of any one of E33-E45, wherein from 4% to 6.5%, or from 8.5% to 11%, of the denosumab molecules comprise high-mannose at the N-298 site.

E46b. The method of any one of E33-E45, wherein from 4% to 6.5%, or from 8.5% to 14%, of the denosumab molecules comprise high-mannose at the N-298 site.

E46c. The method of any one of E33-E45, wherein from 5% to 6.5%, or from 8.5% to 14%, of the denosumab molecules comprise high-mannose at the N-298 site.

E46d. The method of any one of E33-E45, wherein from 5% to 6.5%, or from 8.5% to 11%, of the denosumab molecules comprise high-mannose at the N-298 site.

E47. The method of any one of E33-E46, with the proviso that the percentage of the denosumab molecules comprising high-mannose at the N-298 site is not between 6.5% to 7.5%.

E48. The method of any one of E33-E46, with the proviso that the percentage of the denosumab molecules comprising high-mannose at the N-298 site is not between 6.5% to 8.5%.

E49. The method of any one of E33-E46, with the proviso that the percentage of the denosumab molecules comprising high-mannose at the N-298 site is not between 7.5% to 8.5%.

E50. The method of any one of E1-E49, wherein said culture produces at least about 10 g/L of denosumab at harvesting.

E51. The method of E1 or E33, wherein the percentage of denosumab molecules comprising high-mannose at the N-298 site is increased, as compared to a control.

E52. The method of any one of E2-E32 and E34-E51, wherein said control is the percentage of high-mannose at the N-298 site from a reference batch, when said reference batch is produced in a culture medium that comprises from about 5 g/L to about 15 g/L glucose, and does not comprises galactose.

E53. The method of any one of E2-E32 and E34-E52, wherein said control is about 1.5% or less of the denosumab molecules comprise high-mannose at the N-298 site.

E54. The method of any one of E1-E53, wherein said mammalian host cell is a CHO cell.

E55. The method of E54, wherein said CHO cell is a CS-9, CHO-K1, CHO-DG44, or CHO-S cell.

E56. The method of E54, wherein said CHO cell is a CS-9 cell.

E57. The method of E54, wherein said CHO cell is an AM1/D cell.

E57b. The method of E54, wherein said CHO cell is a CHO DUX-B11 cell.

E57c. The method of E54, wherein said CHO cell is a CHO GS knock-out cell.

E57d. The method of E54, wherein said CHO cell is a CHO-K1 cell.

E58. The method of any one of E54-E57, wherein said CHO cell has been amplified by methotrexate (MTX) selection.

E59. The method of any one of E1-E32 and E50-E57, wherein said first culture medium comprises methotrexate (MTX).

E60. The method of any one of E33-E57, wherein said mammalian host cells in step (a) have been amplified by methotrexate (MTX) selection.

E61. The method of any one of E1-E60, wherein said mammalian host cell comprises about 500 copies or more of nucleic acid sequence encoding denosumab.

E62. The method of any one of E1-E61, wherein said mammalian host cell comprises about 500 copies or more of nucleic acid sequence comprising SEQ ID NO. 3.

E63. The method of any one of E1-E62, wherein said mammalian host cell comprises about 500 copies or more of nucleic acid sequence comprising SEQ ID NO:4.

E64. The method of any one of E1-E63, wherein from about 7% to about 10% the denosumab molecules comprise high-mannose at the N-298 site.

E65. The method of any one of E1-E64, wherein said high-mannose is Man-5.

E66. The method of any one of E1-E65, wherein from about 7% to about 10% the denosumab molecules comprise Man-5 at the N-298 site.

E67. The method of any one of E1-E66, wherein from about 48% to about 70% of the denosumab molecules comprise A2F-G0 at the N-298 site.

E68. The method of any one of E1-E67, wherein from about 9% to about 26% of the denosumab molecules comprise A2F-G1 at the N-298 site.

E69. The method of any one of E1-E68, wherein from about 4% to about 8% of the denosumab molecules comprise A2-G0 at the N-298 site.

E70. The method of any one of E1-E69, wherein from about 0.3% to about 5% of the denosumab molecules comprise A2F-G2 at the N-298 site.

E71. The method of any one of E1-E70, wherein from about 0.5% to about 3% of the denosumab molecules comprise A2-G1 at the N-298 site.

E72. The method of any one of E1-E71, wherein from about 0.5% to about 3% of the denosumab molecules comprise A1-G0 at the N-298 site.

E73. The method of any one of E1-E72, wherein from about 1% to about 5% of the denosumab molecules comprise A1F-G0 at the N-298 site.

E74. A composition comprising recombinantly-produced denosumab molecules, wherein at least 15% of the denosumab molecules comprise one or more glycated lysine residues.

E75. The composition of E74, wherein said glycated lysine residue comprises a glucose moiety or a galactose moiety.

E76. A composition comprising recombinantly-produced denosumab molecules, wherein at least 5% of the denosumab molecules comprise one or more glycated lysine residues that comprise a galactose moiety.

E77. The composition of E76, wherein from about 7% to about 20% of the denosumab molecules comprise one or more glycated lysine residues that comprise a galactose moiety.

E78. The composition of any one of E74-E77, wherein up to 70% of the denosumab molecules comprise one or more glycated lysine residues.

E79. The composition of any one of E74-E78, wherein from about 20% to about 30% of the denosumab molecules comprise one or more glycated lysine residues.

E80. The composition of any one of E74-E79, wherein the ratio of galactose-glycated lysine to glucose-glycated lysine is from about 1:10 to about 10:1.

E81. The composition of any one of E74-E80, wherein the ratio of galactose-glycated lysine to glucose-glycated lysine is about 1:1.

E82. The composition of any one of E74-E81, wherein from about 2% to about 14% of the denosumab molecules comprise high-mannose at the N-298 site.

E83. The composition of any one of E74-E82, wherein from 2% to 14% of the denosumab molecules comprise high-mannose at the N-298 site.

E83b. The composition of any one of E74-E82, wherein from about 4% to about 14% of the denosumab molecules comprise high-mannose at the N-298 site.

E83c. The composition of any one of E74-E82, wherein from 4% to 14% of the denosumab molecules comprise high-mannose at the N-298 site.

E83d. The composition of any one of E74-E82, wherein from about 5% to about 14% of the denosumab molecules comprise high-mannose at the N-298 site.

E83e. The composition of any one of E74-E82, wherein from 5% to 14% of the denosumab molecules comprise high-mannose at the N-298 site.

E84. The composition of any one of E74-E83, wherein from about 4% to about 11% of the denosumab molecules comprise high-mannose at the N-298 site.

E85. The composition of any one of E74-E84, wherein from 4% to 11% of the denosumab molecules comprise high-mannose at the N-298 site.

E85b. The composition of any one of E74-E84, wherein from about 5% to about 11% of the denosumab molecules comprise high-mannose at the N-298 site.

E85c. The composition of anyone of E74-E84, wherein from 5% to 11% of the denosumab molecules comprise high-mannose at the N-298 site.

E86. The composition of any one of E74-E85, wherein from 2% to 6.5%, or from 8.5% to 14%, of the denosumab molecules comprise high-mannose at the N-298 site.

E87. The composition of any one of E74-E86, wherein from 4% to 6.5%, or from 8.5% to 11%, of the denosumab molecules comprise high-mannose at the N-298 site.

E87b. The composition of any one of E74-E86, wherein from 4% to 6.5%, or from 8.5% to 14%, of the denosumab molecules comprise high-mannose at the N-298 site.

E87c. The composition of any one of E74-E86, wherein from 5% to 6.5%, or from 8.5% to 14%, of the denosumab molecules comprise high-mannose at the N-298 site.

E87d. The composition of any one of E74-E86, wherein from 5% to 6.5%, or from 8.5% to 11%, of the denosumab molecules comprise high-mannose at the N-298 site.

E88. The composition of any one of E74-E87, with the proviso that the percentage of the denosumab molecules comprising high-mannose at the N-298 site is not between 6.5% to 7.5%.

E89. The composition of any one of E74-E88, with the proviso that the percentage of the denosumab molecules comprising high-mannose at the N-298 site is not between 6.5% to 8.5%.

E90. The composition of any one of E74-E89, with the proviso that the percentage of the denosumab molecules comprising high-mannose at the N-298 site is not between 7.5% to 8.5%.

E91. The composition of any one of E74-E90, wherein from about 7% to about 10% the denosumab molecules comprise high-mannose at the N-298 site.

E92. The composition of any one of E74-E91, wherein said high-mannose is Man-5.

E93. The composition of any one of E74-E92, wherein from about 7% to about 10% the denosumab molecules comprise Man-5 at the N-298 site.

E94. The composition of any one of E74-E93, wherein from about 48% to about 70% of the denosumab molecules comprise A2F-G0 at the N-298 site.

E95. The composition of any one of E74-E94, wherein from about 9% to about 26% of the denosumab molecules comprise A2F-G1 at the N-298 site.

E96. The composition of any one of E74-E95, wherein from about 0.5% to about 3% of the denosumab molecules comprise A1-G0 at the N-298 site.

E97. The composition of any one of E74-E96, wherein from about 1% to about 5% of the denosumab molecules comprise A1F-G0 at the N-298 site.

E98. The composition of any one of E74-E97, wherein from about 4% to about 8% of the denosumab molecules comprise A2-G0 at the N-298 site.

E99. The composition of any one of E74-E98, wherein from about 0.5% to about 4% of the denosumab molecules comprise A2-G1 at the N-298 site.

E100. The composition of any one of E74-E99, wherein from about 0.3% to about 5% of the denosumab molecules comprise A2F-G2 at the N-298 site.

E101. The composition of any one of E74-E100, wherein said glycated lysine is selected from the group consisting of: (i) heavy chain K76, K98, K218, K249, K318, K327, and K335 (numbering according to SEQ ID NO:1); and (ii) light chain K104, K108, K150, K184, and K191 (numbering according to SEQ ID NO:2).

E102. A composition comprising recombinantly-produced denosumab molecules, and wherein from about 0.2% to about 1.8% of the denosumab molecules comprise high-mannose glycan at N-298 site.

E103. The composition of E102, wherein from 0.2% to 1.8% of the denosumab molecules comprise high-mannose glycan at the N-298 site.

E104. The composition of E102 or E103, wherein from about 0.5% to about 1% of the denosumab molecules comprise high-mannose glycan at the N-298 site.

E105. The composition of any one of E102-E104, wherein from 0.5% to 1% of the denosumab molecules comprise high-mannose glycan at the N-298 site.

E106. The composition of any one of E102-E105, wherein said high-mannose glycan is Man-5.

E107. The composition of any one of E102-E106, wherein from 0.2% to 1.8% of the denosumab molecules comprise Man-5 at the N-298 site.

E108. The composition of any one of E102-E107, wherein from about 0.5% to about 1% of the denosumab molecules comprise Man-5 at the N-298 site.

E109. The composition of any one of E102-E108, wherein from 0.5% to 1% of the denosumab molecules comprise Man-5 at the N-298 site.

E110. The composition of any one of E102-E109, wherein from about 30% to about 60% of the denosumab molecules comprise A2F-G0 at the N-298 site.

E111. The composition of any one of E102-E110, wherein from about 20% to about 50% of the denosumab molecules comprise A2F-G1 at the N-298 site.

E112. The composition of any one of E102-E111, wherein said from about 0.1% to about 3% of the denosumab molecules comprise A1-G0 at the N-298 site.

E113. The composition of any one of E102-E112, wherein from about 0.1% to about 4% of the denosumab molecules comprise A1F-G0 at the N-298 site.

E114. The composition of any one of E102-E113, wherein from about 4% to about 10% of the denosumab molecules comprise A2-G0 at the N-298 site.

E115. The composition of any one of E102-E114, wherein from about 1% to about 7% of the denosumab molecules comprise A2-G1 at the N-298 site.

E116. The composition of any one of E102-E115, wherein from about 3% to about 10% of the denosumab molecules comprise A2F-G2 at the N-298 site.

E117. The composition of any one of E74-E116, wherein said denosumab binds to human RANKL with a binding affinity ($K_D$) value of about 25 pM or less.

E118. The composition of any one of E74-E117, wherein said denosumab binds to human RANKL with a binding affinity ($K_D$) value of from about 1 pM to about 25 pM.

BRIEF DESCRIPTION OF THE FIGURES

FIG. 3B are tables summarizing the N-glycan profiles of samples from CP2 and CP3 processes.

FIGS. 4A-4B show the mean (t SD) serum denosumab concentration-time profiles (ng/mL) following SC administration of 60 mg Denosumab CP3 or CP2 to healthy volunteers, depicted in linear scale (FIG. 4A) and semi-logarithmic scale (FIG. 4B), respectively. FIG. 4C shows mean (±SD) percent change from baseline in serum c-telopeptide (CTX1) following subcutaneous (SC) administration of 60 mg Denosumab CP3 or CP2 to healthy volunteers. FIGS. 4D-4E shows that while Man-5 level of denosumab decreased over time, the Gal-species remained largely constant. Time courses were analyzed from 4 total CP2-patients.

FIG. 6A shows the nucleotide and amino acid sequences of the denosumab heavy chain (SEQ ID NO:3). Nucleotides 1 to 57 encode the signal peptide, which is cleaved during protein synthesis to produce a mature heavy chain. The first amino acid (E) of the mature heavy chain is indicated in bold and enlarged. FIG. 6B shows the nucleotide and amino acid sequences of the denosumab light chain (SEQ ID NO:4). Nucleotides 1 to 60 encode the signal peptide, which is cleaved during protein synthesis to produce a mature light chain. The first amino acid (E) of the mature light chain is indicated in bold and enlarged.

FIG. 7A shows the full model analysis of day 17 Man-5, with the prediction profile at the experiment center points. FIG. 7B shows Day 17 prediction of Man-5 with the glucose level set to 2.5 g/L. FIG. 7C shows the time course change in Man-5 from days 11 to 17.

FIG. 10A is a line graph showing viable cell density (VCD) of all samples. FIG. 10B are barcharts showing titer and FIG. 10C shows specific productivity of 10-day fed batch cultures. Black bars represent the control condition where glucose was supplemented to maintain 10-12 g/L level in the bioreactor during feed days. White bars represent the condition in which 10 g/L galactose was supplemented along with glucose to maintain 10-12 g/L level in the bioreactor during feed days. Hatched bars represent the condition in which 10 g/L galactose was supplemented during feed days while glucose level was allowed to drop by consumption to 1-5 g/L level in the bioreactor.

FIG. 13 is a flowchart showing cell culture expansion (growth) and production phases for denosumab CP2 and CP3 processes.

FIG. 15 is a flowchart showing cell culture and harvest for the denosumab CP2 and CP4 processes. * polydiallyldimethyl ammonium chloride (PDADMAC) and polyethylene glycol (PEG).

DETAILED DESCRIPTION OF THE INVENTION

1. Overview

Figure 1:
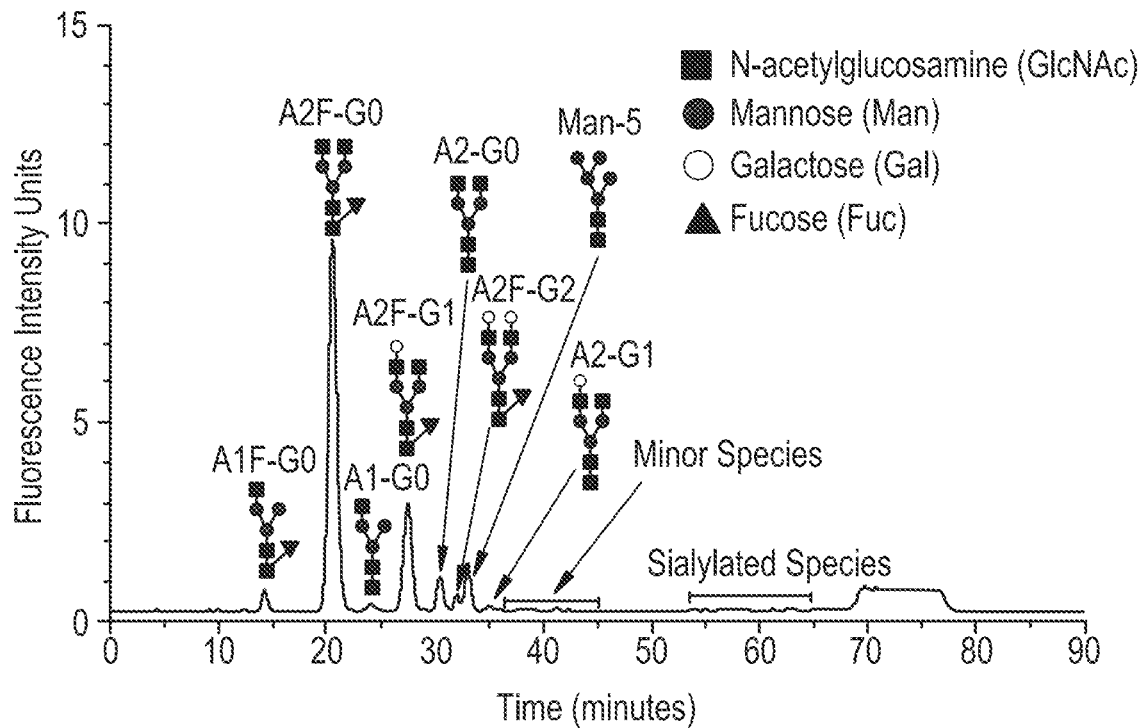
FIG. 1 is a graph showing the N-glycan profiles of samples from CP2 process.

Denosumab is a human IgG2 monoclonal antibody with affinity and specificity for human RANKL (Receptor Activator of Nuclear Factor Kappa-B Ligand). Denosumab has an approximate molecular weight of 147 kD and is currently produced in genetically engineered mammalian (Chinese hamster ovary) cells. During recombination production process, glycan moieties are attached to denosumab through post-translational modification, for example, by enzyme-mediated process (glycosylation) or non-enzyme-mediated process (glycation). Because glycans have an important role in therapeutic efficacy and in vivo half-life of an antibody, glycoform profile of a therapeutic glycoprotein needs to be characterized in order to meet regulatory agency demands.

As disclosed and exemplified herein, different culturing processes have been developed to modify the glycan profiles of denosumab. Denosumab has two N-glycosylation sites located on the 2nd constant domain of each heavy chain (residue N-298). Further, the antibody can also be modified by glycation (sometimes also referred to as "non-enzymatic glycosylation"), when a sugar moiety is attached to the antibody via a lysine residue.

In the first exemplary culturing process (referred herein as "CP2"), CHO cell line derived from AM-1/D was used. The cells were cultured a modified DMEM/F12 medium, with two bolus feeds on day 3 and 9 before the culture was harvested on day 14. The resulting key glycoforms included the following: A2F-G0 about 55%-65%, A2F-G1 about 15%-25%, and Man-5 about 4%-9%.

In the second exemplary culturing process (referred herein as "CP3"), overall higher product yields were achieved by using a slightly different process. A cell line based on CS-9 CHO cell had been amplified by methotrexate (MTX) selection during the growth phase. Due to MTX selection, the copy number of nucleic acid encoding denosumab was significantly increased, as compared to the host cells used in the CP2 process. In general, with MTX selection, it is estimated that a host cell comprises about 700-1000 copies of recombinant sequence, thereby increasing the overall yield of recombinant protein production. Notably, the recombinant denosumab produced by CP3 also showed low Man-5 content, less than 1%. Denosumab produced by CP3 process showed higher serum half-life and slower clearance in patients.

The third exemplary culturing process is referred herein as "CP4." Similar to CP3, a cell line based on CS-9 CHO cell had been amplified by MTX selection during the growth phase, thereby increasing the overall yield of denosumab production. Further, during the production phase, there was a perfusion media change on day 11. The media change included reducing the glucose concentration and adding galactose as an alternative carbohydrate source. Denosumab produced by CP4 process showed similar levels of A2F-G0 (about 55% to 65%), A2F-G1 (about 10%-19%), and Man-5 (about 4%-9%), as compared to CP2-denosumab; and higher level of Man-5 as compared to CP3-denosumab. Increased levels of glycation were observed in denosumab produced by the CP4 process. In addition, since galactose was used in CP4 as an alternative carbon source, CP4-denosumab also comprised a new species, galactose-glycated lysine.

Surprisingly, even though CP4-denosumab has shown much higher level of glycation, as compared to CP2-denosumab, its binding to RANKL ligand, as well as the biological activities, were not affected. Because lysine residue is charged and often involved in protein-protein interactions, it was surprising that significantly increased glycation did not impact biological activities. Another surprising discovery is that galactose-glycated lysine did not affect the immunogenicity of denosumab. Galactose is naturally present in human serum at approximately 0.3 mg/dL. At these low serum galactose levels, it is unlikely that healthy individuals would have circulating proteins with measurable levels of galactose glycation, the exception being patients with galactosaemia. Therefore, clinical safety of galactose glycation was previously unknown. It was discovered that, in case of denosumab, high levels of galactose-glycated denosumab did not impact immunogenicity.

2. Definitions

"Denosumab" (trade names Prolia® and Xgeva®) refers to a human monoclonal antibody comprising a heavy chain comprising SEQ ID NO:1, and a light chain comprising SEQ ID NO:2. The amino acid sequences of the heavy and light chains of denosumab is shown in Table 1. Nucleic acid sequences encoding SEQ ID Nos: 1 and 2 are shown in FIGS. 6A-6B. As illustrated in the examples, glycan profiles of denosumab may vary.

Antibodies are glycoproteins, and glycosylation heterogeneity is expected. Monoclonal antibodies contain a single consensus N-linked glycosylation site in the CH2 Fc domain of each HC, while LC lacks a consensus N-linked glycosylation site. Fc glycans primarily consist of 3 glycan classes: (1) asialylated bi antennary core fucosylated structures differing in terminal galactose content (A2GxF, where x=0, 1, or 2); (2) asialylated mono antennary core fucosylated hybrid structures differing in galactose content (A1GxMyF, where x=0 or 1 and y=3, 4, or 5); and (3) high mannose structures (Mx, where x=5, 6, 7, or 8). Denosumab is expected to contain a single N glycosylation site at N-298 on each heavy chain based on the presence of a consensus sequence, as well as historical characterization of IgG2 monoclonal antibodies produced from mammalian cell culture.

In literature, the N-glycosylation site is commonly referred to as residue N-297 according to the Kabat EU numbering. The actual residue number is residue 298 of SEQ ID NO:1. The difference is due to the numbering system; both refer to the same N residue.

Carbohydrate moieties are described herein with reference to commonly used nomenclature for oligosaccharides. A review of carbohydrate chemistry which uses this nomenclature can be found, for example, in Hubbard and Ivatt, Ann. Rev. Biochem. 50:555-583 (1981). This nomenclature includes, for instance, Man, which represents mannose; Gal which represents galactose; and Glc, which represents glucose. Commonly known glycans are shown in Table 2.

TABLE 1

Sequences of Denosumab

| | Sequence |
|---|---|
| Heavy chain amino acid sequence (SEQ ID NO: 1) | EVQLLESGGG LVQPGGSLRL SCAASGFTFS SYAMSWVRQA PGKGLEWVSG ITGSGGSTYY ADSVKGRFTI SRDNSKNTLY LQMNSLRAED TAVYYCAKDP GTTVIMSWFD PWGQGTLVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| Light chain amino acid sequence (SEQ ID NO: 2) | EIVLTQSPGT LSLSPGERAT LSCRASQSVR GRYLAWYQQK PGQAPRLLIY GASSRATGIP DRFSGSGSGT DFTLTISRLE PEDFAVFYCQ QYGSSPRTFG QGTKVEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC |

TABLE 2

Exemplary Glycan Structures

| Theoretical Mass (Da)[a] | Name and Empirical Formula | Proposed Structure |
|---|---|---|
| 1,378.3 | A1F-G0 $C_{55}O_{35}N_5H_{87}$ | |
| 1,581.5 | A2F-G0 $C_{63}O_{40}N_6H_{100}$ | |
| 1,232.2 | A1-G0 $C_{46}O_{31}N_5H_{77}$ | |
| 1,743.6 | A2F-G1 $C_{69}O_{45}N_6H_{110}$ | |
| 1,435.3 | A2-G0 $C_{57}O_{36}N_6H_{90}$ | |
| 1,394.3 | A1-G1 $C_{55}O_{36}N_5H_{87}$ | |

TABLE 2-continued

Exemplary Glycan Structures

| Theoretical Mass (Da)[a] | Name and Empirical Formula | Proposed Structure |
|---|---|---|
| 1,905.8 | A2F-G2<br>$C_{75}O_{50}N_6H_{120}$ | |
| 1,353.2 | Man 5<br>$C_{53}O_{36}N_4H_{84}$ | |
| 1,597.5 | A2-G1<br>$C_{63}O_{41}N_6H_{100}$ | |
| 1,556.4 | Man 5-GlcNAc<br>$C_{61}O_{41}N_5H_{97}$ | |
| 1,823.7 | Man 7-Fuc<br>$C_{65}O_{46}N_4H_{104}$ | |

TABLE 2-continued

Exemplary Glycan Structures

| Theoretical Mass (Da)[a] | Name and Empirical Formula | Proposed Structure |
|---|---|---|
| 1,515.4 | Man 6<br>$C_{59}O_{41}N_4H_{94}$ | |
| 1,718.6 | Man 6-GlcNAc<br>$C_{67}O_{46}N_5H_{107}$ | |
| 1,677.5 | Man 7<br>$C_{65}O_{46}N_4H_{104}$ | |
| 1,839.7 | Man 8<br>$C_{71}O_{51}N_4H_{114}$ | |

[a] Theoretical mass is based on the empirical formula and includes glycan and 2-AA.

[b] Square represents GlcNAc residue, filled circle represents Man residue, open circle represents Gal residue, and triangle represents Fuc residue.

"High-mannose" glycan is a glycan moiety comprising 5-9 mannose units, such as high-mannose 5 (Man-5) glycan, high-mannose 6 (Man-6) glycan, high-mannose 7 (Man-7) glycan, high-mannose 8 (Man-8) glycan, and high-mannose 9 (Man-9) glycan.

The high-mannose content of an antibody can be assessed according to art-known methods. Assays typically involve the release of the glycans from mAbs either by enzymatic (PNGAse-F or Endo-H) or chemical treatment (i.e. hydrazinolysis). The released glycans are then purified and subsequently analyzed without further derivatization or after the labeling with different chromophores/fluorophores. For example, the enzymatically or chemically treated sample is typically analyzed by chromatography, electrophoresis or mass spectrometry to identify high mannose-containing glycoforms of mAbs. Examples of high-mannose assays are provided herein.

The glycan content of denosumab is typically expressed as certain percentage (e.g., 2%-14% high-mannose). Unless otherwise specified, the percentage of a glycan is theoretically calculated as the number of denosumab molecules comprising such glycan, out of total denosumab molecules, in a sample. For example, 2% high-mannose means 2 denosumab molecules out of 100 denosumab molecules comprise high-mannose. This theoretical calculation assumes that 100% of Asparagines at the N-298 site is glycosylated. In practice, however, a very small percentage of antibody molecules could be aglycosylated or deglycosylated (see, e.g., Example 3.1 below, about 0.3% or less antibody molecules could be aglycosylated or deglycosylated at the N-298 site). In addition, counting glycan species at individual molecule level is impractical/impossible. Therefore, the percentage of a glycan content described herein is generally calculated based on relative percentage according to commonly used analytical methods. For example, as exemplified in Example 3.2, an enzyme is used to release all N-glycans from the protein; then glycans are separated by high performance anion exchange chromatography (HPAEC). HPAEC results in various peaks, each peak representing a glycan species.

Peak No. 8 represents Man-5. So the percentage of Man-5 (8.4% in this case) is calculated based on the area of peak 8, out of the total areas of all peaks. Another example is Example 7.1, wherein hydrophilic interaction liquid chromatography (HILIC) is used to assess N-glycan percentages. Therefore, unless otherwise specified, the percentage of a glycan is calculated according to the relative percentage of that particular glycan species, out of total N-glycans at the N-298 site, using any of the commonly used analytical method (such as HPAEC, CE-SDS, HILIC). The percentage is not to be taken literally as referring to the glycan content at the individual molecule level.

Recombinant protein production processes are typically divided into two phases. In the first phase, typically referred to as the "growth phase," cell propagation takes place. In the second phase, typically referred to as the "production phase," expression of a recombinant protein is turned on within the host cells, generally by adding an inducer (such as IPTG), or by changing the culturing condition (such as a change in temperature).

It should be noted that, as used in this specification and the appended claims, the singular forms "a", "an," and "the" include plural referents unless the context clearly dictates otherwise. The terms "a" (or "an"), as well as the terms "one or more," and "at least one" can be used interchangeably herein.

3. High-Mannose Content of Recombinantly-Produced Denosumab 3.1 Methods for Increasing High-Mannose Content of Denosumab High-mannose glycoforms are increasingly recognized as important quality attributes for therapeutic monoclonal antibodies. As described herein, the high mannose present on recombinantly-produced denosumab may be controlled by manipulating the concentration of glucose and galactose in the cell culture media.

The invention provides a method for increasing high-mannose content of the recombinantly-produced denosumab, in particular, Man-5, through the use of low or limited concentrations of glucose in combination with an alternate carbon source, in particular, galactose or sucrose. As described herein, culturing cells in a cell culture medium where glucose is limited by lowering the concentration of glucose in the cell culture medium, in combination with an alternative carbon source (e.g., galactose), resulted in a denosumab composition having am increased concentration of high mannose content, while maintaining cell growth, viability and titer at acceptable levels.

In one aspect, the invention provides a method of increasing the level of high-mannose present on denosumab molecules, wherein said denosumab molecules are recombinantly-expressed by a mammalian host cell, comprising: (a) incubating said mammalian host cell in a first culture medium during growth phase until the cell density is at least $1 \times 10^6$ viable cells/mL, wherein said first culture medium comprises from about 1 g/L to about 20 g/L glucose; and subsequently (b) incubating host cells from step (a) in a second culture medium during production phase to express said denosumab molecules, wherein said second culture medium comprises from about 0 g/L to about 10 g/L glucose and from about 5 g/L to about 20 g/L galactose; wherein from about 2% to about 14% of the denosumab molecules comprise high-mannose glycan at N-298 site.

In general, when discussing the concentrations of sugar sources (such as glucose, sucrose, or galactose), as well as other nutrients, the number (e.g., 20 g/L) generally refers to the concentration that is being fed into the bioreactor. After the medium reaches inside the bioreactor, the concentration often changes due to cell metabolism, consumption, and dilution. The actual concentration inside a bioreactor may change significantly overtime and may not always be monitored, as it depends heavily on cell density and metabolism rate. Therefore, for ease and consistency, numbers generally refer to concentrations measured before the medium is being fed the bioreactor, without considering consumption or dilution inside the bioreactor. On the other hand, concentrations inside the bioreactor are generally referred to as concentration of the "spent medium", or concentration "inside a bioreactor."

In general, during the growth phase, the glucose concentration is maintained at from about 1 g/L to about 20 g/L, either by bolus feed or perfusion, to ensure the efficient expansion of the host cells. In certain embodiments, the glucose concentration is maintained at from about 2 g/L to about 20 g/L, from about 3 g/L to about 20 g/L, from about 4 g/L to about 20 g/L, from about 2 g/L to about 19 g/L, from about 3 g/L to about 19 g/L, from about 4 g/L to about 19 g/L, from about 2 g/L to about 18 g/L, from about 3 g/L to about 18 g/L, or from about 4 g/L to about 18 g/L, by bolus feed or perfusion.

In certain embodiments, during the growth phase, the glucose concentration of the spent medium is maintained at from about 1 g/L to about 10 g/L, either by bolus feed or perfusion, to ensure the efficient expansion of the host cells. In certain embodiments, the glucose concentration of the spent medium is maintained at from about 2 g/L to about 10 g/L, from about 3 g/L to about 10 g/L, from about 4 g/L to about 10 g/L, from about 2 g/L to about 9 g/L, from about 3 g/L to about 9 g/L, from about 4 g/L to about 9 g/L, from about 2 g/L to about 8 g/L, from about 3 g/L to about 8 g/L, or from about 4 g/L to about 8 g/L, by bolus feed or perfusion.

In certain embodiments, during the growth phase, the glucose concentration of the spent medium is maintained at a level to support cell expansion to at least $1 \times 10^6$ viable cells/mL, wherein the glucose concentration is maintained by bolus feed or perfusion, wherein the glucose concentration in the bolus feed or perfusion medium is from about 4 g/L to about 20 g/L, from about 4 g/L to about 19 g/L, from about 4 g/L to about 18 g/L, from about 5 g/L to about 20 g/L, from about 5 g/L to about 19 g/L, from about 5 g/L to about 18 g/L, from about 6 g/L to about 20 g/L, from about 6 g/L to about 19 g/L, from about 6 g/L to about 18 g/L, from about 7 g/L to about 20 g/L, from about 7 g/L to about 19 g/L, or from about 7 g/L to about 18 g/L. The timing/frequency of bolus feed, or flow rate of perfusion will depend on the consumption/metabolism rate of the cell culture and is within the knowledge of a skilled artisan.

In certain embodiment, the cell density reaches from about $1 \times 10^6$ viable cells/mL to about $80 \times 10^6$ viable cells/mL during growth phase, such as at least about $1 \times 10^6$ viable cells/mL, at least about $2 \times 10^6$ viable cells/mL, at least about $3 \times 10^6$ viable cells/mL, at least about $4 \times 10^6$ viable cells/mL, at least about $5 \times 10^6$ viable cells/mL, at least about $6 \times 10^6$ viable cells/mL, at least about $7 \times 10^6$ viable cells/mL, at least about $8 \times 10^6$ viable cells/mL, at least about $9 \times 10^6$ viable cells/mL, at least about $10 \times 10^6$ viable cells/mL, at least about $20 \times 10^6$ viable cells/mL, at least about $30 \times 10^6$ viable cells/mL, at least about $40 \times 10^6$ viable cells/mL, at least about $50 \times 10^6$ viable cells/mL, at least about $60 \times 10^6$ viable cells/mL, at least about $70 \times 10^6$ viable cells/mL, at least about $80 \times 10^6$ viable cells/mL, from about $2 \times 10^6$ viable cells/mL to about $20 \times 10^6$ viable cells/mL, from about $2 \times 10^6$ viable cells/mL to about $15 \times 10^6$ viable cells/mL, from about $2 \times 10^6$ viable cells/mL to about $10 \times 10^6$ viable cells/mL, or from about $2 \times 10^6$ viable cells/mL to about $10 \times 10^6$ viable cells/mL.

When the host cells are transitioned from growth phase into the production phase, to increase the high-mannose (e.g., Man-5) content, the cells can be fed with a second culture medium wherein the concentration of glucose is reduced (e.g., from 0-8 g/L), in combination an alternative carbon source, such as galactose or sucrose, preferably galactose.

The switch to low-glucose culture medium does not need to occur at the beginning of production phase. Often, during the production phase, it is desirable to maintain the host cells in a medium containing sufficient glucose (e.g., from about 4 g/L to about 20 g/L, or more) for 3-15 days (e.g., 3-11 days) before switching to low-glucose medium. This may help to establish desirable culture parameters (such as viable cell density, or cell viability), and to maintain these parameters. After 3-15 days (such as 3-11 days) into production phase, when it is desirable to increase the high mannose content of the recombinantly-produced denosumab, the cell culture can then be fed with a cell culture medium wherein the concentration of glucose is reduced and an alternative carbon source is provided, resulting in a desired increase in high mannose content.

Factors that determine the degree to which the glucose concentration will need to be lowered include which alternate carbon source used, and how much is used; the cell culture production process; the cell type and mass and the glucose consumption. The greater the cell mass in the bioreactor, the greater the glucose consumption by the cell culture and hence the greater the amount of glucose that can be fed while still maintaining a low-glucose state that will produce the desired high mannose content. The manner in which the glucose is fed to the cell culture can also influence the amount of glucose necessary to maintain a low-glucose state that will produce the desired high mannose content. For example, in a fed-batch cell culture, glucose can be formulated into the cell culture medium and supplemented by bolus feeds. In a perfusion cell culture process, glucose concentration will depend on the feed rate (g/L/day) of the perfusion medium. In addition, the amount of glucose in the culture medium during production can be measured, such as by spent media analysis for perfusion cultures. In addition, the amount of glucose in the culture medium during production can be measured, such as by spent media analysis for perfusion cultures. It was observed that Man-5 levels increased when the amount of glucose in the spent medium was at or nearly 0 g/L. In this circumstance, just enough glucose is fed to the cells for near-total consumption, to ensure that the protein yield is not significantly impacted by glucose reduction.

Lowering the glucose concentration inside a bioreactor can be achieved, e.g., by replacing the first culture medium with the second culture medium through perfusion. Alternatively, it can be achieved by waiting for the glucose in the first culture medium to be consumed by the cells, then adjusting the bolus feed schedule and/or concentration to lower the glucose concentration inside a bioreactor.

In certain embodiments, the amount of glucose in second culture medium is lowered to a limiting amount, such that in the perfusion medium feed for example, the amount of glucose measured in spent medium is at or just above 0 g/L. The rate of glucose consumption can be determined by the rate of glucose addition and/or the mass of the cell culture. Glucose can be fed at a concentration from about 0 g/L to about 10 g/L.

In certain embodiments, the glucose concentration in second culture medium is maintained from about 0 g/L to about 10 g/L, from about 0 g/L to about 9 g/L, from about 0 g/L to about 8 g/L, from about 0 g/L to about 7 g/L, from about 0 g/L to about 6 g/L, from about 0 g/L to about 5 g/L, from about 1 g/L to about 10 g/L, from about 1 g/L to about 9 g/L, from about 1 g/L to about 8 g/L, from about 1 g/L to about 7 g/L, from about 1 g/L to about 6 g/L, or from about 0 g/L to about 5 g/L.

In combination with the lowered glucose concentration, the second culture medium should contain or be supplemented with an alternative carbon source, such as galactose or sucrose. In certain embodiments, the second culture medium comprises galactose at a concentration up to 20 g/L. For example, the galactose concentration in the second culture medium can be maintained from about 5 g/L to about 20 g/L, from about 5 g/L to about 19 g/L, from about 5 g/L to about 18 g/L, from about 5 g/L to about 17 g/L, from about 5 g/L to about 16 g/L, from about 5 g/L to about 15 g/L, from about 5 g/L to about 14 g/L, from about 5 g/L to about 13 g/L, from about 5 g/L to about 12 g/L, from about 7 g/L to about 20 g/L, from about 7 g/L to about 19 g/L, from about 7 g/L to about 18 g/L, from about 7 g/L to about 17 g/L, from about 7 g/L to about 16 g/L, from about 7 g/L to about 15 g/L, from about 7 g/L to about 14 g/L, from about 7 g/L to about 13 g/L, from about 7 g/L to about 12 g/L, from about 10 g/L to about 20 g/L, from about 10 g/L to about 19 g/L, from about 10 g/L to about 18 g/L, from about 10 g/L to about 17 g/L, from about 10 g/L to about 16 g/L, from about 10 g/L to about 15 g/L, from about 10 g/L to about 14 g/L, from about 10 g/L to about 13 g/L, or from about 10 g/L to about 12 g/L.

In certain embodiments, to increase the high-mannose content of denosumab, after 3-15 days into the production phase, the glucose concentration is lowered, and galactose is used as an alternative sugar source. For example, the glucose concentration can be lowered by using a bolus feed medium or a perfusion medium that comprises (i) from about 0 g/L to about 10 g/L, from about 0 g/L to about 9 g/L, from about 0 g/L to about 8 g/L, from about 0 g/L to about 7 g/L, from about 0 g/L to about 6 g/L, from about 0 g/L to about 5 g/L, from about 1 g/L to about 10 g/L, from about 1 g/L to about 9 g/L, from about 1 g/L to about 8 g/L, from about 1 g/L to about 7 g/L, from about 1 g/L to about 6 g/L, or from about 1 g/L to about 5 g/L glucose, and (ii) from about 5 g/L to about 20 g/L, from about 5 g/L to about 19 g/L, from about 5 g/L to about 18 g/L, from about 5 g/L to about 17 g/L, from about 5 g/L to about 16 g/L, from about 5 g/L to about 15 g/L, from about 5 g/L to about 14 g/L, from about 5 g/L to about 13 g/L, from about 5 g/L to about 12 g/L, from about 7 g/L to about 20 g/L, from about 7 g/L to about 19 g/L, from about 7 g/L to about 18 g/L, from about 7 g/L to about 17 g/L, from about 7 g/L to about 16 g/L, from about 7 g/L to about 15 g/L, from about 7 g/L to about 14 g/L, from about 7 g/L to about 13 g/L, from about 7 g/L to about 12 g/L, from about 10 g/L to about 20 g/L, from about 10 g/L to about 19 g/L, from about 10 g/L to about 18 g/L, from about 10 g/L to about 17 g/L, from about 10 g/L to about 16 g/L, from about 10 g/L to about 15 g/L, from about 10 g/L to about 14 g/L, from about 10 g/L to about 13 g/L, or from about 10 g/L to about 12 g/L galactose.

In an exemplary embodiment, the glucose concentration is lowered by using a bolus feed medium or a perfusion medium that comprises (i) from about 1 g/L to about 5 g/L glucose, and (ii) from about 10 g/L to about 12 g/L galactose. The timing/frequency of bolus feed, or flow rate of perfusion will depend on the consumption/metabolism rate of the cell culture and is within the knowledge of a skilled artisan.

It might be desirable to match the total sugar content of the low-glucose medium to the glucose content of the original growth medium. For example, if the growth medium comprises 15 g/L glucose, then, during production phase, if the low-glucose medium only comprises 3 g/L glucose, then it may be preferable to supplement it with 12 g/L galactose, such that the total sugar content matches 15 mg/L.

In certain embodiments, during production phase, after switching to low-glucose medium, the glucose concentration of the spent medium can be maintained at from about 0 to about 5 g/L, from about 0 g/L to about 4 g/L, or from about 0 g/L to about 3 g/L, by bolus feed or perfusion; and the galactose concentration of the spent medium can be maintained at from about 2 g/L to about 12.5 g/L, from about 3 g/L to about 12.5 g/L, from about 4 g/L to about 12.5 g/L, from about 2 g/L to about 10 g/L, from about 3 g/L to about 10 g/L, from about 4 g/L to about 10 g/L, from about 2 g/L to about 9 g/L, from about 3 g/L to about 9 g/L, from about 4 g/L to about 9 g/L, from about 2 g/L to about 8 g/L, from about 3 g/L to about 8 g/L, or from about 4 g/L to about 8 g/L, by bolus feed or perfusion.

In certain embodiments, in combination with the lowered glucose concentration, the cell culture medium contains or is supplemented with sucrose, at a concentration up to about 48 g/L, such as from about 16 g/L to about 24 g/L.

The mammalian cell culture is typically grown in a bioreactor, such as 500 L to 20000 L bioreactors. In certain embodiments, 1000 L to 2000 L bioreactors are used. The bioreactor is inoculated with at least $0.5 \times 10^6$ up to and beyond $3.0 \times 10^6$ viable cells/mL in a serum-free culture medium. In certain embodiments, the inoculation is about $1.0 \times 10^6$ viable cells/mL. Once inoculated into the production bioreactor, the mammalian cells undergo an exponential growth phase. The growth phase can be maintained using a fed-batch process with bolus feeds of a serum-free feed medium having from about 1 g/L to about 20 g/L glucose. These supplemental bolus feeds typically begin shortly after the cells are inoculated into the bioreactor, at a time when it is anticipated or determined that the cell culture needs feeding. For example, supplemental feeds can begin on or about day 3 or 4 of the culture or a day or two earlier or later. The culture may receive two, three, or more bolus feeds during the growth phase. Neither the basal cell culture medium nor the bolus feed medium contain galactose or sucrose.

When the cells enter the stationary or production phase, or the cell culture has achieved a desired viable cell density and/or cell titer, the fed batch bolus feeds can be discontinued and perfusion can be started. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of means including centrifugation, sedimentation, or filtration, see e.g. Voisard et al., (2003), Biotechnology and Bioengineering 82:751-65. A preferred filtration method is alternating tangential flow filtration. Alternating tangential flow is maintained by pumping medium through hollow-fiber filter modules. See e.g. U.S. Pat. No. 6,544,424. The hollow-fiber modules can be microfilters or ultrafilters.

When the fed-batch culture reaches a predetermined trigger point, such as desired cell viability, cell density, percent packed cell volume, titer, packed cell volume adjusted titer, age or the like, a switch between fed-batch and perfusion can take place. For example, this switch can take place on or about day 7 of the culture, but may take place a day or two earlier or later. The perfusion feed formulation contains glucose at a concentration of up to 20 g/L or more, but does not contain galactose or sucrose. In one embodiment, the perfusion medium contains from about 4 g/L to about 18 g/L glucose.

When the perfusion culture reaches a predetermined trigger point, such as desired cell viability, cell density, percent packed cell volume, titer, packed cell volume adjusted titer, age or the like, the glucose concentration in the cell culture medium is lowered. For example, this shift may be initiated on day 11 of the culture, but may take place a day or two earlier or later. At that time, the cell culture is perfused with cell culture medium containing a lower concentration of glucose.

The low-glucose state in the cell culture can be maintained by monitoring the concentration of glucose in the cell culture, such as by measuring glucose concentration in the spent medium, and adjusting the glucose concentration in the perfusion medium formulation to maintain the desired level.

The cell culture can be continuously maintained in a low-glucose state supplemented with galactose or sucrose. The cell culture can be maintained in a low-glucose state supplemented with galactose or sucrose until harvest. The cell culture can be restored to normal glucose level without galactose or sucrose supplements and the entire process begun again.

The cell culture could also be maintained in a perfusion culture system for both the growth and production phases. Once inoculated into the production bioreactor the mammalian cells undergo an exponential growth phase during which time the cell culture is perfused with serum-free and/or chemically defined cell culture medium.

One exemplary embodiment is the CP4 process, as descried in detail below.

In another aspect, the invention provides a method of increasing the level of high-mannose present on denosumab molecules, wherein said denosumab molecules are recombinantly-expressed by a mammalian host cell, comprising: (a) incubating said mammalian host cell in a first culture medium during growth phase until the cell density is at least $1 \times 10^6$ viable cells/mL, wherein said first culture medium comprises from about 1 g/L to about 20 g/L glucose; and subsequently (b) incubating host cells from step (a) in a second culture medium during production phase to express said denosumab molecules, wherein said second culture medium comprises from about 0 g/L to about 10 g/L glucose and from about 5 g/L to about 20 g/L galactose. As a result of the disclosed method, the percentage of denosumab molecules comprising high-mannose at N-298 site is increased, as compared to a control.

The control can be a predetermined range or threshold, a range commonly accepted in the art, or historical ranges from denosumab production. Alternatively, the control can be a reference batch, where the host cells are cultured in a culture medium where the glucose concentration is not lowered or supplemented with an alternative carbon source. For example, the host cells can be cultured in the first medium comprising from about 1 g/L to about 20 g/L (e.g., from about 4 g/L to about 18 g/L) glucose during the entire production phase, without being transitioned into second culture medium comprising from about 0 g/L to about 10 g/L (e.g., from about 1 g/L to about 5 g/L) glucose and from about 5 g/L to about 20 g/L (e.g., from about 10 g/L to about 12 g/L) galactose.

In certain embodiment, the control is a predetermined threshold. For example, the control can be high-mannose level at about 1.8% or less, about 1.7% or less, about 1.6% or less, about 1.5% or less, about 1.4% or less, about 1.3% or less, about 1.2% or less, about 1.1% or less, about 1.0% or less, about 0.9%, about 0.8%, about 0.7%, about 0.6%, about 0.5%, about 0.4%, about 0.3%, about 0.2%, or about 0.1% or less.

In another aspect, the invention provides recombinantly-produced denosumab, wherein from about 2% to about 14% of the denosumab molecules comprise high-mannose at the N-298 site. For example, from about 2% to about 14%, from about 3% to about 14%, from about 4% to about 14%, from about 5% to about 14%, from about 2% to about 13%, from about 2% to about 12%, from about 2% to about 11%, from about 3% to about 13%, from about 3% to about 12%, from about 3% to about 11%, from about 4% to about 13%, from about 4% to about 12%, from about 4% to about 11%, from about 2% to about 6.5%, from about 3% to about 6.5%, from about 4% to about 6.5%, from about 8.5% to about 14%, from about 8.5% to about 13%, from about 8.5% to about 12%, from about 8.5% to about 11%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, or about 14%, of the denosumab molecules comprise high-mannose at the N-298 site.

In certain embodiment, the percentage of the denosumab molecules comprising high-mannose at the N-298 site is from about 5% to about 14%. In certain embodiment, the percentage of the denosumab molecules comprising high-mannose at the N-298 site is from about 5% to about 12%. In certain embodiment, the percentage of the denosumab molecules comprising high-mannose at the N-298 site is from about 5% to about 11%.

In certain embodiment, the percentage of the denosumab molecules comprising high-mannose at the N-298 site is not from 6.5% to 7.5%, not from 6.5% to 8.5%, or not from 7.5% to 8.5%.

As described above, the high-mannose level, which is expressed as percentage here, is not to be taken literally as referring to counting the high-mannose content at the individual molecule level. Instead, the percentage reflects the relative percentage of high-mannose species based on overall N-glycan content of the antibody composition, using any of the commonly used analytical method. For example (see, e.g., Example 3.2, Example 7.1), the percentage can be calculated based on areas of chromatographic peaks.

The ranges of high-mannose content of denosumab provided herein are largely based on PK/PD assessment (substantially similar PK as compared to commercially available Prolia® and Xgeva®). The broadest range (e.g., 2%-14%) should not be simply taken as a determinative criterion for biosimilarity assessment by FDA. For assessment of biosimilarity, the FDA recommends a stepwise approach for obtaining the totality-of-the-evidence for demonstrating biosimilarity between a proposed biosimilar product and an innovative (reference) biological product. The stepwise approach starts with analytical studies for functional and structural characterization at various stages of manufacturing process of the proposed biosimilar product. Analytical similarity assessment involves identification of critical quality attributes (CQAs) that are relevant to clinical outcomes. Therefore, for purpose of demonstrating biosimilarity, a different or narrower range of high-mannose content might be needed. Biosimilarity might also require a biosimilar product to match other attributes (e.g., other types of glycans).

3.2 Denosumab with Decreased High-Mannose Level

Also provided herein are denosumab with decreased high-mannose level. In one exemplary embodiment (see, CP3 process described in detail below), less than 1% of the recombinantly-produced denosumab has Man-5 at the N-298 site.

In one aspect, the invention provides composition comprising recombinantly-produced denosumab molecules, and wherein from about 0.2% to about 1.8% of the denosumab molecules comprise high-mannose glycan at the N-298 site. In certain embodiments, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, from about 0.2% to about 1.8%, from about 0.2% to about 1.7%, from about 0.2% to about 1.6%, from about 0.2% to about 1.5%, from about 0.2% to about 1.4%, from about 0.2% to about 1.3%, from about 0.2% to about 1.2%, from about 0.2% to about 1.1%, from about 0.2% to about 1.0%, from about 0.3% to about 1.8%, from about 0.4% to about 1.8%, from about 0.5% to about 1.8%, from about 0.3% to about 1.5%, from about 0.4% to about 1.5%, from about 0.5% to about 1.5%, from about 0.3% to about 1.2%, from about 0.4% to about 1.2%, from about 0.5% to about 1.2%, from about 0.3% to about 1.0%, from about 0.4% to about 1.0%, or from about 0.5% to about 1.0%, of the denosumab molecules comprise high-mannose glycan at the N-298 site.

The efficacy of therapeutic antibodies is affected by the serum clearance rate i.e. serum half-life of antibodies. The serum half-life of IgG antibodies is regulated by a number of receptors, including the mannose receptors, which bind both high-mannose-containing pathogens as well as endogenous proteins. In general, IgGs containing high-mannose glycans are cleared more rapidly in humans than other glycan forms (Goetze et al. Glycobiology vol. 21 no. 7 pp. 949-959, 2011). Hence the reduction of high mannose bearing glycoforms improves half-life of an antibody composition which is a desirable quality attribute.

In particular, Goetze noted that the difference in elimination half-life between a monoclonal antibody (Mab1) and the M5-containing Mab1 population increases with decreasing dose (Table VII), indicating that M5-containing IgGs are cleared relatively faster at lower intravenous doses. The authors suggested that mannose receptor contribute to the faster clearance of the M5 IgG population and the slower relative clearance at higher doses may reflect saturation of this receptor. Although the half-life of serum IgG is generally mediated by FcRn and that of therapeutic IgGs may additionally be modulated by target-based clearance, the mannose receptor apparently contributes to more rapid clearance of non-natural (high-mannose) glycan variants of therapeutic IgGs. This is consistent with the role played by mannose receptor in the clearance of exogenous pathogens as well as unwanted endogenous molecules and is supported by earlier studies demonstrating faster clearance of M5-containing IgG1 in mice.

In a clinical study, healthy volunteers were administered with CP2-denosumab or CP3-denosumab. PK/PD analysis showed that CP3-denosumab has, on average, 10% longer half-life as compared to CP2-denosumab. Therefore, CP3-denosumab has the potential benefit of prolonged therapeutic effect due to its favorable PK/PD profiles. This beneficial effect will likely result in less-frequent dosing requirement, and increasing patient compliance.

3.3 Analytical Methods for Assessing High-Mannose Content

Various methods may be used to analyze high mannose structures on recombinantly-produced denosumab. Such methods can be used to measure one or more of: the presence and/or amount of high mannose in a glycan or glycoprotein preparation (e.g., relative to total glycan mass); the relative ratios of high mannose structures (e.g., relative ratios of high mannose species to each other (e.g., relative abundances or ratios of Man-5, Man-6, Man-7, Man-8 and/or Man-9 and isomers thereof), relative ratios of high mannose to hybrid structures, relative ratios of high mannose to complex structures, relative ratios of high mannose to fucosylated structures); the presence or abundance of modified high mannose structures (e.g., the presence or abundance of fucosylated high mannose structures).

The high-mannose content can be measured by one or more methods well-known in the art, for instance, as described in Wuhrer et al. (Journal of Chromatography B Vol. 825:124-133, 2005) and Dell et al. (Science Vol. 291:2351-2356), and those described herein including, for example, the analytical method for N-Glycan mapping of glycoproteins. Briefly, N-glycans are removed enzymatically from the recombinant glycoproteins, such as a recombinant monoclonal antibody, and labeled with a fluorescent tag (2-Aminobenzamide) at the reducing terminus. The fluorescent N-glycans are separated by high pH anion exchange chromatography (HPAEC), and detected using fluorescence detection. Separation of the neutral N-glycans is generally based on the increasing complexity in the N-glycan structures. Separation of the charged N-glycans is based on the number and type of sialic acid, sulfate, or other modifications present from which a charge number can be derived. These glycan profiles of test samples are compared visually to an appropriate standard.

The high-mannose content can also be measured using a method disclosed in WO 2007/087384, which is a high-throughput method for detecting and/or quantitating the high-mannose content of a glycoprotein. Briefly, the glycoprotein is digested with an endoglycosidase, followed by reducing the digested glycoproteins using a reducing agent (if required), and separating the digested glycoproteins by denature electrophoresis. The ratio of high-mannose/hybrid type glycan is determined by subtracting the fraction of non-glycosylated heavy chain (peak fraction without endoglycosidase treatment) from the fraction of de-glycosylated heavy chain (peak following endoglycosidase digestion). The non-glycosylated heavy chain fraction or the peak fraction without endoglycosidase treatment is generated by subjecting the same sample or composition to the same digestion condition except that no endoglycosidase is present therein. This step can be carried out concurrently with or separately from the endoglycosidase digestion step.

Any endoglycosidases that selectively cleave high mannose and hybrid glycans between GlcNAc1 and GlcNAc2 on the core glycan (or generating short glycans on the protein), while leaving complex N-linked glycans intact can be used. The specific condition for carrying out the endoglycosidase digestion, including the concentration of the enzyme, the incubation temperature and digestion time, depends on the type of endoglycosidase used. Examples of endoglycosidases related to this invention include but are not limited to Endoglycosidase H and Endoglycosidase F1. In one embodiment of the present invention, the sample comprising the glycoproteins is treated with Endoglycosidase H at 37° C. for about 2 hours, reduced with β-mercaptoethanol, and subjected to CE-SDS analysis.

Example methods for separating the de-glycosylated glycoproteins, e.g., de-glycosylated antibody, from the glycosylated glycoproteins, e.g., glycosylated antibody, include but are not limited to the following two methods:

1) CE-SDS under reducing conditions. The glycosylated glycoprotein, e.g., an antibody, is denatured with SDS and a reducing agent and the heavy chain (HC) thereof with the glycan is separated from the cleaved HC (de-glycosylated HC) by Capillary Electrophoresis-SDS (CE-SDS). An electropherogram is generated of the UV signal. The areas under the peaks are proportional to the relative amounts. Therefore the amount of High-mannose/hybrid type is determined from the fraction eluting at the earlier de-glycosylated HC position. Since the GlcNAc-HC co-migrates with de-glycosylated HC, the % de-glycosylated HC from an undigested sample is subtracted from pre-peak of a digested sample to yield the % high mannose value. Separation requires 15-30 minutes, depending on the configuration.

2) Microfluidic-based CE-SDS. The glycoprotein is denatured and separated using a "lab on a chip" instrument, such as the LC90 by Caliper. The same principle is used in the assay and the separation, though a fluorescent dye is used to detect the protein. Separation time is reduced to about 30 seconds per assay and it can be sampled from a microtiter plate.

Example 7.1 uses Hydrophilic Interaction Liquid Chromatography (HILIC). Briefly, the glycan species can be analyzed based on the following steps: (i) release of the N-glycans (e.g., by an enzyme such as PNGase F), (ii) labeling (e.g., with 2-aminobenzoic acid or 2-aminobenzamide), (iii) removal of the free label (e.g., by gel filtration or solid-phase extraction); (iv) separation of glycan species by HILIC; and (v) detection (e.g., by fluorescence spectrometry). Additional details of HILIC is provided by Melmer et. al., Analytical and Bioanalytical Chemistry, September 2010, Volume 398, Issue 2, pp 905-914.

Another commonly used method is liquid chromatography-tandem mass spectrometry (LC-MS). After the release of the N-glycans, labeling, and removal of free label, the samples can be analyzed by techniques that combine the physical separation capabilities of liquid chromatography (or HPLC) with the mass analysis capabilities of mass spectrometry (MS). See, e.g., Wang et. al., Biotech Method, 17 Jan. 2018, doi.org/10.1002/biot.201700185.

Additional suitable methods include, but are not limited to, positive ion MALDI-TOF analysis, negative ion MALDI-TOF analysis, HPLC, weak anion exchange (WAX) chromatography, normal phase chromatography (NP-HPLC), Bio-Gel P-4 chromatography, anion-exchange chromatography and one-dimensional NMR spectroscopy, and combinations thereof. See, e.g., Pace et al., Biotechnol. Prog., 2016, Vol. 32, No. 5 pages 1181-1192; Shah, B. et al. J. Am. Soc. Mass Spectrom. (2014) 25: 999; Mattu et al., JBC 273: 2260-2272 (1998); Field et al., Biochem J 299(Pt 1): 261-275 (1994); Yoo et al., MAbs 2(3): 320-334 (2010) Wuhrer M. et al., Journal of Chromatography B, 2005, Vol. 825, Issue 2, pages 124-133; Ruhaak L. R., Anal Bioanal Chem, 2010, Vol. 397:3457-3481; Kurogochi et al., PLOS One 10(7): e0132848; doi:10.1371/journal.pone.0132848; Thomann et al., PLOS One 10(8): e0134949. Doi:10.1371/journal.pone.0134949; Pace et al., Biotechnol. Prog. 32(5): 1181-1192 (2016); and Geoffrey, R. G. et. al. Analytical Biochemistry 1996, Vol. 240, pages 210-226.

When assessing the high-mannose content, a control may be used for comparison purpose, as described above.

4. Glycation of Recombinantly-Produced Denosumab

Glycation (sometimes called non-enzymatic glycosylation) is the result of the covalent bonding of a sugar molecule, such as glucose or fructose, to a protein or lipid molecule, without the controlling action of an enzyme. Glycation occurs at positively charged primary amines, generally located on the surface of protein molecules. No specific sequence that signals a potential glycation site has been identified. However, basic residues (arginines and other lysines) have been observed to correlate with glycation occurrence in some proteins with known structures. Glycation is distinct from N-glycosylation at the N-298 site.

For therapeutic mAbs, the potential effects of glycation, such as blocking the biologically functional site or further degradation that induces aggregation, make glycation a potential critical quality attribute (CQA). The effect of glycation on antibody activities ranged from no effect (Quan et al., Anal Biochem 2008; 373(2):179-91; Miller et al., J Pharm Sci 2011; 100(7):2543-50) to loss of activity (Kennedy et al., Clin Exp Immunol 1994; 98(2):245-51; Dolhofer et al., Biol Chem Hoppe Seyler 1985; 366(4):361-6).

Because lysine residue is charged and often involved in protein-protein interactions, it was surprising that significantly increased glycation did not impact biological activities of CP4-denosumab. Accordingly, in one aspect, the invention provides a composition comprising recombinantly-produced denosumab molecules, wherein at least 15% of the denosumab molecules comprise one or more glycated lysine residues. As shown in the examples, the CP4-denosumab shows a higher level of glycation as compared to CP2-denosumab. Surprisingly, despite the higher level of glycation, the binding of denosumab to its ligand, and the biological activities, are not affected. In fact, in one experiment with forced glycation, up to 70% of the denosumab molecules comprise one or more glycated lysine residues, while its biological activities were maintained. Therefore, in certain embodiments, about 15%, about 20%, about 25%, about 30%, about 35%, about 40%, about 45%, about 50%, about 55%, about 60%, about 65%, about 70%, from about 15% to about 70%, from about 15% to about 65%, from about 15% to about 60%, from about 15% to about 55%, from about 15% to about 50%, from about 15% to about 45%, from about 15% to about 40%, from about 15% to about 35%, from about 15% to about 30%, from about 20% to about 70%, from about 20% to about 65%, from about 20% to about 60%, from about 20% to about 55%, from about 20% to about 50%, from about 20% to about 45%, from about 20% to about 40%, from about 20% to about 35%, from about 20% to about 30%, or about 24% of the denosumab molecules comprise one or more glycated lysine residues.

Another surprising discovery is that galactose-glycated lysine did not affect the biological activity or immunogenicity of denosumab. Galactose is naturally present in human serum at approximately 0.3 mg/dL. At these low serum galactose levels, it is unlikely that healthy individuals would have circulating proteins with measurable levels of galactose glycation, the exception being patients with galactosaemia. Therefore, clinical safety of galactose glycation was unknown. It was discovered that, in case of denosumab, high levels of galactose-glycated denosumab did not impact immunogenicity. Therefore, in another aspect, the invention provides a composition comprising recombinantly-produced denosumab molecules, wherein at least 5% of the denosumab molecules comprise one or more glycated lysine residues that comprise a galactose moiety. For example, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, from about 5% to about 35%, from about 5% to about 30%, from about 5% to about 25%, from about 5% to about 20%, from about 5% to about 15%, from about 10% to about 35%, from about 10% to about 30%, from about 10% to about 25%, from about 10% to about 20%, or from about 10% to about 15%, of the denosumab molecules comprise one or more glycated lysine residues that comprise a galactose moiety.

Similar to N-298 glycan levels described above, glycation level, which is expressed as percentage here, is not to be taken literally as referring to counting molecules with glycated lysines at the individual molecule level. Instead, the percentage reflects the relative percentage of glycated lysine species based on overall lysine content of the antibody composition, using any of the commonly used analytical methods. See, e.g., Example 7.2, where percentage of glycated lysine at K-98 is calculated based on CE-HPLC peaks.

In certain embodiments, the ratio of galactose-glycated lysine to glucose-glycated lysine is from about 1:10 to about 10:1, such as about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, from about 7:1 to about 1:7, from about 6:1 to about 1:6, from about 5:1 to about 1:5, from about 4:1 to about 1:4, from about 3:1 to about 1:3, or from about 2:1 to about 1:2.

In certain embodiments, the glycated lysine is selected from the group consisting of: (i) heavy chain K76, K98, K218, K249, K318, K327, and K335; and (ii) light chain K104, K108, K150, K184, and K191.

In certain embodiments, the denosumab molecules of the invention bind with high affinity to human RANKL, but not to murine RANKL. The binding affinity of an antibody can be expressed as a $K_D$ value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ (dissociation/association) and is expressed as a molar concentration (M), and the smaller the $K_D$, the stronger the affinity of binding. $K_D$ values for antibodies can be determined using methods well established in the art. Unless otherwise specified, "binding affinity" refers to monovalent interactions (intrinsic activity; e.g., binding of an antibody to an antigen through a monovalent interaction).

The value of $K_D$ can be determined directly by well-known methods, and can be computed even for complex mixtures by methods such as those, for example, set forth in Caceci et al. (1984, Byte 9:340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein.

One exemplary method for measuring binding affinity ($K_D$) value is surface plasmon resonance (SPR), typically using a biosensor system such as a BIACORE® system. SPR refers to an optical phenomenon that allows for the analysis of real-time biospecific interactions by detection of alterations in protein concentrations within a biosensor matrix, for example using the BIACORE® system. BIAcore kinetic analysis comprises analyzing the binding and dissociation of an antigen from a chip with an immobilized molecule (e.g., a molecule comprising an antigen-binding domain), on their surface; or the dissociation of an antibody, or antigen-binding fragment thereof, from a chip with an immobilized antigen.

In certain embodiments, the binding affinity ($K_D$) value is measured using solution-based kinetic exclusion assay (KinExA™). In a particular embodiment, the KinExA measurement is conducted using a KinExA™ 3200 instrument (Sapidyne). The Kinetic Exclusion Assay (KinExA™) is a general-purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the $K_D$ of high affinity interactions where the off-rate of the interaction may be very slow. The KinExA™ methodology can be conducted generally as described in Drake et al (2004) Analytical Biochemistry 328, 35-43.

Another method for determining the $K_D$ of an antibody is by using Bio-Layer Interferometry, typically using OCTET® technology (Octet QKe system, ForteBio).

The binding affinity for denosumab is in general below 100 pM. In certain embodiments, the denosumab binds to human RANKL with an affinity of about 100 pM or less, about 75 pM or less, about 50 pM or less, about 25 pM or less, about 20 pM or less, about 10 pM or less, about 5 pM or less, from about 0.1 pM to about 50 pM, from about 0.5 pM to about 50 pM, from about 1 pM to about 50 pM, from about 0.1 pM to about 25 pM, from about 0.5 pM to about 25 pM, or from about 1 pM to about 25 pM. In certain embodiment, the binding affinity is measured according to the method disclosed in Kostenuik et al., Journal of Bone and Mineral Research, vol. 24, 182-195 (2009), through solution equilibrium binding analysis using a KinExA 3000 system (Sapidyne Instruments). Briefly, Reacti-Gel 63 beads were precoated with 20 mg/ml of human RANKL at 4° C. overnight, blocked with 1 mg/ml BSA for 2 h, and washed three times in PBS. Denosumab (50 pM) was incubated with various concentrations of soluble human RANKL (0-5 nM) at room temperature for >6 h to allow for equilibrium binding before being passed through the RANKL-coated beads. The binding of free denosumab to the beads was quantified by fluorescently labeled (cyanine Cy5 dye) goat anti-human antibody.

A number of assays can be used to assess glycation level. One exemplary method is boronate affinity chromatography. Boronate affinity chromatography (BAC) is a technique for isolation and enrichment of cis-diol compounds. Boronate functional groups on the stationary phase will form a tetrahedral anion under alkaline pH conditions, which can interact with the cis-1,2-diol arrays found on sugar molecules (Quan et al., Anal Biochem 2008; 373(2):179-91) and separate glycated from non-glycated species. To elute the glycated species, the interactions are disrupted by lowering the pH or adding a competing source of hydroxyl groups, such as sorbitol. BAC has been used for the analysis of carbohydrates and intact proteins.

For antibody glycation analysis, BAC is a common method of identification, quantitation and isolation of glycated antibodies because it requires minimum sample preparation and uses native running conditions. Optimization of the concentration of shielding agent, pH and buffer salt composition allows the quantitation of the glycation level of the bulk-drug substance.

Another method for assessing glycation level is charge-based methods. Capillary isoelectric focusing (cIEF) or imaged capillary electric focusing (icIEF) are charge-based separation methods that can detect glycation due to the loss of positive charge on the glycation sites. There is a shift to the acidic region for fully glycated, retained boronate fractions compared with the non-glycated, non-retained boronate fraction. The icIEF has been known to separate species with 0.05-pI difference and can resolve a glycated antibody that theoretically has a 0.09-pI unit difference due to a blocked lysine residue. This charge difference separation is also observable in co-mixed glycated and non-glycated boronate fractions.

Ion exchange chromatography (IEC) may also resolve glycated and non-glycated proteins that have surface charge difference. Analysis of glycated boronate fractions reveals a distinct acidic shift to the main peak under linear gradient conditions. Correspondingly, the acidic variants fractionated from the IEC also show a small enrichment in glycation.

Quan et al. (supra) reported a shift to the acidic region for the fully glycated boronate-retained antibody compared to the original unfractionated antibody. The amount of shift was equivalent to ~0.5 mM sodium chloride in the linear gradient. The IEC peaks for the boronate-retained fraction were also noticeably broadened, whereas the IEC peaks for the boronate non-retained fraction (non-glycated) were sharper than the unfractionated starting material. However, IEC sometimes may not have sufficient resolution to separate the glycation species within the starting material, which presents the combined charge effect from multiple sites of low-level glycation across the molecule. In comparison, molecules with zero, one, or two lysine residues on the carboxyl termini are thoroughly resolved from each other, apparently due to the singular and unique positional interactions with the resin.

Another method for assessing glycation level is liquid chromatography-mass spectrometry. Top-down mass spectrometry of the intact antibody or enzyme-cleaved mAb fragments can also be used to determine glycation level, either by matrix-assisted laser desorption/ionization (MALDI) (see, e.g., Kislinger et al., Ann N Y Acad Sci 2005; 1043:249-59), or electrospray ionization (ESI) (see, e.g., Miller et al., J Pharm Sci 2011; 100(7):2543-50). As each glycation site shows a +162 Da mass shift, the top-down approach can be used as a quick estimation of glycation level in the antibody. It has been reported that, after deglycosylation and removal of C-terminal lysine, the quantification of glycation by mass spectrometry could have a limit of detection at 1.0% and a limit of quantitation at 3.0%, and there is a correlation between the BAC and mass spectrometry results.

To locate the glycation site, a bottom-up peptide mapping approach is commonly used. Since trypsin is inhibited by glycation of lysine residues, a missed tryptic cleavage with a +162 Da mass addition indicates a glycated lysine. Tryptic peptide mapping of the collected BAC retained fraction or of the forced glycated sample reveals sites of glycation susceptibility across the antibody.

An alternative way of fragmentation in mass spectrometry is the electron transfer dissociation (ETD). Studies on the fragmentation method comparison show ETD provides complete sequence fragmentation without any neutral loss.

One way of improving the sensitivity and reducing the neutral loss of the glycated peptide is by using sodium borohydride or sodium cyanoborohydride reduction followed by trypsin cleavage and peptide map analysis with MS/MS detection (see, e.g., Brady et al., Anal Chem 2007; 79(24):9403-13). In this approach, the bond between the carbohydrate and peptide is stabilized due to the reduced glycated sugar moiety, which results in higher quality MS/MS spectra.

Liquid chromatography-tandem mass spectrometry (LC-MS/MS) is also a commonly used method to study level of protein glycation.

Colorimetric assay may also be used. The ketoamine formed from antibody glycation can be quantitated by the nitroblue tetrazolium (NBT) reduction assay. NBT is reduced by the ketoamine form of glycated protein, which results in a change in absorbance at 525 nm. This method has been used to measure poly-lysine and glycated albumin.

Additionally, an enzyme-linked immunosorbent assay (ELISA) format has been applied to study glycated antibodies, utilizing the binding between a sample and a biotin-conjugated primary antibody that targets a specific kind of glycation end product.

5. Other Glycan Species

Commonly known glycans are shown in Table 2. In one aspect, the invention provides a composition comprising recombinantly-produced denosumab molecules, wherein from about 48% to about 70% of the denosumab molecules comprise A2F-G0. For example, from about 48% to about 55%, from about 50% to about 65%, from about 50% to about 60%, or from about 55% to about 65% of the denosumab molecules comprise A2F-G0.

In another aspect, the invention provides a composition comprising recombinantly-produced denosumab molecules, wherein from about 30% to about 60% (e.g., from about 30% to about 55%, from about 30% to about 50%, from about 30% to about 45%, from about 35% to about 55%, from about 35% to about 50%, or from about 35% to about 45%) of the denosumab molecules comprise A2F-G0 at the N-298 site.

In one aspect, the invention provides a composition comprising recombinantly-produced denosumab molecules, wherein from about 9% to about 26% (e.g., from about 10% to about 26%, from about 11% to about 26%, from about 12% to about 26%, from about 13% to about 26%, from about 10% to about 20%, or from about 15% to about 25%) of the denosumab molecules comprise A2F-G1.

In another aspect, the invention provides a composition comprising recombinantly-produced denosumab molecules, wherein from about 20% to about 50% of the denosumab molecules comprise A2F-G1 at the N-298 site. For example, from about 25% to about 45%, from about 25% to about 40%, from about 30% to about 45%, or from about 30% to about 40% of the denosumab molecules comprise A2F-G1.

In one aspect, the invention provides a composition comprising recombinantly-produced denosumab molecules, wherein said from about 0.1% to about 3% of the denosumab molecules comprise A1-G0 at the N-298 site. In another aspect, the invention provides a composition comprising recombinantly-produced denosumab molecules, wherein said from about 0.5% to about 3% of the denosumab molecules comprise A1-G0 at the N-298 site.

In one aspect, the invention provides a composition comprising recombinantly-produced denosumab molecules, wherein from about 0.1% to about 4% of the denosumab molecules comprise A1F-G0 at the N-298 site. In another aspect, the invention provides a composition comprising recombinantly-produced denosumab molecules, wherein from about 1% to about 5% of the denosumab molecules comprise A1F-G0 at the N-298 site.

In one aspect, the invention provides a composition comprising recombinantly-produced denosumab molecules, wherein from about 4% to about 10% of the denosumab molecules comprise A2-G0 at the N-298 site. In another aspect, the invention provides a composition comprising recombinantly-produced denosumab molecules, wherein from about 4% to about 8% of the denosumab molecules comprise A2-G0 at the N-298 site In one aspect, the invention provides a composition comprising recombinantly-produced denosumab molecules, wherein from about 1% to about 7% of the denosumab molecules comprise A2-G1 at the N-298 site. In one aspect, the invention provides a composition comprising recombinantly-produced denosumab molecules, wherein from about 0.5% to about 4% of the denosumab molecules comprise A2-G1 at the N-298 site.

In one aspect, the invention provides a composition comprising recombinantly-produced denosumab molecules, wherein from about 3% to about 10% of the denosumab molecules comprise A2F-G2 at the N-298 site. In one aspect, the invention provides a composition comprising recombinantly-produced denosumab molecules, wherein from about 0.3% to about 5% of the denosumab molecules comprise A2F-G2 at the N-298 site.

In one aspect, the invention provides a composition comprising recombinantly-produced denosumab molecules, wherein about 5% or less, about 4% or less, about 3% or less, about 2% or less, from about 0.1% to about 5%, from about 0.1% to about 4%, from about 0.1% to about 3%, from about 0.1% to about 2.5%, from about 0.1% to about 2% of the denosumab molecules comprise sialylated N-glycan at the N-298 site. In one aspect, the invention provides a composition comprising recombinantly-produced denosumab molecules, wherein from about 0.3% to about 1% of the denosumab molecules comprise sialylated N-glycan at the N-298 site. In one aspect, the invention provides a composition comprising recombinantly-produced denosumab molecules, wherein from about 0.3% to about 2% of the denosumab molecules comprise sialylated N-glycan at the N-298 site. In one aspect, the invention provides a composition comprising recombinantly-produced denosumab molecules, wherein from about 1% to about 3% of the denosumab molecules comprise sialylated N-glycan at the N-298 site.

As described above, the levels of various glycan species, which are expressed as percentages here, are not to be taken literally as referring to counting the N-glycan contents at the individual molecule level. The percentage reflects the relative percentage of a glycan species based on overall N-glycan content of the antibody composition, using any of the commonly used analytical method. For example (see, e.g., Example 3.2 and Example 7.1), the percentage can be calculated based on areas of chromatographic peaks.

Although the denosumab molecules produced by the exemplified processes showed different glycan contents of the above-described species, unlike high-mannose, the biological activities and PK/PD profiles of denosumab are not affected by the variations of these glycan species. Therefore, the glycan profiles could potentially tolerate significant variations. In certain embodiments, it may be desirable to have from about 48% to about 70% A2F-G0, and about 13% to about 26% A2F-G1; or from about 48% to about 70% A2F-G0, and about 10% to about 20% A2F-G1.

Further, the broadest ranges (e.g., from about 48% to about 70% of the denosumab molecules comprise A2F-G0) should not be simply taken as determinative criteria for biosimilarity assessment, as the biosimilarity assessment is based on totality-of-the-evidence. For example, the presence or absence of a sugar residue (e.g., fucose, sialic acid, terminal 3-galactose) on the Fc glycan affects the conformation of the Fc, thereby potentially affecting the Fc-mediated effector functions. G0 glycan is known to interact with mannose binding protein to (i) activate complement and (ii) facilitate serum clearance (see, e.g., Dong, et al., J. Immunol., 163 (1999), pp. 5427-5434; Malhotra, et al. Nat. Med., 1 (1995), pp. 237-243). G2 glycoform is known to be increased in pregnant women and umbilical cords (Kibe, et al. J. Clin. Biochem. Nutr., 21 (1996), pp. 57-63). Desialylation of intravenous immunoglobulin (IVIG) is known to abrogate anti-inflammatory properties in KN mice (Yang et al., Anal. Biochem., 448 (2014), pp. 82-91). Loss of core $\alpha(1,6)$ fucose on IgG is known to enhanced antibody-dependent cell-mediated cytotoxicity (ADCC) activity (see, e.g., Ferrara, et al. Proc. Natl. Acad. Sci. U.S.A, 108 (2011), pp. 12669-12674; Shields, et al. J. Biol. Chem., 277 (2002), pp. 26733-26740. Finally, the terminal monosaccharide of N-linked complex glycans is sometimes occupied by sialic acid. Presence of this sialic acid affects absorption, serum half-life, and clearance from the serum, as well as the physical, chemical and immunogenic properties of the respective glycoprotein (see, e.g., Bork et al., J Pharm Sci. 2009 October; 98(10):3499-508. doi: 10.1002/jps.21684). Therefore, for purpose of demonstrating biosimilarity, different or narrower ranges of glycan contents might be needed.

6. Cell Lines

The cell lines (also referred to as "host cells") used in the invention are genetically engineered to express denosumab. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in Current Protocols in Molecular Biology, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NS0, NS1), PC12, WI38 cells, and Chinese hamster ovary (CHO) cells.

In certain embodiments, the mammalian host cell is a rodent cell. Examples of rodent cell lines include e.g., baby hamster kidney (BHK) (e.g., BHK21, BH TK), mouse Sertoli (TM4), buffalo rat liver (BRL 3A), mouse mammary tumor (MMT), rat hepatoma (HTC), mouse myeloma (NS0), murine hybridoma (Sp2/0), mouse thymoma (EL4), Chinese Hamster Ovary (CHO) and CHO cell derivatives, murine embryonic (NIH/3T3, 3T3 Li), rat myocardial (H9c2), mouse myoblast (C2C12), and mouse kidney (miMCD-3).

In certain embodiments, the mammalian host cell is a CHO cell. As used herein, a "CHO cell" also includes a CHO derivative, where additional genetic modifications have been introduced to a CHO cell. CHO cells are widely used for the production of complex recombinant proteins, e.g. cytokines, clotting factors, and antibodies (Brasel et al. (1996), Blood 88:2004-2012; Kaufman et al. (1988), J. Biol Chem 263:6352-6362; McKinnon et al. (1991), J. Mol Endocrinol 6:231-239; Wood et al. (1990), J. Immunol. 145:3011-3016).

Suitable CHO cells include, e.g., DUXB11 and DG44 lines. These two cell lines are deficient in dihydrofolate reductase (DHFR) activity, and hence dependent upon an exogenous source of nucleotide precursors for growth. The DHFR deficiency is a readily manipulated phenotype suitable to select for genome integration and stable expression of exogenous DNA. Genomic integration is accomplished by transfecting the cells with expression cassettes for the gene of interest and a DHFR gene. Post-transfection, cells are placed in selection media lacking nucleotide precursors. In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

Recombination protein expression in DHFR-deficient cell lines can be further enhanced by adding methotrexate (MTX) to the cultures, such that a high copy number of the introduced expression vector can be selected. MTX is a competitive inhibitor of the DHFR enzyme. Applying this additional selection pressure on top of the absence of nucleotide precursors enables the selection and isolation of the minor population of cells that have undergone a spontaneous amplification of the integrated expression vector containing the DHFR selectable marker and, in most cases, the gene of interest. The presence of multiple gene copies helps to achieve high level of expression of exogenous proteins. Alternatively, MTX selection can be carried out independent of DHFR-deficiency (i.e., use MTX to select a host cell that is originally DHFR-competent).

Another suitable CHO cell line is the wild-type CHO-K1 cell line (e.g., ATCC #CCL-61), and its derivative CHO-K1 SV. One commonly used selection method for CHO-K1 cell lines are glutamine synthetase (GS) selection. Absent an exogenous source of glutamine, cell survival is dependent on the GS enzyme to produce glutamine. With host cell lines such as murine myeloma-derived NS/0 cells and CHO cells, which have relatively low endogenous GS enzymatic activity, the method allows a simple selection scheme when using a GS selectable marker in the expression vector and glutamine-free selection media. Similar to the DHFR/MTX system, the GS competitive inhibitor methionine sulphoximine (MSX) can be added to the media to apply additional pressure and select for CHO cells that are driving high levels of expression from the integrated vector.

CHO-K1 cells, or any other commonly used CHO cells, can also be selected based on MTX, with or without DHFR-deficiency. In general, when a DFHR-deficient cell line is used, the number of copies of exogenous sequences is typically much higher, sometimes as high as a few hundred copies.

Other CHO cell strains suitable for the invention described herein include, e.g., CHO-ICAM-1 cells, and CHO-hIFNγ cells. These genetically modified cells permit stable insertion of recombinant DNA into a specific gene or expression region of the cells, amplification of the inserted DNA, and selection of cells exhibiting high level expression of the recombinant protein.

Additional examples of CHO cell lines typically used in the industrial laboratory include CS-9 and AM-1/D cells (described in U.S. Pat. No. 6,210,924). Both CS-9 and AM1/D are derived from DUX B11 through adaptation to serum-free medium and subcloning. Other exemplary CHO cell lines include EM9 (ATCC CRL-1861), UV20 (ATCC CRL-1862), CHO dfhr− (ECACC 94060607), RR CHO KI (ECACC 92052129), hCBE11 (ATCC PTA-3357), E77.4 (ATCC PTA-3765), hLT-B: R-hG1 CHO #14 (ATCC CRL-1965), MOR-CHO-MORAb-003-RCB (ATCC PTA-7552), AQ.C2 clone 11B (ATCC PTA-3274), AQ.C2 clone 11B (ATCC PTA-3274), hsAQC2 in CHO-DG44 (ATCC PTA-3356), xrs5 (ATCC CRL-2348), Lec1 [originally named Pro-5WgaRI3C] (ATCC CRL-1735), Pro-5 (ATCC CRL-1781), ACY1-E (ATCC 65421), ACY1-E (ATCC 65420), pgsE-606 (ATCC CRL-2246), CHO-CD36 (ATCC CRL-2092), pgsC-605 (ATCC CRL-2245), MC2/3 (ATCC CRL-2143), CHO-ICAM-1 (ATCC CRL-2093), and pgsB-618 (ATCC CRL-2241). Cell lines may be selected by determining which ones have high expression levels of recombinant denosumab.

As exemplified herein, in CP3 and CP4 processes, the CHO cells were amplified using MTX selection during growth phase. It is estimated that, in general, with MTX selection, a host cell comprises about 700-1000 copies of recombinant sequence, thereby increasing the overall yield of recombinant protein production. Therefore, in certain embodiments, mammalian host cells of the invention have been amplified by methotrexate (MTX) selection. In certain embodiments, the mammalian host cell comprises about 500 copies or more of nucleic acid sequence encoding denosumab, such as about 500 copies or more, about 600 copies or more, or about 700 copies or more.

In certain embodiments, the mammalian host cell of the invention comprises about 500 copies or more of nucleic acid sequence comprising SEQ ID NO. 3, and/or about 500 copies or more of nucleic acid sequence comprising SEQ ID NO:4.

In certain embodiments, the mammalian host cell of the invention comprises a nucleic acid sequence encoding SEQ ID NO:1, and/or a nucleic acid sequence encoding SEQ ID NO:2. In certain embodiments, the mammalian host cell of the invention comprises a nucleic acid sequence encoding an antibody, wherein said antibody comprises a heavy chain comprising SEQ ID NO:1, and a light chain comprising SEQ ID NO:2. In certain embodiments, the mammalian host cell of the invention comprises a nucleic acid sequence comprising SEQ ID NO. 3, and/or a nucleic acid sequence comprising SEQ ID NO:4.

In certain embodiments, the CHO cell line is a cell line that provides low levels of high-mannose at N-298 site when cultured in a medium that provides sufficient glucose. Such host cells include those CHO cells that, when cultured in a culture medium comprising 1 g/L to 20 g/L glucose (such as 4 g/L to 20 g/L glucose), produces denosumab compositions wherein the high-mannose level at the N-298 site is about 1.8% or less. For example, when the host cells are cultured in a medium comprising from about 1 g/L to about 20 g/L (e.g., from about 4 g/L to about 18 g/L) glucose during the entire production phase (without transitioning to a low-glucose medium), the high-mannose level at the N-298 site is about 1.8% or less, about 1.7% or less, about 1.6% or less, about 1.5% or less, about 1.4% or less, about 1.3% or less, about 1.2% or less, about 1.1% or less, about 1.0% or less, about 0.9%, about 0.8%, about 0.7%, about 0.6%, about 0.5%, about 0.4%, about 0.3%, about 0.2%, or about 0.1% or less. Because such CHO cells do not provide desired high-mannose content at the N-298 site when cultured in a routine glucose-rich medium, there is a particular advantage to use the methods described herein, in order to increase the high-mannose level of denosumab molecules produced by these CHO cell hosts.

EXAMPLES

Example 1: Comparison of CP2 and CP3 Culturing Processes

The CP2 culture expansion process began by thawing a vial from the 70S working cell bank. The contents of the thawed vial were transferred into CP2 cell culture growth medium in shaker flasks. The cultures were passaged in successively larger shaker flasks until enough cell mass was available to be pooled for the inoculation of a 20 L bioreactor. The culture was then expanded into a 60 L bioreactor, followed three days later by expansion into a 300 L bioreactor. After three to four days in the 300 L bioreactor the 2,000 L production bioreactor was inoculated.

The CP3 culture expansion process began by thawing a vial from a WCB of the 25B12 cell line. The contents of the thawed vial were transferred into CP3 cell culture growth medium containing methotrexate (MTX) in shaker flasks. The cultures were passaged in successively larger shaker flasks until enough cell mass was available to be pooled for the inoculation of a 10 L culture bag bioreactor. After three days in the 10 L culture bag bioreactor the cell mass was inoculated into a 50 L bioreactor, at which stage the MTX was removed from the growth medium. This was followed every three days by subsequent expansion into a 100 L, then 500 L bioreactor. After three days in the 500 L bioreactor, the 2,000 L production bioreactor was inoculated.

A process flow diagram comparing the CP2 and CP3 cell culture expansion and production processes is presented in FIG. 13. Both processes used three inoculum bioreactor stages before enough biomass was generated to inoculate the production bioreactor. During the operation of the inoculum bioreactors the pH, temperature, pressure, agitation and dissolved oxygen were controlled at set-points specific to each process. The CP2 process involved full volume transfers between inoculum bioreactors while the CP3 process targeted an initial viable cell density (VCD). This was due to operational preferences.

The cell line change from the CP2 to CP3 resulted in higher yields. The CP3 cell line (25B12) is based on the CS-9 parent CHO cell.

The other change was the introduction of a culture bag unit operation to the culture expansion process. This is a disposable bioreactor technology that was introduced to reduce the number of shaker flasks required for inoculation of the N-3 bioreactor.

Both production bioreactor processes were operated in a 2,000 L production vessel at the same temperature set-point. During the operation of the production bioreactor the temperature, initial VCD, pH and dissolved oxygen were controlled at set-points specific to each process, having been optimized for the different cell lines.

Both processes were inoculated by dilution of the previous seed bioreactor (N−1) culture into the production bioreactor batch medium. The CP2 process involved a full volume transfer between the inoculum bioreactor, to a maximum initial VCD in the production bioreactor of $10 \times 10^5$ cell/mL. The CP3 process targeted an initial VCD of $5 \times 10^5$ cell/mL. The difference was due to operational preferences.

The CP2 production process was based on a modified DMEM/F12 medium and there were two bolus feeds on day 3 and 9 before the culture is harvested on day 14. The CP2 feed medium was based on ACO 4.4 and contained soy hydrolysate. The CP3 production process was based on IMX 7.0 medium and there were three bolus feeds on day 4, day 7 and day 9 before the culture was harvested on day 10. The CP3 feed medium was based on AFM004 and AFM020 media and contained yeast extract (Yeastolate). All media from both processes were based on DMEM/F12 media and had been optimized for the different cell lines.

Example 2: Comparison of CP2 and CP3 Harvesting and Purification Processes

After completing the production phase, the bioreactor contents were chilled and harvested. The CP2 process was chilled to 18±3° C. and the CP3 process was chilled to 10-15° C. Harvest clarification encompassed disc-stack centrifugation, depth filtration (Stage 1) and membrane filtration (Stage 2).

The disc-stack centrifugation accomplished the primary separation of the production cells and cell debris from the culture medium. The centrifugation was followed by the stage 1 (depth) filtration which further polished the harvest centrate such that the stage 2 (membrane) filtration and subsequent purification operations could be performed without significant fouling. Following the stage 1 filter, the stage 2 membrane filter provided a harvest filtrate pool with high degree of clarity and bioburden reduction.

Figure 14:
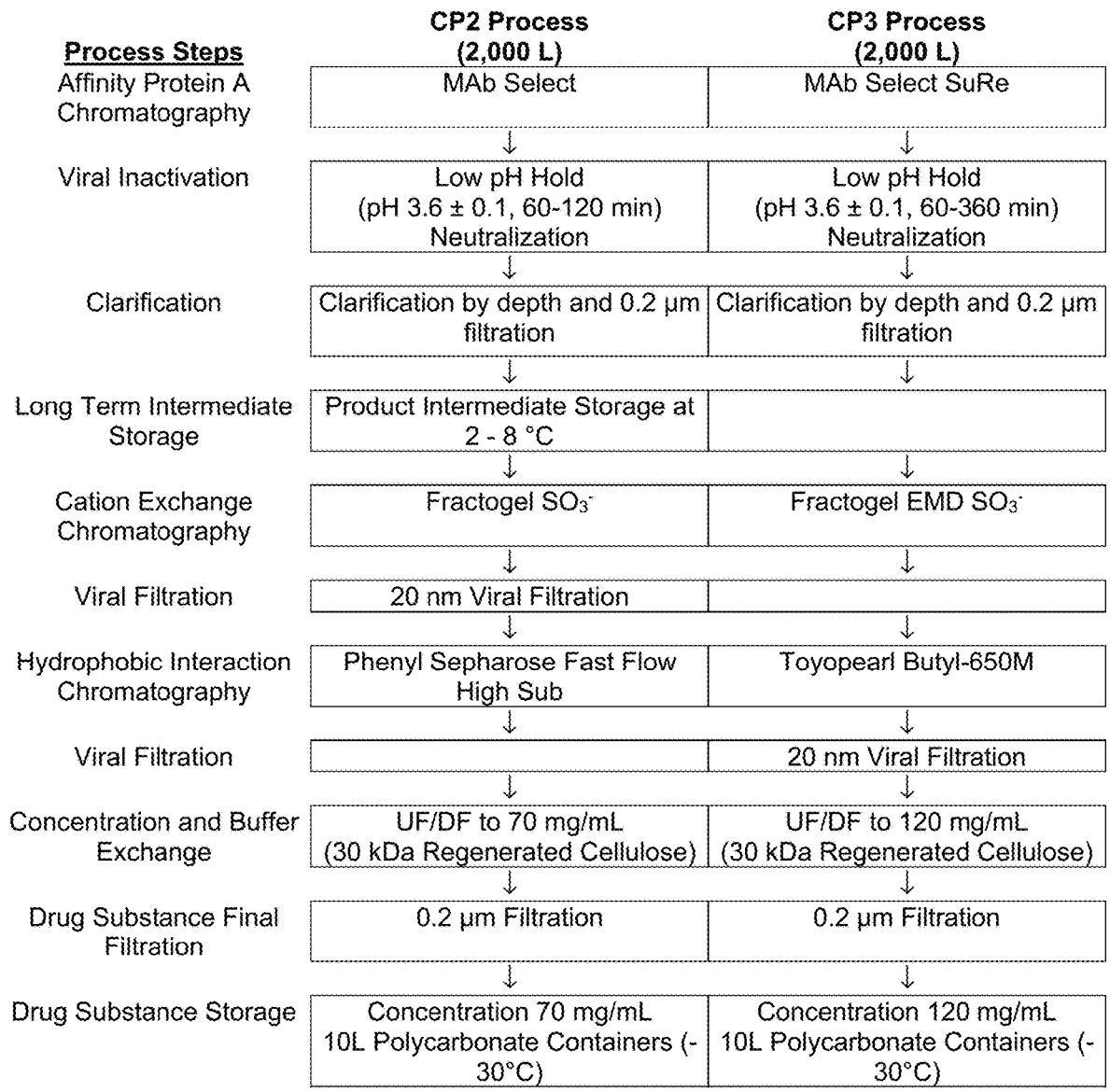
FIG. 14 is a purification flowchart for denosumab CP2 and CP3 processes.

A process flow diagram comparing the CP2 purification process and the CP3 purification process is shown in FIG. 14. Both processes contained the same basic type of unit operations but the operating parameters for each unit operation, and the order of these unit operations, had been optimized for each process. This was due to the differences in cell line in upstream performance parameters.

The first unit operation in both processes was a protein A affinity chromatography step performed on the clarified harvest. The protein A chromatography step was the primary purification stage using the specific high-affinity interaction between immobilized protein A ligand and the Fc region of denosumab to capture denosumab. The second unit operation in both processes was a low pH viral inactivation stage, which was designed to inactivate enveloped viruses.

The CP2 process then used 2-(N-morpholino)-ethanesulfonic acid (MES) and tris solutions to neutralize the product pool to pH 6.5 before a two-stage filtration. The CP3 process used a tri-sodium citrate solution to neutralize the product pool to a pH of 5.2 before a two-stage filtration. At this stage, the CP2 process could be held at 2-8° C. for long-term storage until it is requisitioned for further processing. The CP3 process could be held for 5 days at room temperature.

The second chromatography step, and third unit operation, in both processes was cation exchange (CEX). The operating conditions for each process were similar. The next two unit operations for the processes were the viral filtration and hydrophobic interaction chromatography (HIC) stages. The final unit operation for both processes was the ultrafiltration and diafiltration (UF/DF) to exchange the purified denosumab into formulation buffer. For CP2 the final drug substance concentration was 70 mg/mL. For CP3 the final drug substance concentration is 120 mg/mL.

As summarized in FIG. 14, the CP3 process improved the yield of denosumab production.

Example 3: Glycan Mapping of Denosumab Produced by CP2 Process

The glycosylation of denosumab comprises oligosaccharide structures occupying the single N-linked site at asparagine 298 on the heavy chains.

3.1 Glycan Occupancy

Occupancy of the N-glycosylation site at Asn-298 was determined from the Lys-C peptide map of denosumab following incubation with PNGaseF. Mass spectrometric analysis demonstrated the absence of ions corresponding to the glycosylated peptide after PNGaseF treatment, confirming complete removal of the N-glycans. Peptides that lacked glycosylation at Asn-298 were resolved as aglycosylated peptides; peptides with glycans at Asn-298 that were removed by PNGaseF were resolved as deglycosylated peptides. Identification and quantitation of the aglycosylated and deglycosylated peptides in the map were established by reconstruction of extracted ion chromatograms (EICs) of the +2 to +5 charge states for both peptides. Only the monoisotopic peaks for each charge state of the 2 peptides were used to reconstruct the EICs.

The percent occupancy of the N-glycosylation site was determined from the absolute peak areas of the EIC traces for the aglycosylated and deglycosylated peptides. Percent occupancy was calculated using the following equation:

$$\% \text{ occupancy} = 100\% - \left[\frac{area_{aglycosylated}}{area_{aglycosylated} + area_{deglycosylated}} \times 100\%\right]$$

The calculation assumed that the ionization efficiency of the aglycosylated and deglycosylated species were equivalent; in practice, given that the aglycosylated peptide contains an Asn residue whereas the deglycosylated peptide contains a negatively charged Asp residue at position 298, the ionization efficiency of the aglycosylated species is likely slightly higher than the deglycosylated species. Accordingly, the proportion of aglycosylated peptide was probably over-reported. The site occupancy of glycosylation at Asn-298 was approximately 99.7%. The level of aglycosylated form at Asn-298 was determined to be approximately 0.3% by Lys-C peptide map coupled with mass spectrometry.

Based on mass data from peptide mapping studies across the entire sequence, there is no evidence of any detectable levels of additional N-linked glycosylation, or O-linked glycosylation.

3.2 Mass Analysis of N-Linked Glycans and O-Linked Glycans

N-linked glycans were characterized by oligosaccharide mapping, mass spectrometry, and exoglycosidase sequencing. The oligosaccharide mapping involved release of N-glycans from the protein through hydrolysis using endoglycosidase PNGase-F. The reducing termini of the released glycans were then labeled through reductive amination with a fluorescent tag (2-aminobenzamide, 2-AB), and the labeled glycans were separated by high performance anion exchange chromatography (HPAEC), with fluorescence detection.

Each glycan species in the semi-preparative HPAEC profile was collected for mass spectrometric analysis. Each peak was re-injected onto an analytical column to verify the purity of the fractions (greater than 90% for most fractions). The purified fractions were then analyzed by matrix assisted laser desorption/ionization time of flight mass spectrometry (MALDI-TOF MS) to elucidate the glycan structures based on the observed masses.

The assigned glycan structure for each fraction (see FIG. 1), and the theoretical mass based on the empirical formula versus the observed mass, are shown in Table 3. The observed masses were all within 1,000 ppm of the theoretical masses, which is within experimental precision. The exact structures of the minor species (peaks 1, 15, 16, 17, and 18) were not identified due to their low abundance and insufficient ionization properties under the analysis conditions.

TABLE 5

Masses for Proposed Glycan Structures

| Peak [a] | Observed Mass (Da) [b] | Theoretical Mass (Da) [c] | Name and Empirical Formula | Relative % of Total Glycan |
|---|---|---|---|---|
| 2 | 1,379.1 | 1,378.3 | A1F-G0 $C_{55}O_{35}N_5H_{87}$ | 2.3% |
| 3 | 1,581.6 | 1,581.5 | A2F-G0 $C_{63}O_{40}N_6H_{100}$ | 58.6% |
| 4 | 1,233.3 | 1,232.2 | A1-G0 $C_{49}O_{31}N_5H_{77}$ | 2.4% |
| 5 | 1,743.3 | 1,743.6 | A2F-G1 $C_{69}O_{45}N_6H_{110}$ | 17.8% |
| 6a | 1,436.0 | 1,435.3 | A2-G0 $C_{57}O_{36}N_6H_{90}$ | 5.1% (sum of peaks 6a and 6b) |
| 6b | 1,395.0 | 1,394.3 | A1-G1 $C_{57}O_{36}N_5H_{87}$ | |
| 7 | 1,904.9 | 1,905.8 | A2F-G2 $C_{75}O_{50}N_6H_{120}$ | 1.8% |
| 8 | 1,354.1 | 1,353.2 | Man 5 $C_{53}O_{36}N_4H_{84}$ | 8.4% |
| 9a | 1,597.7 | 1,597.5 | A2-G1 $C_{63}O_{41}N_6H_{100}$ | 1.2% (sum of peaks 9a-9c) |
| 9b | 1,556.8 | 1,556.4 | Man 5-GlcNAc $C_{61}O_{41}N_5H_{97}$ | |
| 9c | 1,822.2 | 1,823.7 | Man 7-Fuc $C_{61}O_{41}N_5H_{97}$ | |
| 10 | 1,515.8 | 1,515.4 | Man 6 $C_{59}O_{41}N_4H_{94}$ | |
| 11 | 1,556.7 | 1,556.4 | Man 5-GlcNAc $C_{61}O_{41}N_5H_{97}$ | 1.6% (sum of peaks 10-14) |
| 12 | 1,719.3 | 1,718.6 | Man 6-GlNAc $C_{67}O_{46}N_5H_{107}$ | |
| 13 | 1,677.4 | 1,677.5 | Man 7 $C_{67}O_{46}N_5H_{107}$ | |
| 14 | 1,839.4 | 1,839.7 | Man 8 $C_{71}O_{51}N_4H_{114}$ | |

[a] Peaks 1, 15, 16, 17, and 18 were not identified by mass spectrometric analysis.
[b] Observed mass assumes exclusion of Na$^+$ adduct (22.99 Da) from the observed m/z.
[c] Theoretical mass is based on the empirical formula and includes glycan and 2-AB label (net mass of 118.14 Da).

The major species present in the N-glycan profile were biantennary structures with varying degrees of terminal galactosylation (~85%), as expected for CHO-derived antibodies. The next most prevalent species were high mannose species (~10%) with the majority of this subset being mannose 5 (8.1%). Monoantennary structures were also found in the N-glycan profile (peaks 2 and 4, 3.7%). The ratio of fucosylated to non-fucosylated biantennary forms was approximately 9:1.

The structures of the predominant N-linked oligosaccharides (peaks 2 to 9 in Table 3) were further confirmed by enzymatic release using exoglycosidases; α-(2-3, 6, 8, 9) sialidase, β-(1-4) galactosidase, β-(1-2, 3, 4, 6) glucosaminidase, and α-(1-2, 3, 4, 6) fucosidase.

The glycan profiles in the control sample and the sample were treated with α-(2-3, 6, 8, 9) sialidase for cleavage of sialic acid. None of the eight predominant species were affected by sialidase treatment, demonstrating that those predominant species are not sialylated glycans. The profile from the digestion with a combination of the α-sialidase and β-(1-4) galactosidase, which specifically cleave R-(1-4) linked terminal galactose residues, was also analyzed. Three peaks (A2F-G1, A2F-G2, A2-G1) listed in Table 3 had proposed structures containing terminal galactose(s). After treatment with β-(1-4) galactosidase, these peaks were absent, confirming the presence of terminal β-(1-4) linked galactose residues in those 3 peaks.

The profile from the digestion with β-(1-2, 3, 4, 6) glucosaminidase, an enzyme specific for cleavage of terminal GlcNAc residues, in addition to a combination of the α-sialidase and β-galactosidase described previously, was also analyzed. After sequential digestion with sialidase and galactosidase, there were four dominant glycan species listed in Table 3 with proposed structures containing a terminal GlcNAc: A1F-G0, A2G-G0, A1-G0, and A2-G0. After treatment with β-(1-2, 3, 4, 6) glucosaminidase, these peaks were absent, confirming the presence of terminal GlcNAc in those four peaks.

Following digestion with the mixture of α-sialidase, β-galactosidase and β-glucosaminidase, there were 3 peaks remaining in the profile. The peak eluting at 10 minutes was collected and analyzed by MALDI-TOF MS. The observed mass was 1,198.7 Da, agreeing with the expected mass of 2-AB labelled fucosylated mannose 3 (1,198.1 Da), the fucosylated mannose-3 structure resulting from the removal of galactose and N-acetyl galactosamine from the fucosylated biantennary structures by the enzymatic treatment described above.

The profile from the digestion with α-(1-2, 3, 4, 6) fucosidase, an enzyme specific for cleavage of fucose residues linked to the trimannosyl core, in addition to a mixture of the α-sialidase, β-galactosidase, and β-glucosaminidase described previously, was also analyzed. Following digestion with α-(1-2, 3, 4, 6) fucosidase, the peak eluting at 10 minutes was no longer present in the profile and there was a significant increase in the intensity of the peak eluting at 16 minutes. This result confirmed that the peak eluting at 10 minutes was fucosylated mannose 3 and the peak eluting at 16 min was non-fucosylated mannose 3.

In addition to the exoglycosidase treatment described above, the glycan pool was digested with α-(1-3, 4, 6) galactosidase to identify any potentially immunogenic terminal α-(1-3) galactose residues in the denosumab glycan moiety. Following digestion with α-galactosidase, the HPAEC glycan profile of denosumab was compared to a control sample. To account for any subtle variations in the profile, triplicate injections of the control and digested sample were performed. The overlays of the chromatograms from the triplicate injections showed no change in the glycan profile, indicating no detectable quantities of terminal α-(1-3) galactose residues.

Based on the exoglycosidase treatment studies described above, the identification of 8 predominant N-linked oligosaccharides by HPAEC/MALDI-TOF MS (Table 3) was confirmed.

Comprehensive mass spectrometric-based sequence studies were conducted to characterize the primary structure of denosumab. The results confirmed that there is no evidence of any O-linked glycosylation in denosumab.

3.3 Glycation

Non-enzymatic glycation was observed in the heavy chain adjacent to the variable region at Lys-98. Modifications were specific to the heavy chain. Glycation contributes to charge heterogeneity, because it causes a loss of a positive charge (Lys), resulting in an acidic variant and a mass increase of 162 Da.

Figure 2:
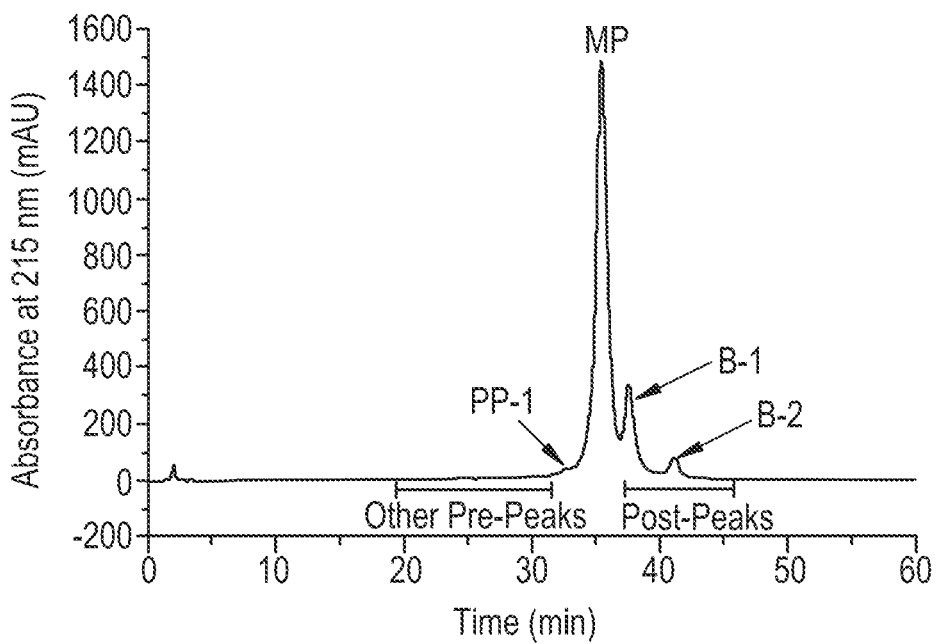
FIG. 2 is a graph showing CE-HPLC profile of denosumab samples from CP2 process for the analysis of glycation.

Charge heterogeneity of denosumab was assessed by CE-HPLC. The CE-HPLC profile of denosumab contained 4 distinct peaks: Pre-peak 1 (PP-1), main peak (MP), basic peak 1 (B-1) and basic peak 2 (B-2) (FIG. 2A). The purified peaks were characterized by various analytical techniques including orthogonal charge based techniques and primary structure techniques to elucidate the nature and location of charge modifications. PP-1 contained glycated heavy chain at Lys-98. Purified PP-1 was analyzed with Lys-C peptide mapping. A peptide mass consistent with a glycation modification at Lys-98 was observed in the peak eluting at 87-minute retention time.

To further confirm the peak identity as a glycation modification, a forced glycated sample was prepared and run by Lys-C peptide mapping. Forced glycation was accomplished by mixing denosumab with a buffered glucose solution and incubating overnight at 37° C. A control sample was also prepared in parallel where the glucose was omitted from the preparation. An elevated level of a peptide eluting at 87 minutes was found in the purified PP-1 sample as well as in the forced glycated sample, which further confirms the presence of the glycated variant in the purified PP-1 sample.

The putative glycated peptide peak and the native peptide peak were characterized by electrospray MS analysis in-situ during elution of the peptide map. The measured monoisotopic mass of the peptide eluting at 88 minutes was 5,572.48 Da, from the zoom scan of the 3+ ion. The measured monoisotopic mass from the 3+ ion of the glycated peptide eluting at 87.02 minutes was 5,734.54 Da (5,572.48+162.06 Da), consistent with the expected addition of a +162 mass for a glycation. The size profile of PP-1 was examined by SE-HPLC and rCE-SDS. PP-1 was determined to contain native monomer by SE-HPLC. Reduced CE-SDS revealed the presence of a molecular weight species slightly larger than heavy chain in the post-heavy chain region.

Denosumab produced by CP2 process has about 10% glycation (analysis by deglycosylated intact mass), a modification presumably due to the glucose present in the production cell culture fluid.

To investigate the biological impact of the charge variants in PP-1, this fraction was analyzed for potency using the HTRF receptor-ligand binding, Reporter Gene, and TRAP activity assays (Table 4). A forced glycated sample was included in the analysis. Both PP-1 and forced glycated drug substance exhibited full potency.

TABLE 6

Potency Assay Results for PP-1 and Forced Glycated Sample

| Peak | HTRF | | Reporter Gene | | TRAP | |
| --- | --- | --- | --- | --- | --- | --- |
| | % Relative Potency | % CV | % Relative Potency | % CV | % Relative Potency | % CV |
| PP-1 | *93 | 7 | 98 | 12 | 97 | 2 |
| Forced Glycated | *94 | 4 | 91 | 6 | 99 | 4 |

Note:
3 determinations for HTRF, 5 determinations for other assays

Example 3: Comparison of N-Glycan Profiles of Denosumab Produced by CP2 and CP3 Processes Glycans were removed by treatment with N-glycanase with subsequent labeling by the fluorescent compound 2-aminobenzamide. The glycan species were separated using high pH anion exchange chromatography, and quantified using fluorescence detection (excitation X=330 nm and the emission X=420 nm). The glycan peaks were then quantified. Overlays of the N-glycan profile for all tested samples, as well as the reference standard, are presented in FIG. 3A. Relative distributions of the N-glycans in denosumab from CP3 and CP2 lots are shown in FIG. 3B.

Figure 3A:
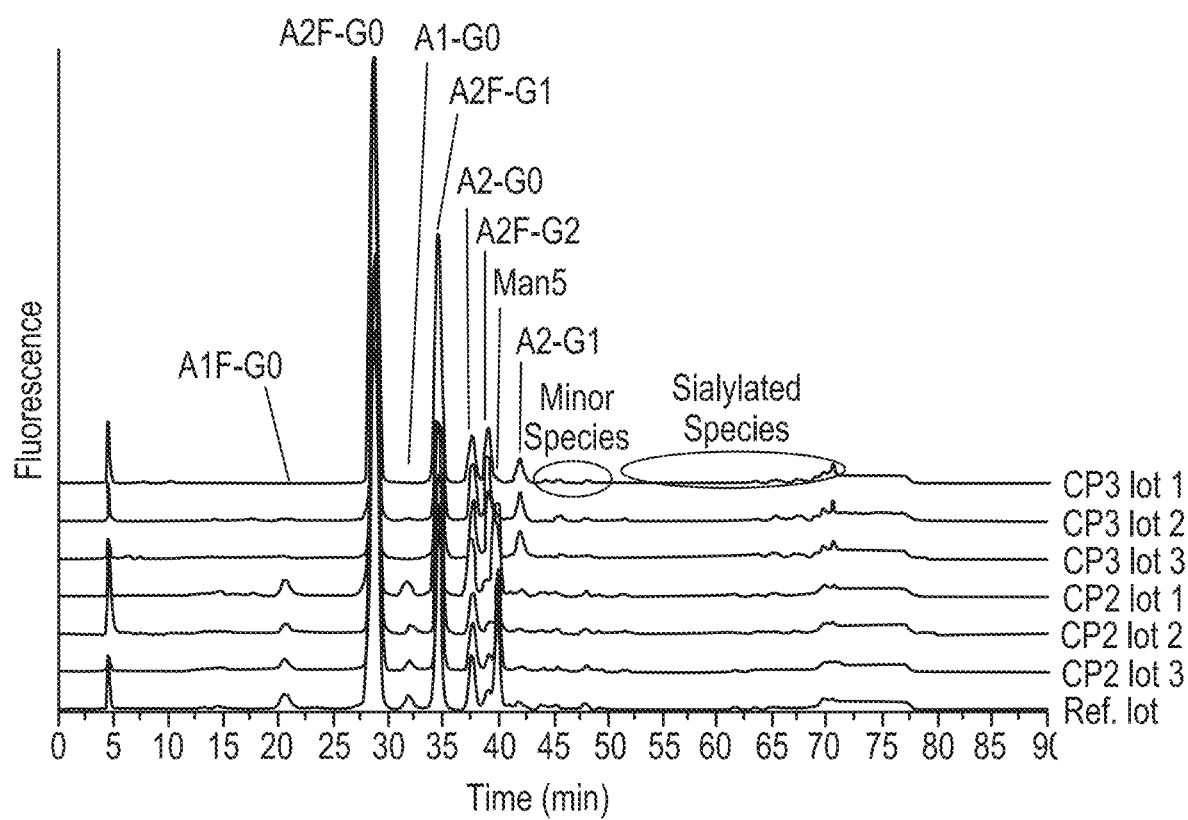
FIG. 3A is a graph showing the N-glycan profiles of samples from CP2 and CP3 processes, as well as the reference standard.

As shown in the glycan map profiles in FIG. 3A, both CP3 and CP2 lots contained eight named glycan species and two named groups. Therefore, the overall glycan map profiles show similar patterns of glycans present in both CP3 and CP2 lots. No new glycoforms were observed in the profile of CP3 lots. However, there were differences in the distribution of the glycans between CP3 and CP2 lots. Specifically, the CP3 lots were more galactosylated with a corresponding increase in the degree of sialylation. In addition, CP3 lots contained less Man-5 and monoantennary structures (FIG. 3B). Table 5 summarizes glycan map historical data.

Note that the "preferred" ranges provided in Table 5 (last column) for CP2 and CP3 are considered clinical range (which are typically based on patient exposure during clinical trials). Clinical ranges are in general wider, and less stringent than the commercial ranges (which are generated from commercial lots). Also, these preferred ranges should not be simply taken as determinative criteria for biosimilarity assessment. For purpose of biosimilarity, different or narrower ranges of various glycan contents might be needed.

TABLE 7

Glycan Map Historical Data

| Parameter | Ref. lots | CP2-1 | CP2-2 | CP3 | preferred |
|---|---|---|---|---|---|
| A2F-G0 | 48.9-51.2 | 54.9-64.7 | 56.6-58.6 | 40.7-42.6 | 48-70% |
| A2F-G1 | 27.8-29.5 | 14.5-19.2 | 18.8-20.6 | 35.6-35.8 | 13-26% |
| A2-G0 | 5.0-6.7 | 5.0-5.8 | 4.5-5.8 | 6.8-7.1 | |
| A2F-G2 | 4.2-4.5 | 1.2-2.0 | 1.6-2.2 | 7.1-7.5 | |
| High Mannose (Man 5) | 2.4-4.0 | 6.6-10.6 | 8.0-9.3 | 0.7 | 2-14% |
| A2-G1 | 2.0-2.2 | 0.7-0.9 | 0.9-1.4 | 3.6-4.0 | |
| % Sialylated | 1.3-1.8 | 0.9-1.4 | 0.9-1.3 | 2.0-2.1 | |

There were no new carbohydrate species present in denosumab manufactured using the CP3 process as compared to the CP2 process, but the distribution of the species was slightly different. Studies performed using denosumab showed that glycosylation differences do not affect binding of denosumab to RANK ligand. Deglycosylated denosumab also has full potency by all 3 bioassays.

Example 4: PK/PD Studies of Denosumab Produced by CP3 Process 4.1 Study Design

An open-label, randomized, single-dose, parallel group study in healthy volunteers was conducted. Subjects were randomized (1:1 allocation ratio) to receive either a single 60-mg SC dose of denosumab manufactured utilizing the CP3 process (treatment A) or a single 60-mg SC dose of denosumab manufactured utilizing the CP2 process (treatment B). Blood samples were collected for PK and PD analysis at specified time points from before denosumab administration until the end of the study. Subjects completed the study on day 113 after all study procedures were performed A total of 115 subjects were enrolled in the study. A total of 112 subjects (97%) completed the study. Three subjects (3%) did not complete the study. 57 subjects received CP3-denosumab (55 completed the study), and 58 subjects received CP2-denosumab (57 completed the study).

Serum concentrations of denosumab were measured using a validated enzyme-linked immunosorbent assay (ELISA). The lower limit of quantification (LLOQ) of the assay was 20 ng/mL. Briefly, recombinant human receptor activator of NF-κB ligand (RANKL) was coated onto polystyrene 96-well plates and used as a capture reagent. Standards (STD) and quality controls (QC) were prepared by spiking denosumab into 100% human serum. Standards, quality controls, study samples and blank were loaded into the wells after 1:10 pre-treatment with assay diluent (1×PBS with 1% BSA, 1M NaCl, 0.5% Tween 20). Denosumab in STDs, QCs and study samples was captured by the immobilized recombinant human RANKL. After a wash step, a biotinylated rabbit anti-denosumab detection antibody was added. After another wash step, a streptavidin conjugated to horseradish peroxidase was added to bind to the complex. After a final wash step, a tetramethylbenzidine (TMB)-peroxidase substrate was added to the plate. The color development was stopped and the intensity of the color (optical density, OD) was measured at 450 nm with reference to 650 nm. The conversion of OD units for the quality controls and study samples to concentration was achieved through a computer software mediated comparison to a standard curve on the same run, which was regressed according to a logistic auto-estimate regression model with a weighting factor of 1/Y using Watson LIMS version 7.0.0.01 data reduction package.

Concentrations of serum C-telopeptide (CTX1) were measured by a validated Serum CrossLaps® ELISA. The LLOQ was 0.049 ng/mL. Briefly, a Serum CrossLap® ELISA is based on 2 highly specific monoclonal antibodies against the amino acid sequence of EKAHD-β-GGR, where the aspartic acid residue (D) is β-isomerized. In order to obtain a specific signal in the Serum CrossLaps® ELISA, 2 chains of EKAHD-β-GGR must be cross-linked. Standards (STDs), Quality Controls (QCs), Sample Controls (SC), blank, and study samples were added into a microtiter plate coated with streptavidin, followed by addition of a mixture of a biotinylated antibody and a horseradish peroxidase (HRP)-conjugated antibody. CTX1 present in the STD, QC, SC, or sample would form a complex with the biotinylated antibody and HRP-conjugated antibody. This complex bound to the streptavidin-coated microtiter plate via the biotinylated antibody. Following incubation at ambient room temperature, the plate was washed. A tetramethylbenzidine (TMB) solution was added to the plate. The color development was stopped and the intensity of the color (optical density, OD) was measured at 450 nm with 650 nm as reference. The conversion of OD units to concentrations was achieved through a computer software mediated comparison to a standard curve assayed on the same plate and regressed according to a 4-parameter logistic (auto estimate) regression model with a weighting factor of $1/Y^2$ using Watson version 7.0.0.01 data reduction package 4.2 Pharmacokinetic Analyses Serum denosumab concentration-time data were analyzed by noncompartmental methods using WinNonlin Enterprise v 5.1.1 within PKS v3.1a, build 200610240912 (Pharsight Corporation, Mountain View, CA). Figures were created using SigmaPlot v10 build 10.0.1.2 (SPSS Science, Chicago, IL). Nominal sampling times were used in the analysis unless the actual time deviation was equal to or greater than 10%, in which case the actual time was used. Denosumab serum concentrations below the lower limit of quantification (LLOQ) of 20 ng/mL were set to zero in the noncompartmental analysis and for the calculation of summary statistics. Summary statistics were calculated using nonrounded values.

The maximum observed serum denosumab concentration (Cmax) after dosing was identified by inspection of the data. The corresponding time of Cmax (tmax) was also recorded.

The area under the concentration-time curve from time 0 to 16 weeks (AUC0-16 weeks) was calculated by the linear-log trapezoidal method, which applies the linear trapezoidal rule up to Cmax and then the log trapezoidal rule for the remainder of the curve.

Figure 4A:
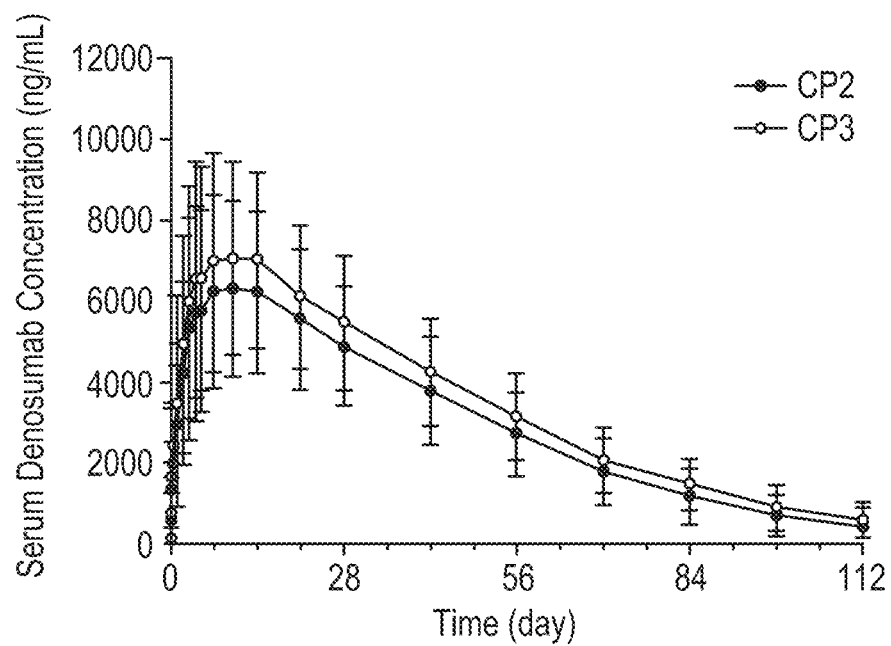
FIGS. 4A-4E summarize the PK/PD profiles of denosumab produced by CP2 and CP3 processes.
Figure 4B:
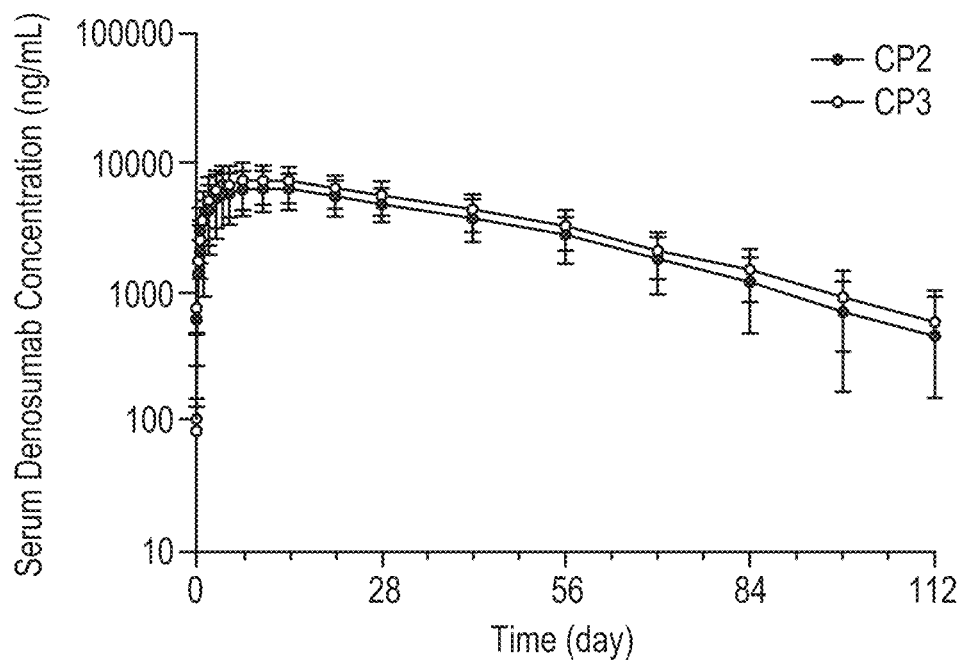

Mean serum denosumab concentration-time profiles for denosumab CP3 and CP2 are shown in linear scale and semi-log scale in FIGS. 4A-4B respectively. Assessment of the profiles on a linear scale (FIG. 4A) indicates that sampling to 16 weeks (112 days) captured a large majority of exposure for both treatments. Denosumab produced by the CP3 process showed. As compared to Denosumab produced by CP2 process, CP3-denosumab had more gal species, less high mannose species.

As shown in FIGS. 4A and 4B, denosumab produced by CP3 process showed higher serum half-life in patients (10% longer half-life on average), suggesting slower clearance rate. The mean half-life of CP2-produced denosumab is about 25.8 (6.5) days (median=25.0); and the mean half-life of CP2-produced denosumab is about 28.3 (6.5) days (median=27.4). Geometric mean $AUC_{0-16}$ weeks and $C_{max}$ values for CP3 were greater than values for CP2 by approximately 16% and 14%, respectively (Tables 8.1 and 8.2).

Figure 4C:
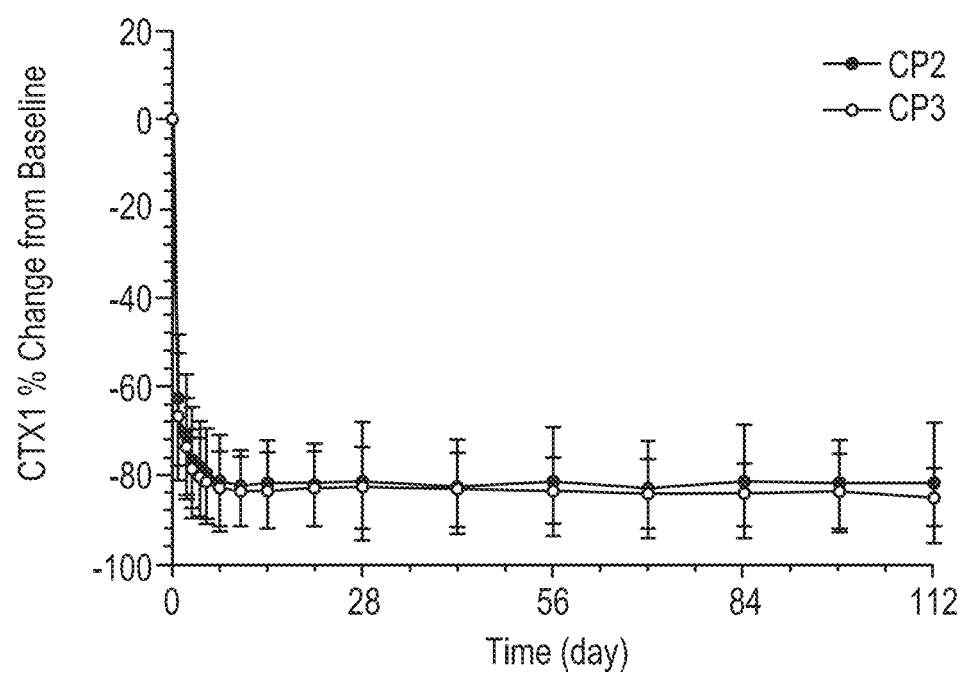
Figure 4D:
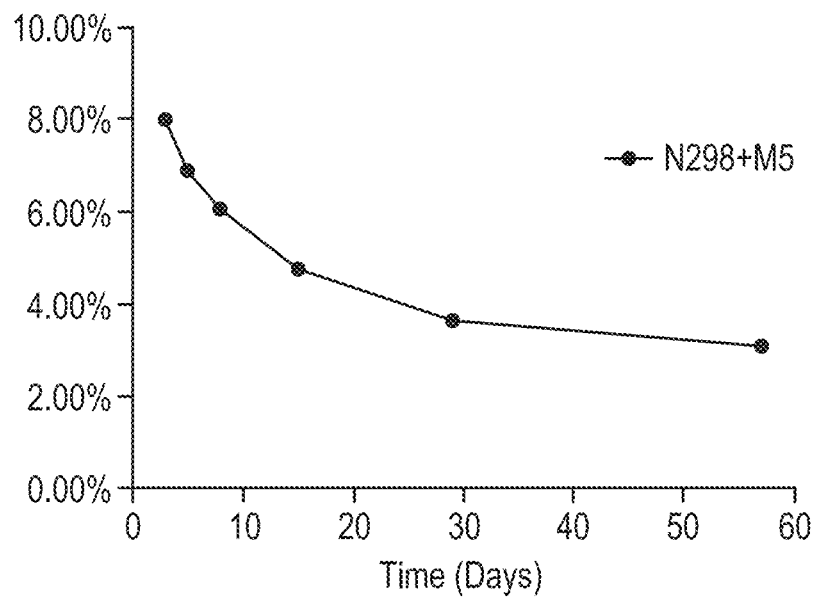
Figure 4E:
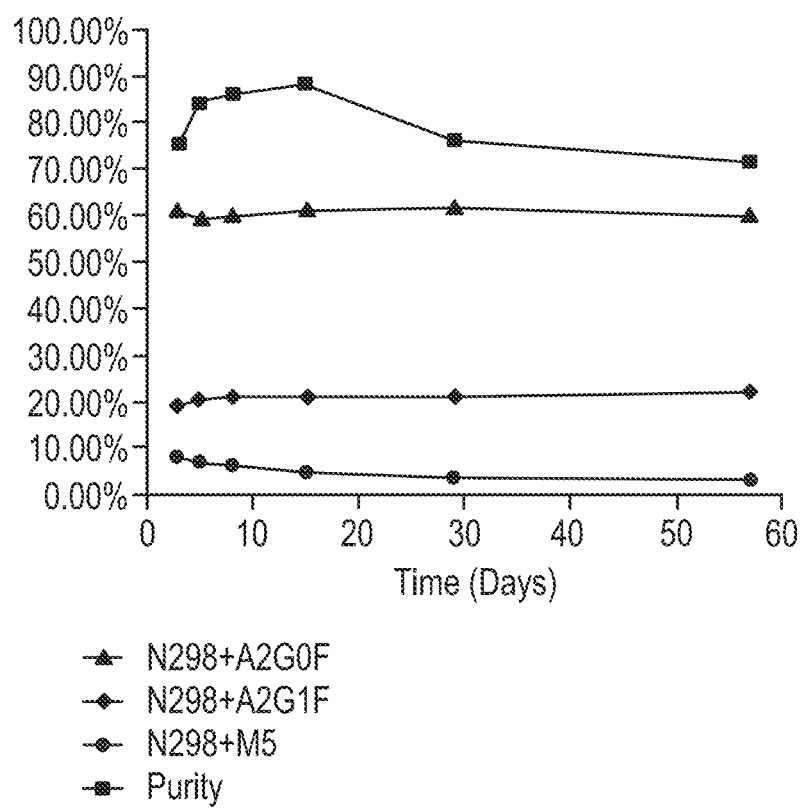

As shown in FIGS. 4D and 4E, the increased half-life of CP3-denosumab was due to the faster clearance of Man-5 species. Denosumab molecules comprising Man-5 were preferentially cleared, resulting in the overall decrease of Man-5 level overtime. In contrast, the level of gal species remained largely constant during the same period of time. This demonstrates that denosumab molecules with Man-5 was preferentially cleared in serum, as compared to denosumab without Man-5, resulting in an overall decrease in Man-5 level. At the beginning of the study, about 8% of the denosumab molecules comprised Man-5; around day 60, less than 4% denosumab molecules comprised Man-5.

TABLE 8.1

PK/PD summary of CP3-denosumab

| | Parameter | PE (90% CI)* |
|---|---|---|
| PK | $C_{max}$ | 1.137 (1.016-1.273) |
| | $AUC_{0-112\ days}$ | 1.162 (1.032-1.308) |
| PD | $I_{max}$ | 1.014 (0.990-1.039) |
| | $AUEC_{0-112\ days}$ | 1.027 (0.985-1.070) |

*Point estimate (90% confidence interval) for the ratio CP3/CP2

TABLE 8.2

Mean (SD) serum denosumab pharmacokinetic parameter estimates following 60 mg SC administration of denosumab CP3 or CP2 to healthy volunteers

| | Arithmetic Mean (SD)[a] | | Geometric Mean[a] | | |
|---|---|---|---|---|---|
| Parameter | CP2 (N = 58[c]) | CP3 (N = 56[c]) | CP2 (N = 58[c]) | CP3 (N = 56[c]) | PE[b] (90% CI) |
| $AUC_{0-16\ weeks}$ (μg*day/mL) | 330 (120) | 380 (130) | 308 | 358 | 1.16 (1.03, 1.31) |
| $C_{max}$ (μg/mL) | 6.81 (2.43) | 7.70 (2.54) | 6.39 | 7.26 | 1.14 (1.02, 1.27) |
| $t_{max}$ (day) | 10 (2.3-28) | 10 (1.0-21) | — | — | — |

$AUC_{0-16weeks}$ = area under serum denosumab concentration-time curve from 0 to 16 weeks
$C_{max}$ = maximum observed concentration
$t_{max}$ = time at which $C_{max}$ is observed and presented as median (range)
[a]Mean values rounded to 3 significant figures (2 for $t_{max}$), SD are reported to the same precision as its respective mean; all calculations were performed using unrounded values
[b]Point Estimate (PE) and 90% confidence intervals (CI) are for the ratio (CP3/CP2) for log transformed $AUC_{0-16\ weeks}$ and $C_{max}$
[c]N = 56 and 55 for CP2 and CP3 $AUC_{0-16\ weeks}$ values, respectively 4.3 Pharmacodynamic Analyses The baseline serum CTX1 concentration was calculated as the median of the concentrations determined in 3 samples obtained prior to dosing of denosumab. The percent change from baseline was calculated as the post-dose measurement minus the baseline measurement, divided by the baseline measurement, multiplied by 100%. Post-baseline CTX1 concentrations below the LLOQ of the analytical method were assigned the value of the LLOQ (0.049 ng/mL) for calculation of the percent change from baseline. All calculations were performed using nonrounded values. Nominal sampling times were used in the analysis unless the actual time deviation was equal to or greater than 10%, in which case the actual time was used. Figures were created using SigmaPlot v10 build 10.0.1.2 (SPSS Science, Chicago, IL).

The % inhibition of CTX1 after dosing was calculated as the % change from baseline multiplied by −1. Individual % inhibition of CTX1 versus time data were analyzed by noncompartmental methods using WinNonlin Enterprise v 5.1.1 (Pharsight Corporation, Mountain View, CA). The maximum observed % inhibition of CTX1 (Imax) and the time it occurred (tmax, CTX1) were recorded. The area under the effect (% inhibition of CTX1 versus time) curve from time zero to sixteen weeks ($AUEC_{0-16}$ weeks) was calculated by the linear-log trapezoidal method, which applies the linear trapezoidal rule up to Imax and then the log trapezoidal rule for the remainder of the curve.

At baseline, the mean (±SD) serum concentration of CTX1 was 0.555 (±0.288) ng/mL for the CP3 group and 0.488 (±0.251) ng/mL for the CP2 group. Mean (±SD) percent change from baseline CTX1 versus time profiles for the 2 treatments are provided in FIG. 4C. The mean percent change from baseline CTX1 profiles for the 2 treatments were essentially superposable. Geometric mean $AUEC_{0-16}$ weeks and Imax values differed by ≤3% between treatments (Tables 8.1 and 8.3). The 90% CI for the ratio of the geometric means for $AUEC_{0-16}$ weeks and Imax were within the range 0.80 to 1.25. Although median tmax, CTX1 values differed between CP3 and CP2 (25 versus 12 days), it is apparent from the mean CTX1 percent change from baseline profiles (FIG. 10-3) that the overall extent of inhibition was relatively constant from days 7 through 112 for both treatments.

TABLE 8.3

Mean (SD) serum C-Telopeptide parameter sstimates following 60 mg SC administration of denosumab CP3 or CP2 to healthy volunteers

| | Arithmetic Mean (SD)[a] | | Geometric Mean[a] | | |
|---|---|---|---|---|---|
| Parameter | CP2 (N = 58[c]) | CP3 (N = 56[c]) | CP2 (N = 58[c]) | CP3 (N = 56[c]) | PE[b] (90% CI) |
| $AUEC_{0-16\ weeks}$ (day* % inhibition) | 9120 (1210) | 9290 (810) | 9010 | 9250 | 1.03 (0.98, 1.07) |
| $I_{max}$ (% inhibition) | 85.9 (7.1) | 86.9 (5.5) | 85.5 | 86.7 | 1.01 (0.99, 1.04) |
| $t_{max,\ CTX1}$ (day) | 12 (2.0-110) | 25 (1.0-110) | — | — | — |

$AUEC_{0-16\ weeks}$ = area under the effect curve from time 0 to 16 weeks
$I_{max}$ = maximum observed % Inhibition
$t_{max,\ CTX1}$ = time at which $I_{max}$ was observed, expressed as median (range)
[a]Mean values rounded to 3 significant figures (2 for $t_{max}$), SD are reported to the same precision as its respective mean; all calculations were performed using unrounded values
[b]Point Estimate (PE) and 90% confidence intervals (CI) are for the ratio (CP3/CP2) for log transformed $AUEC_{0-16\ weeks}$ and $I_{max}$
[c]N = 56 and 55 for CP2 and CP3 $AUEC_{0-16\ weeks}$ values, respectively.

Example 5: Comparison of CP2 and CP4 Culturing Processes

A process flow diagram comparing the cell culture and harvest operations for the CP2 process versus the CP4 process is presented in FIG. 15. The CP4 cell culture expansion and production processes were based on the CS-9 CHO (25B12) parental cell line. The CP4 process utilized smaller production bioreactors operated in perfusion mode and exclusively utilizes single-use (disposable) cell culture expansion and production vessels. The CP2 and CP4 production culture processes were controlled at process-specific set-points optimized for each cell line. The media formulations and timing for nutrient feeds had been designed for optimal cell health and production. The CP4 production bioreactor used chemically defined media formulations, and was amplified with methotrexate (MTX). For both processes the thaw and initial expansion of the cell mass were performed in shaker flasks. Both processes used Dulbecco's Modified Eagle's Medium (DMEM)/F12-based media; however the formulations were different and had been optimized for the different cell lines.

For both processes, the expansion bioreactor stages were operated in batch mode, except the CP4 N−1 that was operated in fed-batch mode. During the expansion bioreactor phase the CP2 process used 4 stainless steel bioreactors whereas the CP4 process used 2 single-use bag (SUB) systems each with 2 stages. The first single-use system in the CP4 expansion process was a 2-stage 50 L culture bag with the temperature, pCO2, and overlay gas flow rates controlled to process-specific set points. The second single-use system in the CP4 expansion process was a 2-stage 500 L SUB with a nutrient feed on day 2 of the second stage (N−1). During the operation of all expansion bioreactors (CP2 and CP4 SUB stages), the pH, temperature, pressure, agitation, and dissolved oxygen were controlled to process-specific set-points.

The production bioreactors were operated under different modes. The CP2 process used a 16 kL stainless steel, fed-batch bioreactor, with feeds on days 3 and 9, and the culture was harvested on day 14. The CP4 process used a 2 kL SUB with 2 bolus feeds on days 3 and 6, perfusion was started on day 7 with a change in media on day 11, and the culture was harvested on day 18. The media change on day 11 reduced the glucose concentration and added galactose as an alternative carbohydrate source. This change was made such that the high mannose glycan profile from the CP4 process would be comparable to that of the CP2 process, as the high mannose glycan profile on monoclonal antibodies may have the potential to affect in vivo clearance. The perfusion separation technology used a membrane with a 30 kDa nominal pore size such that all components approximately greater than that size were retained in the bioreactor, including cells and product. All set points had been optimized for each cell line and production mode.

The CP2 production and feed media were based on a modified DMEM/F12 medium and contained soy hydrolysate. The CP4 production, feed, and perfusion media were chemically defined formulations and did not contain hydrolysates.

Example 6: Comparison of CP2 and CP4 Harvesting and Purification Processes

In both processes, after completion of the production phase, the bioreactor contents were chilled to target temperatures of 10 t 3° C. in CP2 and ≤12° C. in CP4. For the CP2 process the disc-stack centrifugation accomplished the primary separation of the production cells and cell debris from the culture medium. For the CP4 process the primary separation was accomplished using flocculation with polydiallyldimethylammonium chloride (PDADMAC) and polyethylene glycol (PEG) followed by settling. Both processes followed the primary separation with depth and membrane filtration. Additionally, the CP4 process utilized an air or oxygen sparge during the harvest processing.

Figure 16:
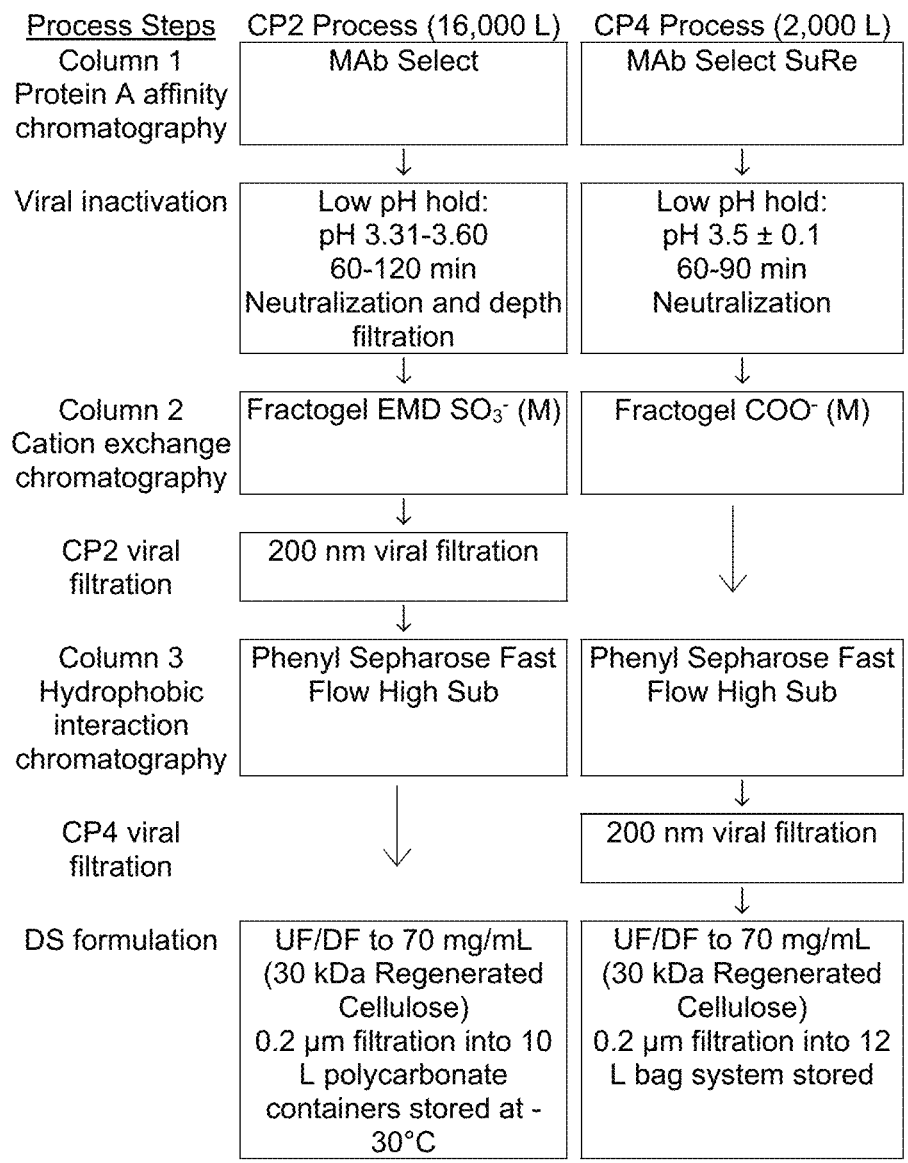
FIG. 16 is a flowchart for purification for the denosumab CP2 and CP4 processes.

A process flow diagram comparing the purification operations for the CP2 process and the CP4 process is presented in FIG. 16.

Both purification processes used the same basic unit operations: 2 dedicated viral removal/inactivation operations (low pH viral inactivation and 200 nm viral filtration), 3 chromatography operations (protein A affinity, cation exchange, and hydrophobic interaction), and an ultrafiltration (UF)/diafiltration (DF) operation to concentrate and buffer exchange denosumab into the final DS formulation. The operating parameters for each unit operation, and the order of these unit operations, had been optimized for each process. Additional differences included changes in chromatography resins, buffers, filter types, and areas and order of operations. These differences were due to the change in cell line and the higher cell concentrations that result from using a perfusion mode in the CP4 process production bioreactor.

The first unit operation was column 1, a protein A affinity chromatography step performed on the harvest filtrate. Column 1 was the primary purification stage, utilizing the specific high-affinity interaction between immobilized protein A and the Fc region of IgG type antibodies to capture denosumab. The CP4 process utilized MabSelect SuRe resin and the CP2 process utilized MabSelect resin. The second unit operation in both processes was a low pH viral inactivation step, which was the first of 2 dedicated operations to inactivate and clear viruses. Viral inactivation was achieved for the CP4 process at a pH of 3.5±0.1 for 60 to 90 minutes and for the CP2 process at a pH of 3.31-3.60 for 60 to 120 minutes, with the difference due to the change in host cell line and process.

At the end of the low pH incubation period in the CP4 process, the pH of the viral inactivation pool was adjusted to 5.0 with Tris base and the pool was then filtered through a 0.2 m polyethersulfone (PES) membrane filter. For the CP2 process, the pH of the pool was adjusted to 3.31-3.60 with sodium 1-(N-morpholino)-ethanesulfonic acid (MES) and Tris base and the pool was then clarified by a 2-stage filtration train. The difference in pH was due to the differences in operation of column 2.

The third unit operation in both processes was column 2, a cation exchange chromatography (CEX) step. This step removed impurities present in the filtered viral inactivation pool from the product stream using CEX resin. The CP4 process used Fractogel COO⁻ (M) resin and the CP2 process used Fractogel S03 (M) resin.

The next 2 unit operations for both processes were the viral filtration and hydrophobic interaction chromatography (HIC) stages; however, the sequence was reversed.

The next unit operation for both processes was the UF/DF to exchange the purified denosumab into formulation buffer. Both CP4 and CP2 product streams were diafiltered against 10 mM sodium acetate, 5% sorbitol at pH 4.80 to a final denosumab concentration of 70 mg/mL. No changes were made to the DS storage containers or storage conditions.

Example 7: Glycan Mapping of Denosumab Produced by CP4 Processes

7.1 N-Glycan Mapping of Denosumab Produced by CP4 Processes

Glycosylation was evaluated by mapping of the N-linked oligosaccharide structures. This procedure involved releasing the N-linked glycans from denosumab with PNGaseF treatment. The released glycans were labeled with 2-aminobenzoic acid (2-AA), and followed by hydrophilic interaction liquid chromatography (HILIC) with fluorescence detection. Eluted peaks were monitored with a fluorescence detector. Characterization of the denosumab N glycan map peaks was conducted by oligosaccharide mapping with mass spectrometry. The assigned glycan structure for each glycan and the theoretical mass based on the empirical formula versus the observed mass, are shown in Tables 2 and 5. The observed masses were all within the expected experimental precision.

TABLE 11

Composition of Major N-linked Glycans

| Oligosaccharide Name | Simplified Oligosaccharide Term | %$^a$ |
| --- | --- | --- |
| Asialo-, agalacto-, mono-antennary, core substituted with fucose | A1G0F | 3.2 |
| Asialo-, agalacto-, bi-antennary, core substituted with fucose | A2G0F | 60.8 |
| Asialo-, agalacto-, mono-antennary | A1G0 | 1.4 |
| Asialo-, mono-galactosylated bi-antennary, core substituted with fucose | A2G1F | 13.1 |
| Asialo-, agalacto-, bi-antennary | A2G0 | 6.3 |
| Asialo-, bi-galactosylated bi-antennary, core substituted with fucose | A2G2F | 0.9 |
| Mannose-5 | M5 | 7.8 |
| Asialo-, mono-galactosylated bi-antennary | A2G1 | 2.5 |

$^a$"%" refers to relative percentage, calculated according to HILIC peaks

Figure 5:
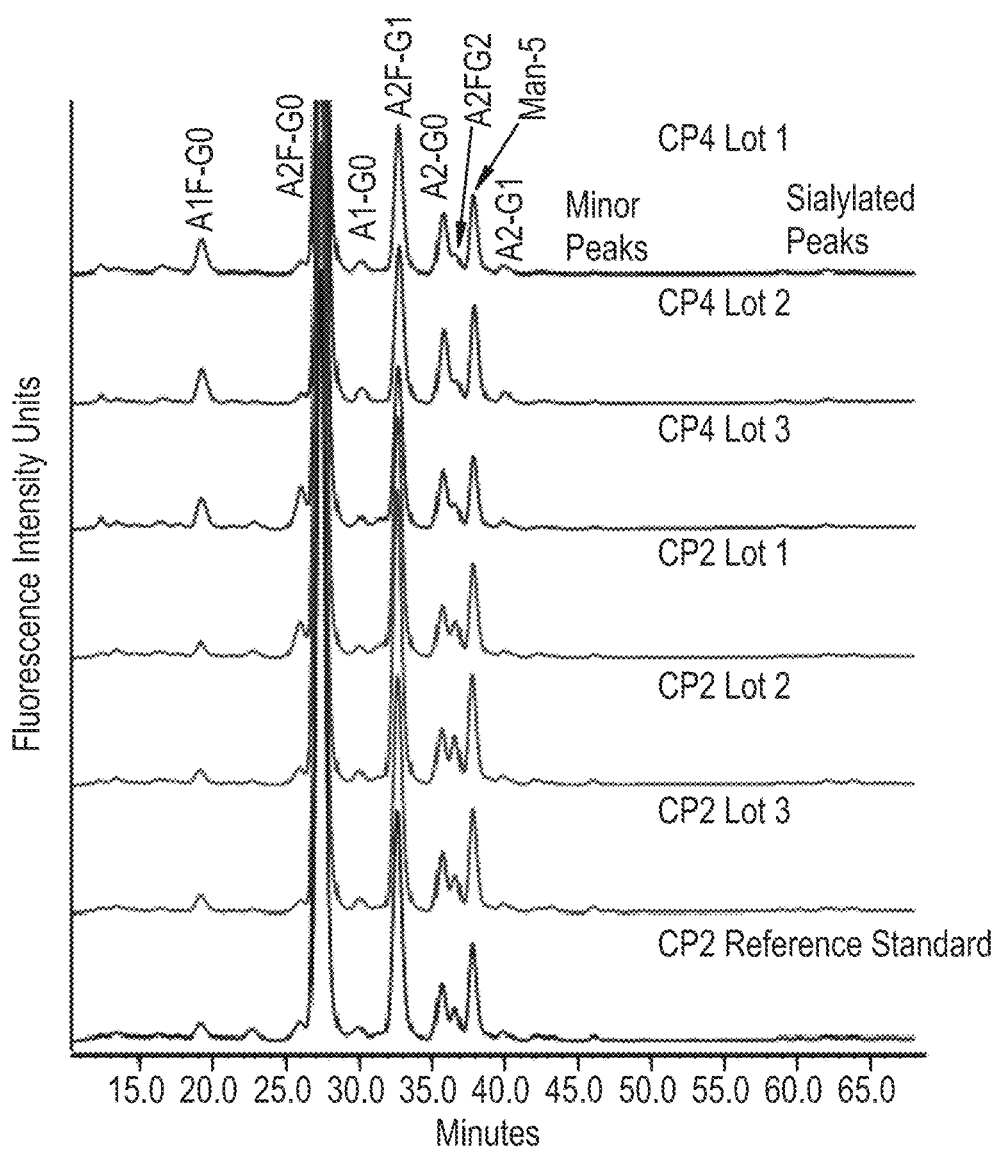
FIG. 5 shows the glycan map (HP-AEX) overlays. CP2-denosumab and CP4-denosumab showed similar N-glycan profiles.

The majority of the species were core fucosylated, complex biantennary structures with 0 or 1 terminal galactose with relatively low levels of afucosylated biantennary structures. The glycan population contained very low levels of sialylated species and hybrid type glycans, as well as ~8% high mannose glycans (predominantly as the mannose 5 structure). The percentages of denosumab N-linked glycans were determined by integration of all of the glycan peaks. Examples of such peaks are shown in FIG. 5.

N-glycosylation on Asn not residing within a consensus site motif (Asn-Xxx-Ser/Thr) is known to occur at low levels on human antibodies. This species is typically resolved as a post-heavy chain peak by rCE SDS. Determination of the relative percentage of this post-heavy chain peak area to the total heavy chain peak area yielded a level of non-consensus glycosylation in denosumab of approximately 1.5%.

Mass spectrometric based sequence studies were conducted to characterize the primary structure of denosumab. The results confirmed that there is no evidence of any O-linked glycosylation in denosumab.

7.2 Non-Enzymatic Glycation Characterization
7.2.1 Glycation Characterization Non-enzymatic glycation is a process by which a reducing sugar (glucose or galactose) reacts with a protein through the formation of a Schiff base between the aldehyde group of the sugar and the primary amines of a protein. In CP2-produced denosumab, nonenzymatic glycation, a species enriched in the CE-HPLC pre-peak, is located on one lysine residue (Lys-98) of denosumab.

Advancements in characterization techniques and high resolving mass spectrometry instruments enabled further characterization of the nonenzymatic glycation on denosumab. Denosumab were treated with sodium borohydride followed by reduction, alkylation and digestion with trypsin for peptide map analysis with mass spectrometry detection. Treatment with sodium borohydride, as described in Brady et al. (Anal. Chem., 2007, 79 (24), pp 9403-9413), stabilizes the bond between the sugar and protein, allowing for site identification by MS/MS. Using this technique, the identification of multiple glycation sites in CP4-produced denosumab were elucidated. The identified sites of nonenzymatic glycation for denosumab from the two processes are provided in Table 8, indicating the same sites of glycation are present. This anticipated result is due to the fact that glycation is not a random event but is highly dependent on solvent accessibility as well as a protein's localized chemical environment (Gadgil et al. J Pharm Sci. 2007 October; 96(10):2607-21.).

TABLE 12

Denosumab Sites of Glycation

| Glycation Location | Identified Tryptic Fragment | Glycation Sites |
| --- | --- | --- |
| Light Chain | TFGQGTkVEIK | K104 |
| | VEIkR | K108 |
| | VQWkVDNALQSGNSQESVTEQDSK | K150 |
| | DSTYSLSSTLTLSkADYEK | K184 |
| | HkVYACEVTHQGLSSPVTK | K191 |
| Heavy Chain | DNSkNTLYLQMNSLR | K76 |
| | AEDTAVYYCAk | K98 |
| | VDkTVER | K218 |
| | CCVECPPCPAPPVAGPSVFLFPPKPk | K249 |
| | VVSVLTVVHQDWLNGKEYk | K318 |
| | VSNkGLPAPIEK | K327 |
| | GLPAPIEkTISK | K335 |

The CP4 process utilizes both glucose and galactose during cell culture resulting in an antibody that is glycated with both glucose and galactose sugars. The glycation present on CP4 is about 24% with an estimated 12% due to galactose glycation.

Glucose is present at approximately 70-100 mg/dL (Pesce and Bodourian 1982) in human serum resulting in non-enzymatic glycation of circulating proteins. Galactose is naturally present in human serum at approximately 0.3 mg/dL. At these low serum galactose levels it is unlikely that healthy individuals would have circulating proteins with measurable levels of galactose glycation, the exception being patients with galactosaemia. The clinical safety of galactose glycation was unknown and therefore may be considered a new molecular species and could be a potential safety concern. To address this potential safety concern, a study was conducted to assess the glycation levels, clinical safety and efficacy impact of this post translational modification.

CP4-denosumab has about 24% glycation while CP2 has about 10% glycation. Twelve glycation sites were identified on CP2. The same twelve sites were detected on CP4 with no new glycation sites identified. CP4, CP2 and a CP4 samples enriched in glycation (70%) had equivalent potencies in the two functional bioassays demonstrating that glycation levels and galactose glycation did not impact product function. Additionally, tryptic peptide mapping experiments confirmed the drug substance sites of glycation are identical between the CP2 and CP4 processes with a total of 12 glycation sites identified, none of which are present in the CDR region of denosumab.

The CP4 process utilized glucose containing media for days 1-10 of cell culture followed by a low glucose and high galactose containing perfusion media on days 11-18. Monosaccharide analysis of the media determined the level of glucose on day 12 of cell culture was below the detectable levels. Therefore galactose was likely responsible for the majority of glycation after the media switch. Based on this data, a theoretical calculation was conducted to estimate that level of glucose versus galactose glycation present on CP4-denosumab. This calculation determined that approximately 50% of the CP4 glycation (24%) is due to galactose. This corresponds to 1 in 8 antibodies being glycated with galactose and 1 in 8 antibodies glycated with glucose.

7.2.2 Biological Characterization of Glycation

Modifications of therapeutic antibodies may result in a decrease in clinical efficacy or could impact patient safety. Therefore thorough characterization of CP4-denosumab with a specific emphasis on glycation was conducted. Potency analysis by the HTRF and the reporter gene binding assays were used to assess the biological function of CP4-denosumab compared to CP-denosumab.

During the development of the CP2-denosumab, forced glycation studies were conducted to assess glycation and impact to potency. Denosumab CP2 was forced glycated to levels ~68 times more than starting material. This sample retained all potency when analyzed by the HTRF and reporter gene assays.

In one assay, the purified CP4 CEX pre-peak species had approximately 70% glycation as compared to 24% in the main peak and basic fractions. All three purified fractions retained their potency by the HTRF and reporter gene assays, indicating that elevated levels of glycation did not impact product function. In addition, the relative potency of CP2 and CP4 were equivalent by the HTRF and reporter gene assays further demonstrating the glycation of CP4 did not impact product potency.

7.2.3 Glycation and Potential Impact to Fc Function

The clearance or serum half-life of IgG antibodies is regulated by the neonatal Fc receptor (FcRn). Previous forced glycation studies conducted on IgG1 and IgG2 antibodies (Goetze et al, 2012) had determined no impact to FcRn binding, suggesting a glycation modification has little impact on protein function. However, FcRn was conducted on CP2 and CP4 samples and these data demonstrate similar FcRn. Based on the forced glycation study results and given that the CP2 and CP4 had the same sites of glycation, the elevated levels of CP4 glycation did not impact FcRn binding.

7.2.4 Immunogenicity Assessment of Galactose Glycation

Denosumab with galactose glycation is a new species that has not been present in previous drug product presentations, therefore, an immunogenicity risk assessment was performed. A mature humoral immune response requires both a B-cell epitope and a T-cell epitope. The B-cell epitope is the antibody binding site and is usually dependent on protein conformation. A T-cell epitope is a linear amino acid sequence that binds to major histocompatability class II proteins on the surface of antigen presenting cells and elicits cytokine secretion from T cells that trigger antibody maturation. The following considerations were taken into account in the immunogenicity risk assessment:

B-cell epitope risk. CP4 contains new species glycated with galactose compared to CP2 which only had glucose glycation. No patients had been exposed to these new species and there was some uncertainty regarding the immune response. Glycation was distributed across up to 11 different lysines and approximately 12% of the denosumab molecules had 1 galactose. Therefore, the concentration of any one molecule with a specific amino acid modified with galactose was low.

Antibodies against fully human monoclonals usually bind to the CDR region due to non-tolerant sequences. The CDRs in denosumab contain 1 lysine and 6 in the adjacent framework which have the potential to be glycated with galactose. However, glycation in the CDRs had not been detected.

T-cell epitope risk. In silico analysis predicted only 1 minor T cell "agretope." Glycation does not cause sequence variants that would elicit T cell help. Galactose may enhance antigen processing, however, increased uptake by galactose enriched molecules may be due to higher order oligosaccharides.

Overall, the risk of glycation with galactose changing the immunogenicity of denosumab is minimal.

7.3 Non-Consensus N-Glycan (NCG)

Non-consensus N-glycans (NCG), as described in Valliere-Douglas et al (J Biol Chem. 2009 Nov. 20; 284(47): 32493-32506), represents the attachment of an oligosaccharide to an Asn residue that is not part of a consensus motif, typically in the antibody CH2 domain. This species is typically enriched in CE-HPLC pre-peaks and is resolved as a post-heavy chain peak by rCE-SDS.

Analysis of the CE-HPLC fractions by rCE-SDS indicated the CE-HPLC pre-peak was slightly enriched in the non-glycosyated heavy chain (NGHC) peak. Additionally, the rCE-SDS data indicated the CE-HPLC pre-peak fraction was slightly enriched in the post heavy chain peak (Table 9), a result consistent with the findings in Valliere-Douglas et al (2009).

TABLE 13

Peak Areas for rCE-SDS analysis of CE-HPLC Fractions

| Samples | % Heavy Chain | % Light Chain | % NGHC | % NCG |
|---|---|---|---|---|
| Denosumab Control | 65.7 | 31.5 | 0.8 | 1.5 |
| Pre-Peaks | 64.3 | 31.4 | 1.4 | 2.3 |
| Main | 65.9 | 31.7 | 0.8 | 1.2 |
| Post-main Peaks | 65.3 | 31.8 | 1.1 | 1.3 |

Example 8: Comparison of Glycan Profiles of Denosumab Produced by CP2 and CP4 Processes Oligosaccharide maps produced by High pH Anion Exchange Chromatography (HP-AEX) from CP2 and CP4 lots were compared. All the CP4 and CP2 lots met the comparability acceptance criteria of 4% to 11% Mannose-5 (Table 10). The CP4 drug substance lots had comparable levels of Mannose-5 to CP2 historical data and were within the historical minimum and maximum (5% to 9% Mannose-5). The glycan map (HP-AEX) overlays are shown in FIG. 5. The overlays show lower levels of A2F-G1 in the CP4 drug substance compared to the CP2 lots which was expected.

TABLE 14

Mannose-5 Glycan Map (HP-AEX) Lot Release Testing for Drug Substance

| Process | Lot | Mannose-5% | Comparability Acceptance Criteria [a] | Comparability Result |
|---|---|---|---|---|
| CP4 | 1 | 6% | 4% to 11% Mannose-5 | Meet |
|  | 2 | 7% |  |  |
|  | 3 | 6% |  |  |
| CP2 | 1 | 7% |  |  |
|  | 2 | 8% |  |  |
|  | 3 | 8% |  |  |

[a] Comparability acceptance criteria is based on internal historical data. These ranges should not be simply taken as determinative criteria for biosimilarity assessment. For purpose of biosimilarity, different or narrower ranges of Mannose-5 might be needed.

As a result of modifying the CP4 cell culture process to control for the Man-5 levels, it was anticipated that CP4-denosumab would have less % A2F-G1 and more % A2F-G0 oligosaccharide species than CP2-denosumab. These species are naturally occurring glycoforms in human serum, and as such are not considered a safety or efficacy concern.

To assess potential changes in the glycan profile, glycan map analysis was used to assess the N-linked glycans of denosumab. FIG. 5 demonstrates the consistent N-glycan profile between denosumab produced by the two processes. No new glycoforms were observed in the profile of CP4 lots. A summary of the % A2F-G0, % A2F-G1, and % Man 5 oligosaccharide species are shown in Table 10. The CP4 data were within the calculated tolerance interval (TI) ranges, with the % A2F-G1 results being on the low end of the calculated CP2 TI range. The slight shift in terminal galactosylation for CP2 lots versus CP4 lots is not expected to impact product safety or efficacy.

As these data show, there were no new carbohydrate species present in denosumab manufactured using the CP4 process as compared to that of CP2 process. The CP4 and CP2 lots meet the HP-AEX comparability criteria. A summary of all N-glycan species recorded during HP-AEX analysis is summarized in Tables 15.1 and 15.2. As shown in this summary table, the values obtained for the CP4 lots are similar to those from the CP2 process. The levels of sialylated species are similar between CP4 and CP2 lots. Minor differences in the % A1F-G0 levels are observed between CP4 and CP2 lots; however these differences are not anticipated to impact the efficacy of the product.

TABLE 15.1

Denosumab from CP4 and CP2, HP-AEX Comparability Summary Table

| N-Glycan Species | Comparability Acceptance Criteria [a] | CP4 Lot 1 | CP4 Lot 2 | CP4 Lot 3 | CP2 Lot 3 | CP2 Lot 2 | CP2 Lot 3 |
|---|---|---|---|---|---|---|---|
| A2F-G0 | 48% to 70% | 68 | 66 | 67 | 62 | 58 | 61 |
| A2F-G1 | 13% to 26% | 13 | 14 | 14 | 20 | 22 | 19 |
| Man 5 | 4% to 11% | 6 | 7 | 6 | 7 | 8 | 8 |

[a] Comparability acceptance criteria is based on internal historical data. These ranges should not be simply taken as determinative criteria for biosimilarity assessment. For purpose of biosimilarity, different or narrower ranges of glycan species might be needed.

TABLE 15.2

HP-AEX Denosumab CP4 and CP2 N-Glycan Species Summary Table

| N-Glycan Species | CP4 Lots | | | CP2 Lots | | |
|---|---|---|---|---|---|---|
|  | 1 | 2 | 3 | 1 | 2 | 3 |
| % A1-G0 | 1.2 | 1.2 | 1.1 | 1.2 | 1.3 | 1.2 |
| % A1F-G0 | 3.3 | 3.2 | 3.0 | 1.3 | 1.2 | 1.5 |
| % A2-G0 | 5.3 | 6.1 | 5.6 | 4.7 | 4.4 | 4.9 |
| % A2-G1 | 0.9 | 1.1 | 1.0 | 1.1 | 1.2 | 1.1 |
| % A2F-G0 | 67.9 | 65.9 | 66.7 | 61.5 | 57.6 | 60.5 |
| % A2F-G1 | 13.2 | 13.5 | 14.4 | 19.6 | 22.4 | 19.0 |
| % A2F-G2 | 1.1 | 1.1 | 1.3 | 2.1 | 2.7 | 2.1 |
| % Mannose-5 | 6.0 | 6.7 | 5.8 | 7.1 | 7.6 | 7.6 |
| % Minor Peaks | 0.5 | 0.6 | 0.5 | 0.9 | 1.1 | 1.3 |
| % Sialylated Peaks | 0.5 | 0.6 | 0.6 | 0.6 | 0.6 | 0.7 |

The increased levels of glycation observed in denosumab CP4 drug substance compared with CP2 drug substance were consistent with changes made for the CP4 process, namely, a combination of increased cell culture process duration and the use of both glucose and galactose in the cell culture media. Galactose was not used in the CP2 production feed, and galactose in the culture medium has been shown to lead to higher levels of nonenzymatic glycation than glucose (Quan et al., Anal Biochem 2008; 373(2):179-91). CP4 drug substance has approximately 24% total glycation compared with approximately 10% for CP2 drug substance. The elevated level of glycation present on CP4 drug substance is expected to be a combination of both glucose and galactose.

In a previous study, CP2 drug substance retained full potency by the HTRF and reporter gene assays even when glycation was increased~68-fold (by forced glycation). The potencies of CP4 drug substance and CP2 drug substance were equivalent by the HTRF, and reporter gene assays, further demonstrating that the roughly 2-fold higher level of glycation of denosumab CP4 drug substance did not impact potency (Tables 12.1 and 12.2). Additionally, forced glycation of IgG1 and IgG2 antibodies caused no measurable impact on FcRn binding, further suggesting that glycation had little impact on denosumab's biological functions. Together, these data suggest that the increased glycation observed for CP4 is not expected to impact product safety or efficacy.

TABLE 16.1

HTRF Potency Results

| Process | Lot No. | % Relative Potency | Comparability Acceptance Criteria | Comparability Result |
|---|---|---|---|---|
| CP4 | 1 | 97% | 82% to 128% [a] Relative Potency | Meet |
|  | 2 | 96% |  |  |
|  | 3 | 101% |  |  |
| CP2 | 1 | 104% |  |  |
|  | 2 | 97% |  |  |
|  | 2 | 99% |  |  |

[a] Comparability acceptance criteria is based on internal historical data. These ranges should not be simply taken as determinative criteria for biosimilarity assessment. For purpose of biosimilarity, different or narrower ranges of relative potency might be needed.

TABLE 16.2

Comparability Reporter Gene Assay Summary Table

| Process | Lot Number | Potency | % CV |
|---|---|---|---|
| CP4 | 1 | 99 | 1 |
|  | 2 | 101 | 0 |
|  | 3 | 100 | 2 |
| CP2 | 1 | 98 | 2 |
|  | 2 | 97 | 1 |
|  | 3 | 97 | 0 |

Example 9: Effect of Glucose, Sucrose, and Galactose Concentration on High-Mannose Content In this example, different concentrations of glucose, sucrose, and galactose were used to assess their effects on the high-mannose content of denosumab.

Two carbon source alternatives for glucose, the disaccharide sucrose and the monosaccharide galactose were chosen to assess their effects on percentage of denosumab molecules comprising high-mannose. Culture medium change occurred at day 11 to 17 by perfusion, as described in detail above.

In one study, the effect of glucose and galactose concentration on Man-5 content was assessed. The Experimental design is shown in Table 13.

TABLE 17

Experimental Design: Glucose and Galactose

| Pattern | Run ID/CCD Number | Glucose | Galactose |
|---|---|---|---|
| Control | 102/1122 | 2 | 11.5 |
| ++ | 103/1123 | 3 | 13 |
| -- | 104/1124 | 0 | 10 |
| -+ | 105/1125 | 0 | 13 |
| -- | 106/1126 | 0 | 10 |
| 0 | 107/1127 | 1.5 | 11.5 |
| -+ | 108/1128 | 0 | 13 |
| +- | 109/1129 | 3 | 10 |
| Control | 110/1130 | 2 | 11.5 |
| ++ | 111/1131 | 3 | 13 |
| +- | 112/1132 | 3 | 10 |
| 0 | 113/1133 | 1.5 | 11.5 |

Figure 7A:
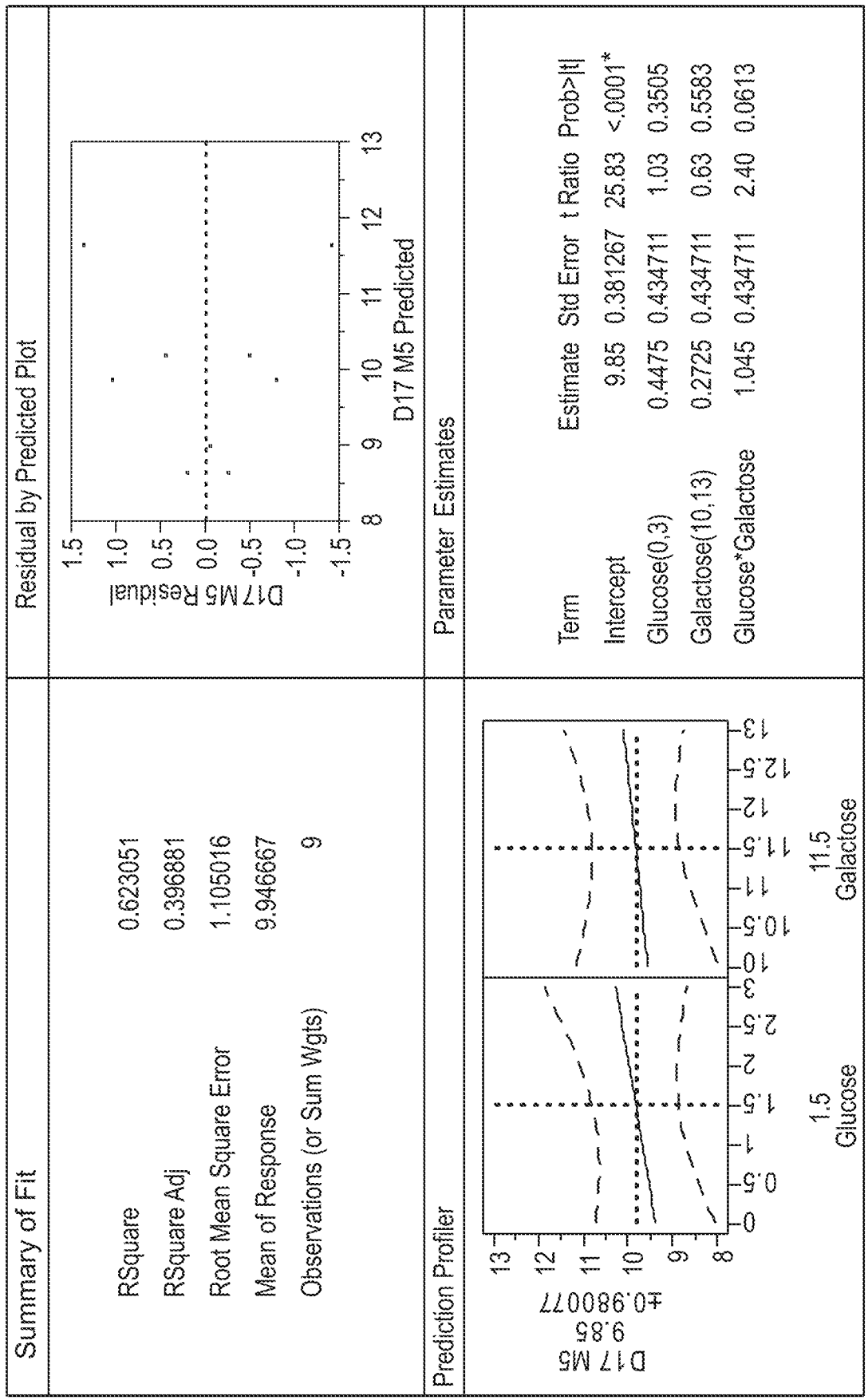
FIGS. 7A-7C show the effect of glucose and galactose concentration on denosumab high-mannose content.
Figure 7B:
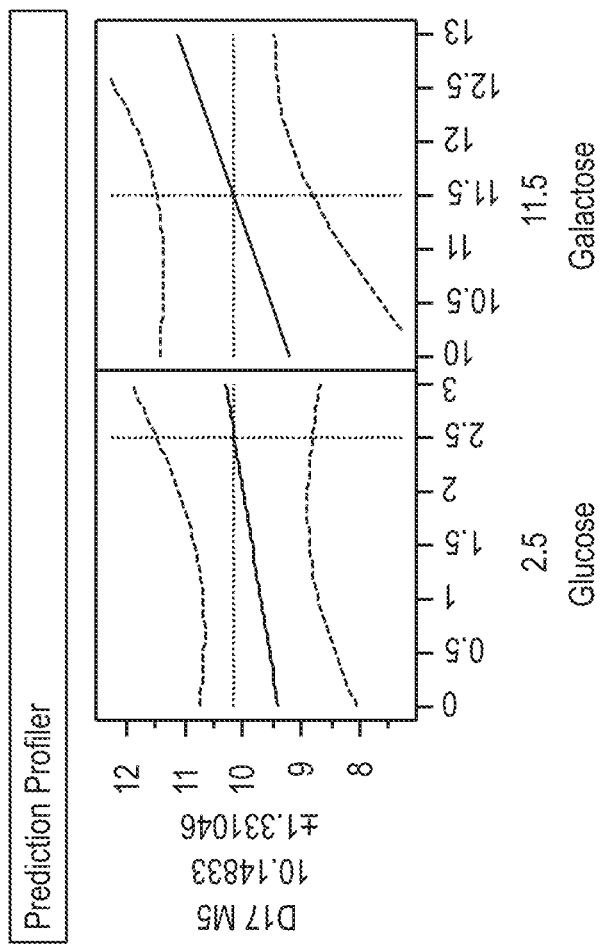
Figure 7C:
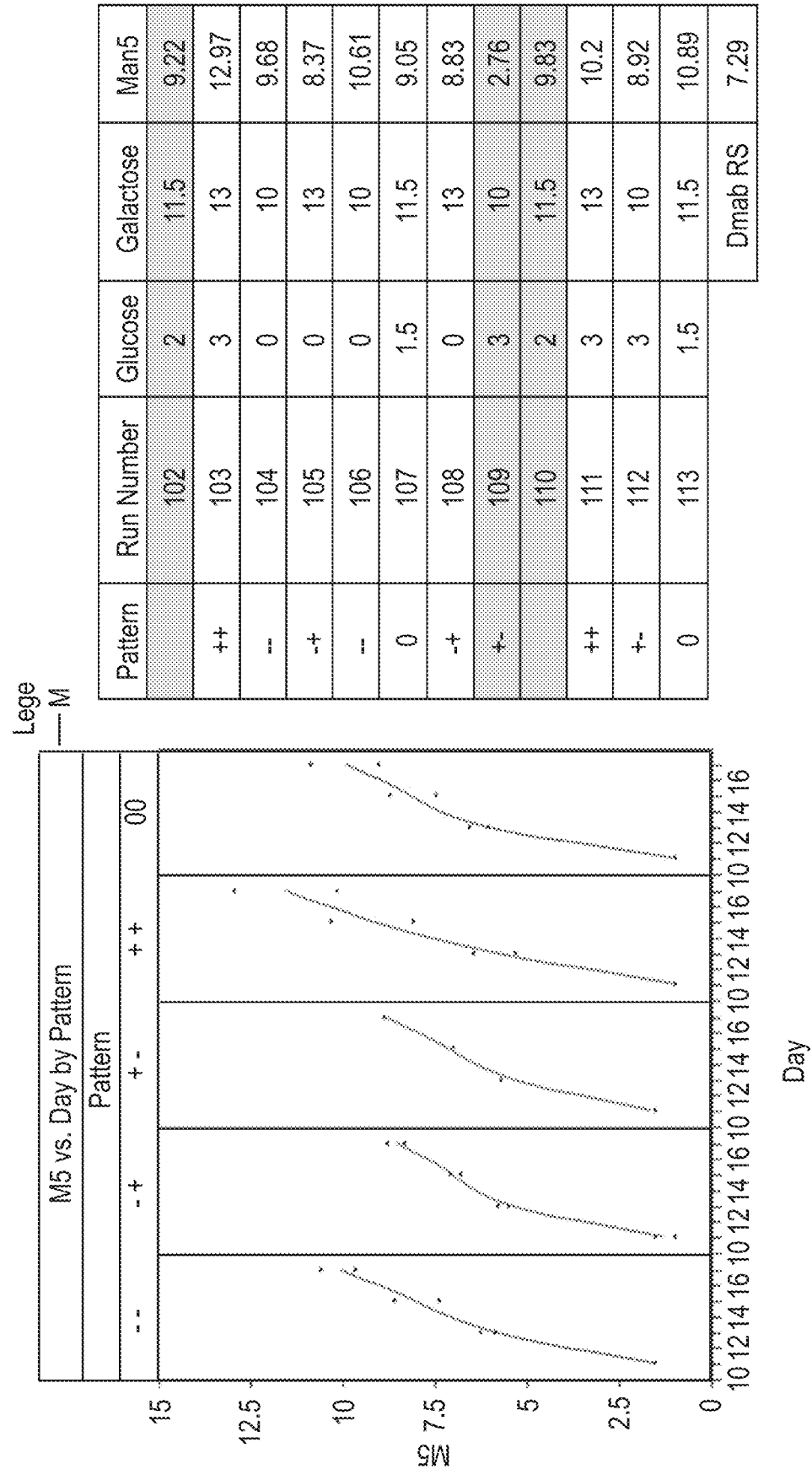

FIG. 7A show the full model analysis of day 17 Man-5, with the prediction profile at the experiment center points. The data suggest that the interaction between glucose and galactose is likely important to Man-5 levels. FIG. 7B shows Day 17 prediction of Man-5 with the glucose level set at 2.5 g/L. Man-5 results were obtained by HELIC analytical method. FIG. 7C shows the time course change in Man-5 from days 11 to 17. The graph shows the increase of Man-5 overtime.

Table 14 shows the glycan profile of this study. None of the variations of these glycan species were statistically significant.

TABLE 18

Day 17 Glycan Profile

| Run/CCD Number | Glucose | Galactose | % Man 5 | % A2G0F | % A2G1F | % A2G2F | % Peak B, RP-HPLC |
|---|---|---|---|---|---|---|---|
| 103/1123 | 3 | 13 | 12.97 | 36.66 | 30.55 | 6.24 | 16.91 |
| 104/1124 | 0 | 10 | 9.68 | 33.96 | 33.78 | 8.16 | 14.92 |
| 105/1125 | 0 | 13 | 8.37 | 40.04 | 31.69 | 6.18 | 13.69 |
| 106/1126 | 0 | 10 | 10.61 | 37.88 | 30.79 | 6.15 | 16.3 |
| 107/1127 | 1.5 | 11.5 | 9.05 | 39.88 | 31.14 | 6.13 | 18.09 |
| 108/1128 | 0 | 13 | 8.83 | 38.64 | 32.31 | 6.53 | 15.57 |
| 111/1131 | 3 | 13 | 10.2 | 41.04 | 29.74 | 5.92 | 17.5 |
| 112/1132 | 3 | 10 | 8.92 | 39.31 | 31.47 | 6.56 | 16.02 |
| 113/1133 | 1.5 | 11.5 | 10.89 | 36.34 | 31.72 | 7.1 | 15.58 |

Based on this study, it was determined that for about 10% Man-5, the culture medium should comprise about 2.5 g/L glucose and about 11.5 g/L galactose. These concentrations resulted in a balance between growth, viability and titer, while achieving the primary goal of attaining the Man-5 target. Analysis also shows a correlation between glucose concentration with growth and titer, higher glucose yields higher growth and titer. A concentration of 2.5 g/L galactose was chosen even though higher galactose may yield in higher Man-5 levels, but higher galactose could have a potential negative effect on culture viability.

In a second study, the effect of glucose and sucrose concentration on Man-5 content was assessed. The Experimental design is shown in Table 15. The targeted Man-5 is at least 7%-9%.

TABLE 19

Experimental Design: Glucose and Sucrose

| Pattern | Glucose | Sucrose | Galactose | comments | Reactor Number |
|---|---|---|---|---|---|
| 1 ++ | 6 | 24 | • |  | 1 |
| 2 | 2 | 16 | 11.5 | if Gal < 2, feed Gal | 2 |
| 3 -- | 2 | 16 | • |  | 3 |
| 4 -+ | 2 | 24 | • |  | 4 |
| 5 -+ | 2 | 24 | • |  | 5 |
| 6 00 | 4 | 20 | • |  | 6 |
| 7 +- | 6 | 16 | • |  | 7 |
| 8 -- | 2 | 16 | • |  | 8 |
| 9 ++ | 6 | 24 | • |  | 9 |
| 10 | 2 | 16 | 11.5 | if Gal < 2, feed Gal | 10 |
| 11 +- | 6 | 16 | • |  | 11 |
| 12 00 | 4 | 20 | • |  | 12 |

Figure 8A:
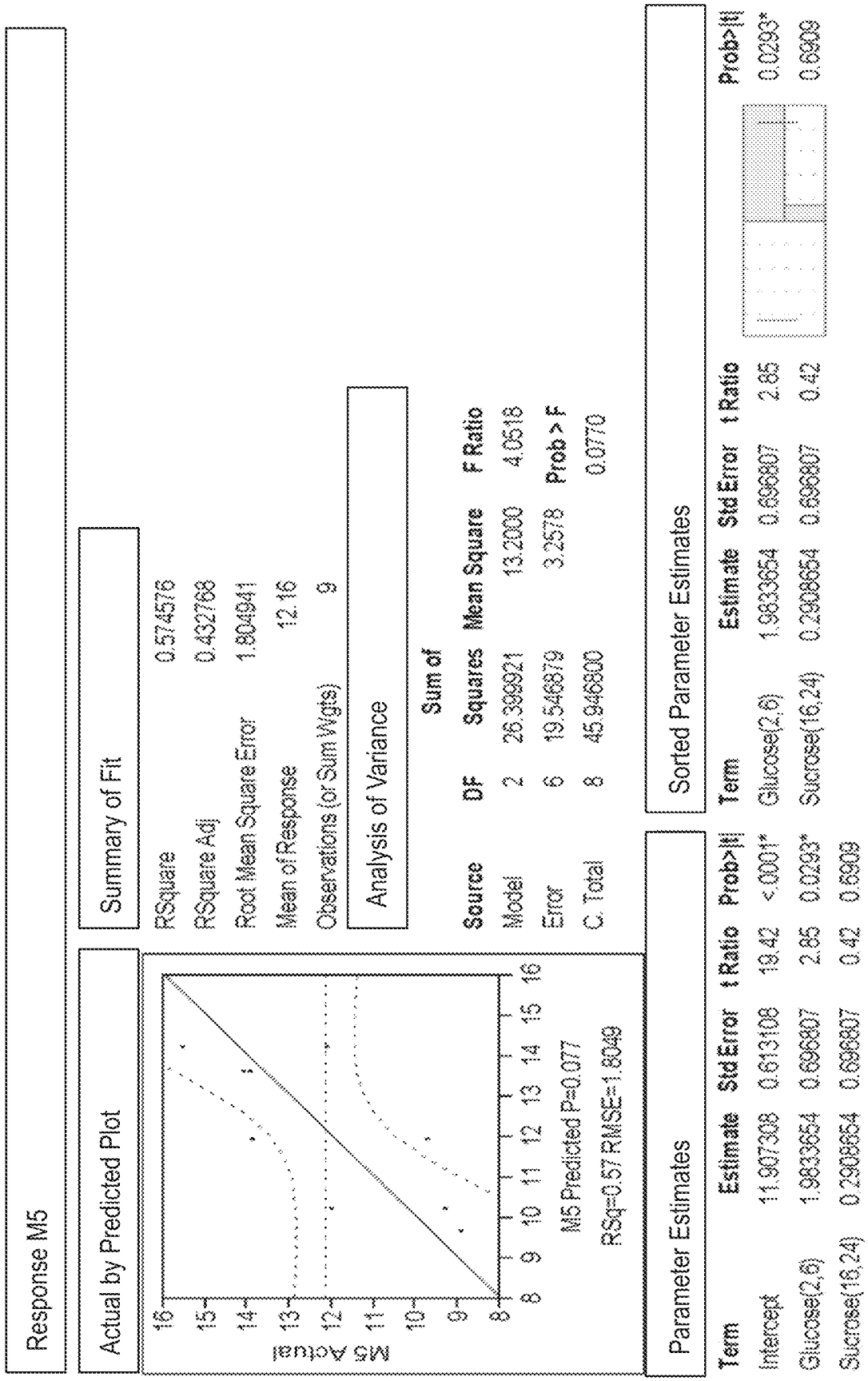
FIG. 8A shows the full model analysis of day 17 Man-5.
Figure 8B:
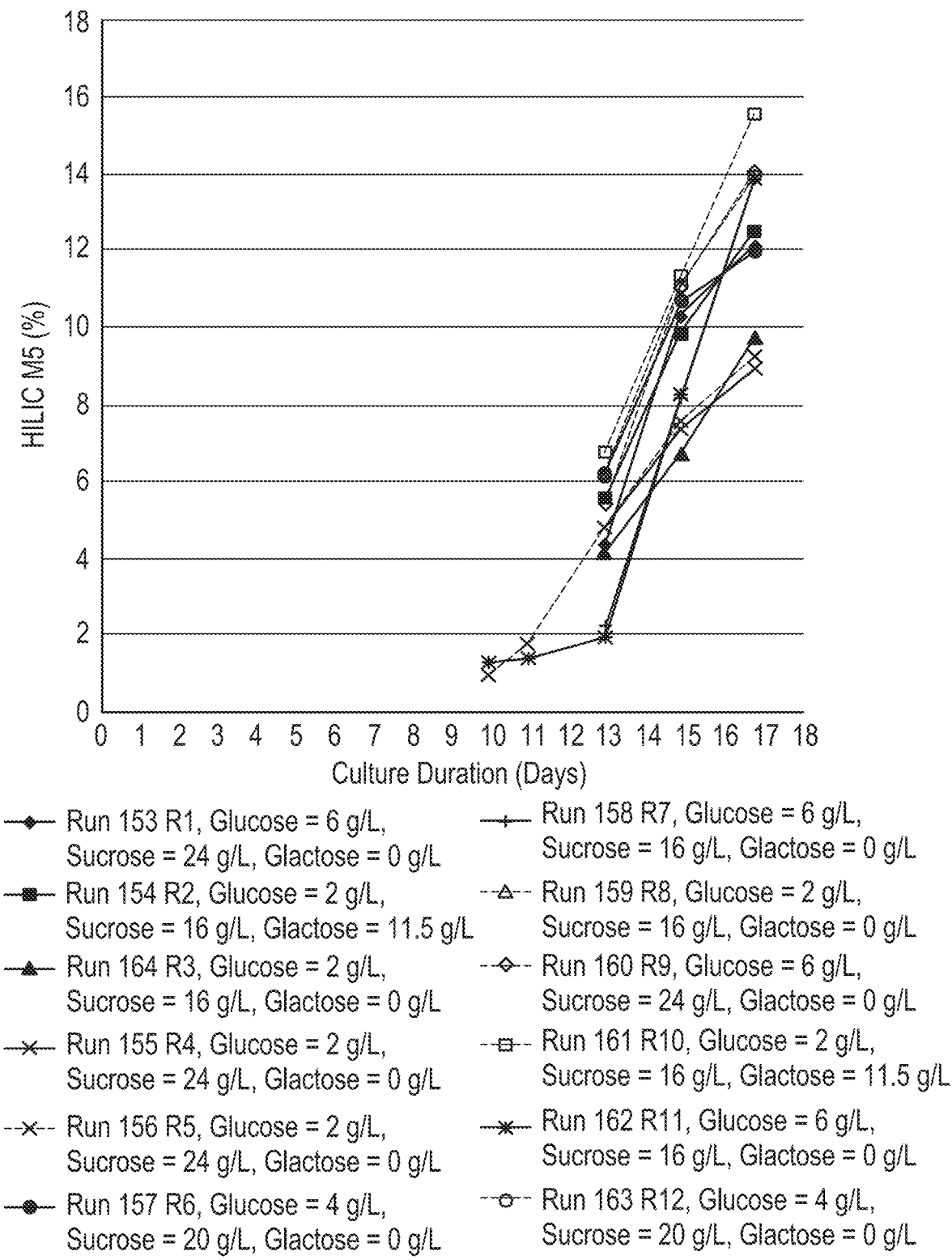
FIG. 8B shows the Man-5 levels as assessed by the HILIC.
Figure 8C:
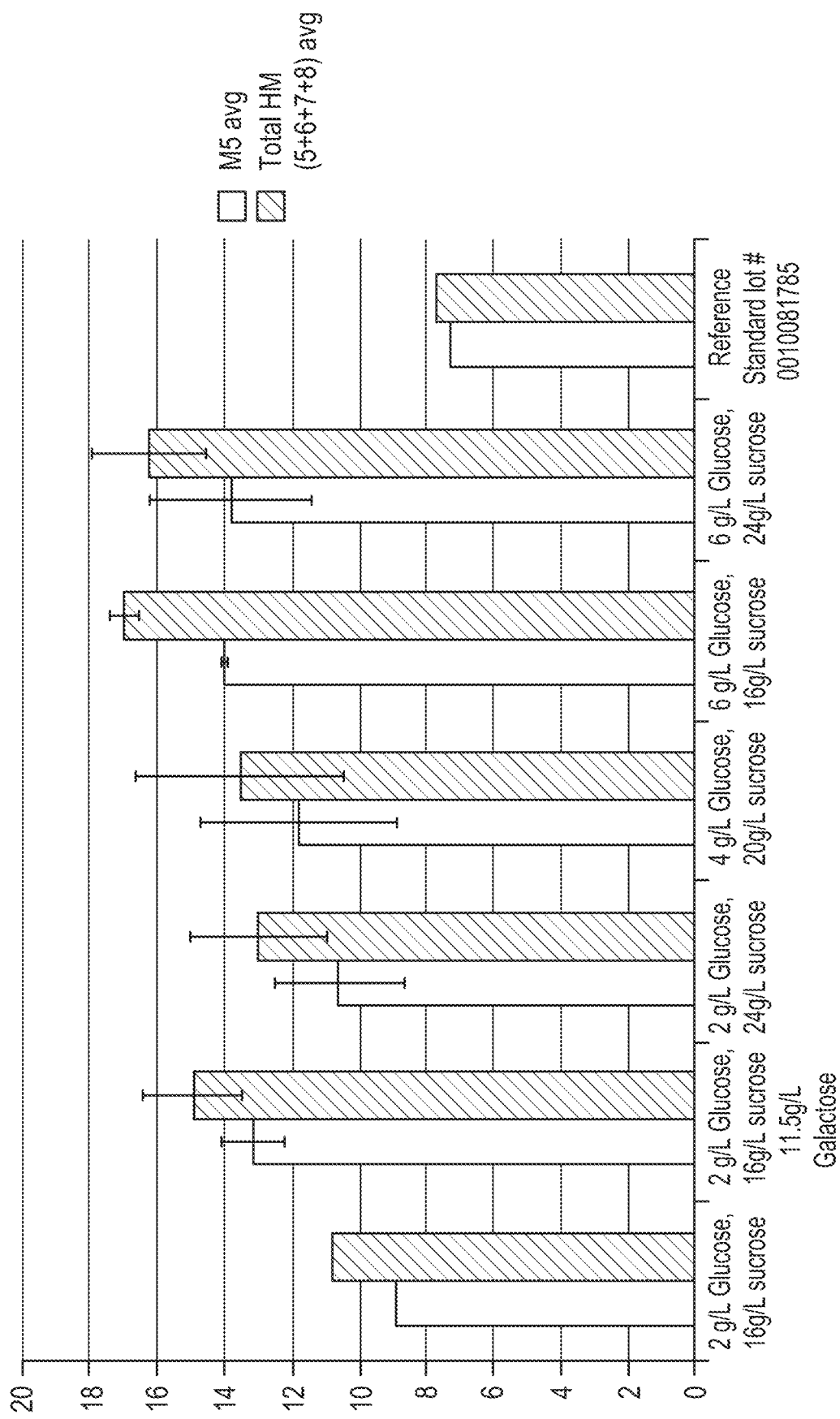
FIG. 8C shows Man-5 and total High Mannose species, as compared to CP2 reference.

Of the factors tested, all achieved Man-5 levels above 8% on day 17 and many had achieved above 10% by day 15. The Day 17 values for Man-5 ranged from 9% up to just below 16%. The two conditions that came closest to the CP2 levels were the conditions with 2 g/L of glucose with either 16 or 24 g/L of Sucrose. The graphs for Man-5 by the HILIC assay is shown in FIG. 8B. FIG. 8C shows Man-5 and total High Mannose species, as compared to CP2 reference.

Example 10: Effect of Low Glucose and Galactose Supplement on SR3 GS-KO Host Cells In this example, another CHO host cell line was used to assess the effect of low-glucose culture medium that was supplemented with an alternative carbon source (galactose). Cell line SR3 GS-KO is derived from CHO-K1 cell line, with GS knockout.

Figure 9A:
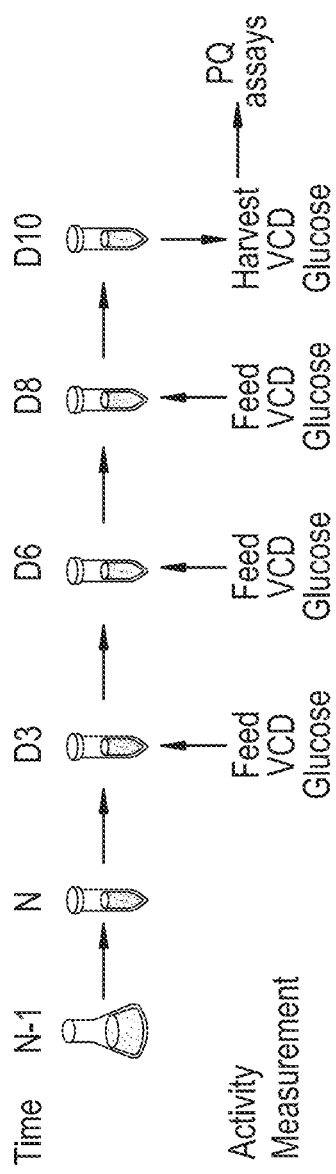
FIG. 9A is a diagram showing a 10-day fed batch scheme.

A 10-day Fed-Batch (FB) platform was used to evaluate the growth, expression and product quality (PQ) profile of denosumab molecules under production condition with the following steps (FIG. 9A):
1. N−1 inoculation. Pools were recovered to >85% viability prior to 10-day FB. A 4-day seed-train culture of denosumab-transfected SR3-E1 GS-KO cells were seeded at $5 \times 10^5$ cells/ml in culture media.
2. N inoculation. Production cultures were set up from the N−1 seed train wherein cells were seeded in 50-mL spin tubes. Fed-batch culture was seeded at $1 \times 10^6$ cells/ml on day 0 with high viability cells (>98%). Culture vessels were maintained at 36° C. +5% $CO_2$, while shaking at 225 rpm during production phase.
3. In-process monitoring. Viable cell density and percent viability were measured on day 3, 6, 8 and 10 using Vicell. Glucose consumption level was measured on the same day using Novaflex.
4. Feed and supplement. Production cultures were fed on day 3, 6, and 8 with feed medium at 5% of the initial culture starting volume, and 1× tyrosine-cysteine supplement, fed at 0.4% of the feed volume. A supplement of 10 g/L galactose was added as bolus on feed days while glucose level was allowed to drop by consumption and was fed only to maintain 1-5 g/L level during production.
5. Titer and Product Quality Assessment. Prior to harvest on day 10, viable cell density, percent viability and glucose level were measured. To harvest conditioned media (CM), cultures were centrifuged at 200 g for 15 minutes. CM was collected for titer measurement and ATOLL centricolumn purification. Purified material was used for product quality assessment which include HILIC, CEX-HPLC, SE-HPLC, nrCE-SDS and rCE-SDS assays.

10.1 D-Galactose Addition During 10-Day Fed Batch Did not Affect Culture Viability.

Figure 9B:
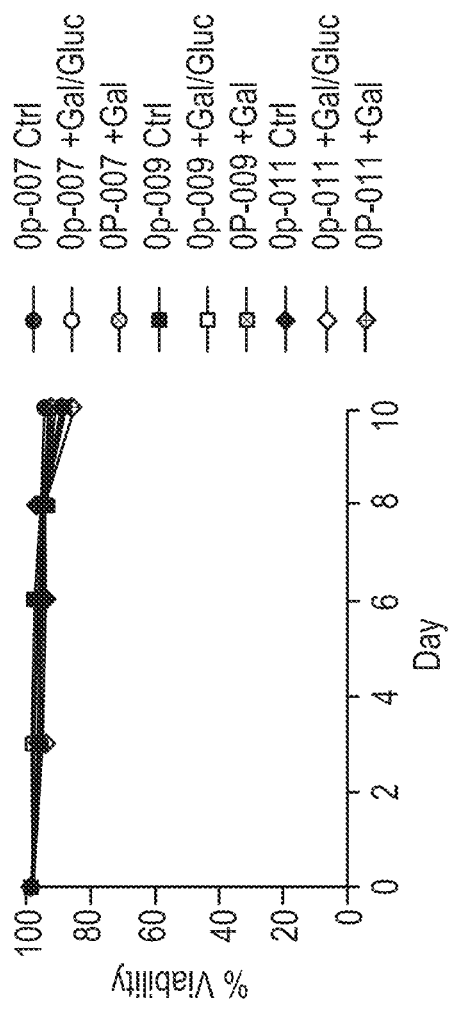
FIG. 9B shows the cell cultures maintained high viability during the 10-day fed-batch. All samples showed >80% viability for all tested conditions. Closed circle, rectangle and diamond represent control condition where glucose was supplemented to maintain 10-12 g/L level in the bioreactor during feed days without the addition of galactose. Open circle, rectangle and diamond represent the condition in which 10 g/L galactose was supplemented along with glucose to maintain 10-12 g/L level in the bioreactor during feed days. Hatched bars represent the condition in which 10 g/L galactose was supplemented during feed days while glucose level is allowed to drop by consumption to 1-5 g/L level in the bioreactor.

Three pools of denosumab-transfected SR3-E1 GSKO cells were tested in replicates in three culture conditions: 1) Ctrl or control, glucose supplement on feed days to maintain 10-12 g/L level during culture; 2) Gal/Gluc, 10 g/L galactose supplemented as bolus along with glucose to maintain 10-12 g/L level; and 3) Gal only, 10 g/L galactose supplemented as bolus without glucose feed to maintain 1-5 g/L glucose level during culture. Viability of cells during 10-day fed batch was measured using Vicell on day 3, 6, 8, and 10 prior to feeding and harvest. All cultures across pools and conditions showed high viability (>80%) throughout the 10-day fed-batch (FIG. 9B), suggesting that modifying sugar level and source in production culture had minimal impact on viability.

10.2 Effect of Low Glucose Level on Cell Growth and Specific Productivity.

Figure 9C:
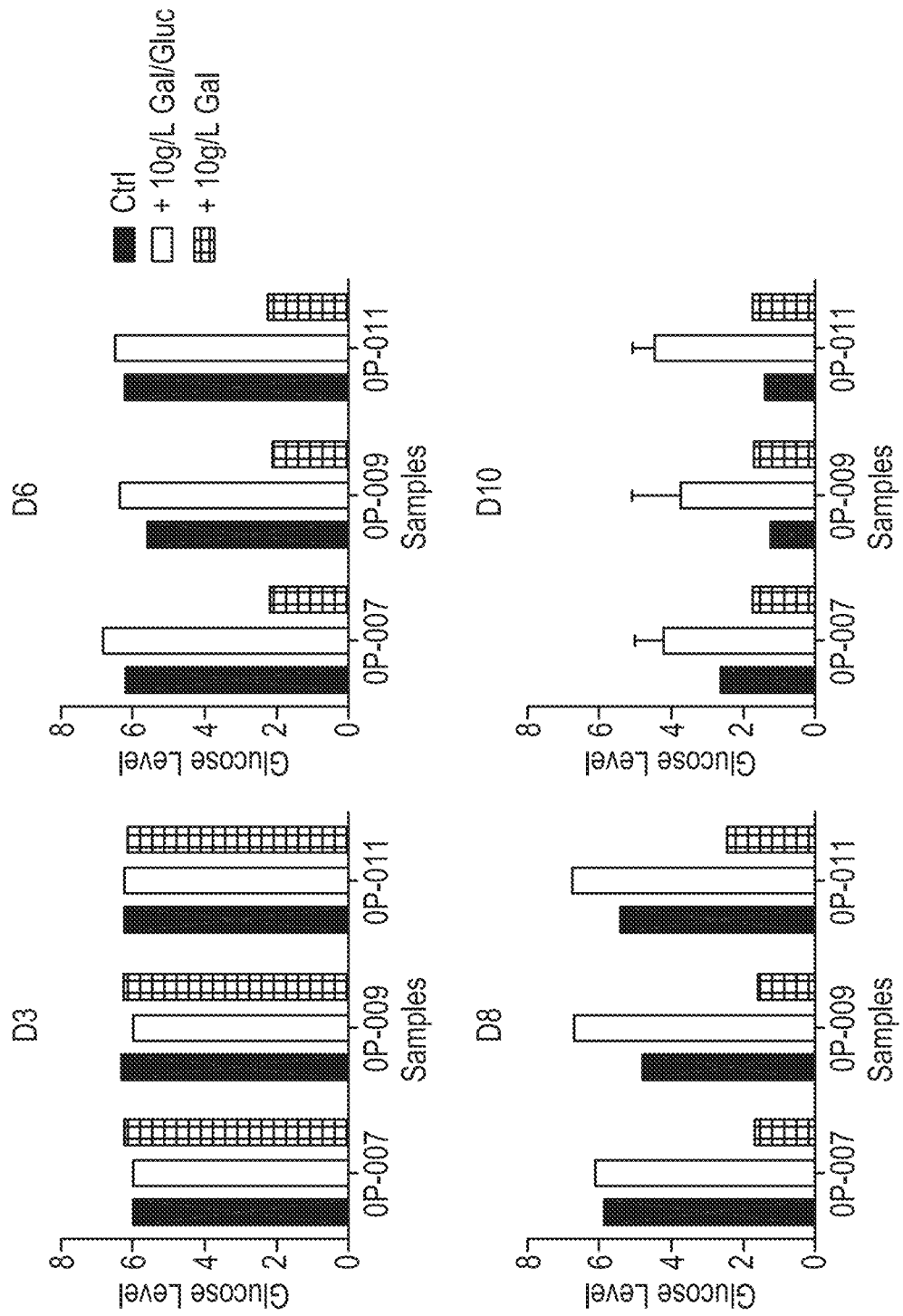
FIG. 9C shows the glucose level in bioreactor on feed and harvest days. Measurement of glucose was performed to guide the amount of glucose feeding required for two of the culture conditions. On each of day 3, 6, and 8, ~5-6 g/L of glucose was supplemented to control and gal/gluc cultures (black and white bars respectively), while no glucose was added to gal only culture (hatched bars).

Measurement of glucose levels in bioreactor was conducted using Novaflex on day 3, 6, 8, and 10 prior to feeding to ensure that glucose was maintained at appropriate level for each condition. For gal only culture condition, glucose level was allowed to drop by consumption to ~2 g/L by day 6. In this condition, glucose remained at that level throughout the rest of the 10-day fed batch (FIG. 9C). This observation suggests that in the absence of glucose as sugar source, the denosumab-expressing SR3-E1 GSKO cells may switch to using galactose to sustain their growth and other cellular activity.

Figure 10A:
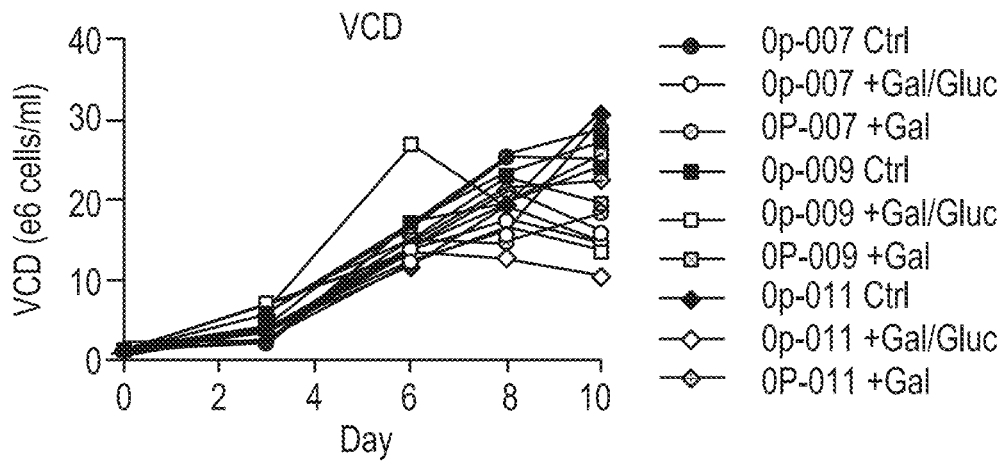
FIGS. 10A-10C show the effect of modifying sugar source on cell growth, titer and specific productivity.
Figure 10B:
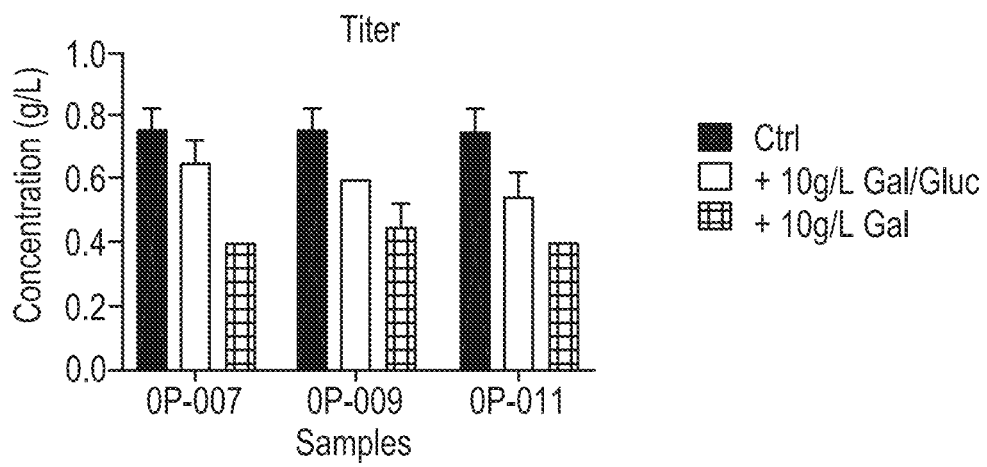
Figure 10C:
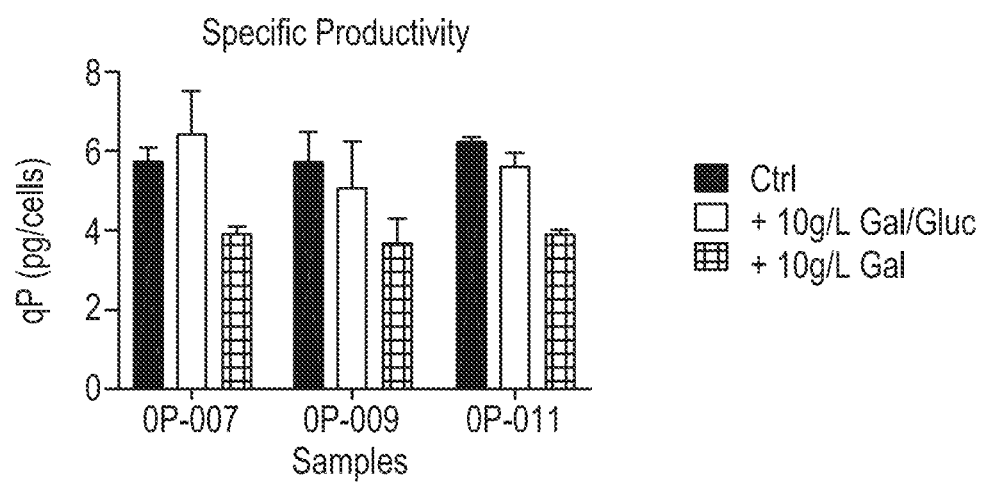

The low level of glucose did not affect viability, but cell growth was slightly slower in the cultures where galactose was added. The slowest growth was observed in the cultures where both galactose and glucose were supplemented (FIG. 10A). While titer appeared lower in this culture condition, the specific productivity did not show significant difference compared to control cultures (FIGS. 10B-10C). The addition of galactose at low glucose condition correlated with a small titer drop and decrease in specific productivity.

10.3 Addition of D-Galactose in Combination with Low-Glucose Increased High-Mannose Level of Denosumab.

Conditioned media from 10-day fed batch was subjected to ATOLL purification and product quality attribute assays. Purified product was analyzed using size exclusion chromatography (SE-HPLC) and was found to have ~99% purity and <1% high molecular weight and low molecular weight impurities (data not shown).

Figure 11:
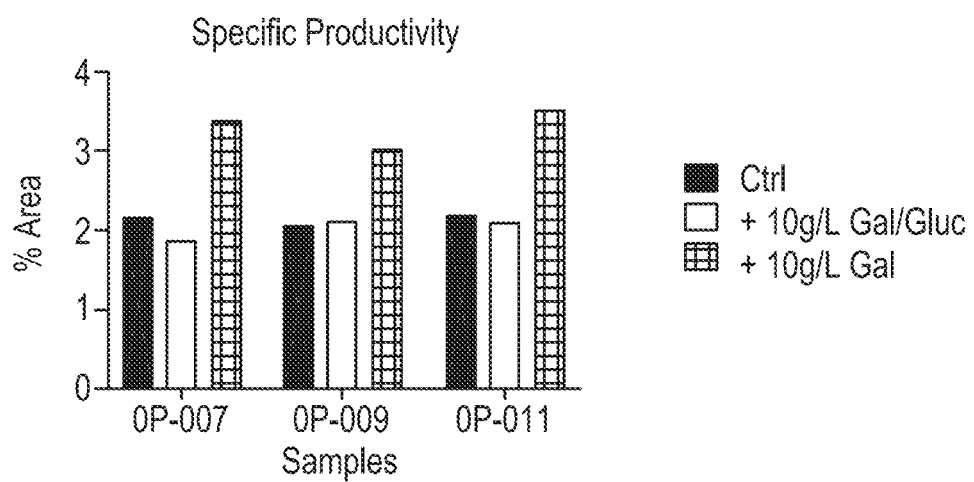
FIG. 11 shows that high-mannose level increased when galactose was added and glucose level was low. Bar-chart showing the reported % area of Man-5 in each pool at the end of 10-day fed batch. Black bars represent the control condition where glucose was supplemented to maintain 10-12 g/L level in the bioreactor during feed days. White bars represent the condition in which 10 g/L galactose was supplemented along with glucose to maintain 10-12 g/L level in the bioreactor during feed days. Hatched bars represent the condition in which 10 g/L galactose was supplemented during feed days while glucose level was allowed to drop by consumption to 1-5 g/L level in the bioreactor.

Hydrophilic interaction chromatography (HILIC) was subsequently performed to measure the product's glycan level. The results show that the addition of galactose in the presence of high glucose level does not affect the high-mannose (M5) level of denosumab. On the other hand, 10 g/L galactose supplementation at low glucose level increased high mannose level by about 1.5 fold or more (FIG. 11). This data suggests that altering sugar source from glucose to galactose during small-scale production had a direct impact on the high-mannose level of the product.

10.4 Addition of Galactose Increased Mono- and Bi-Galactosylated Glycan Residues.

Figure 12:
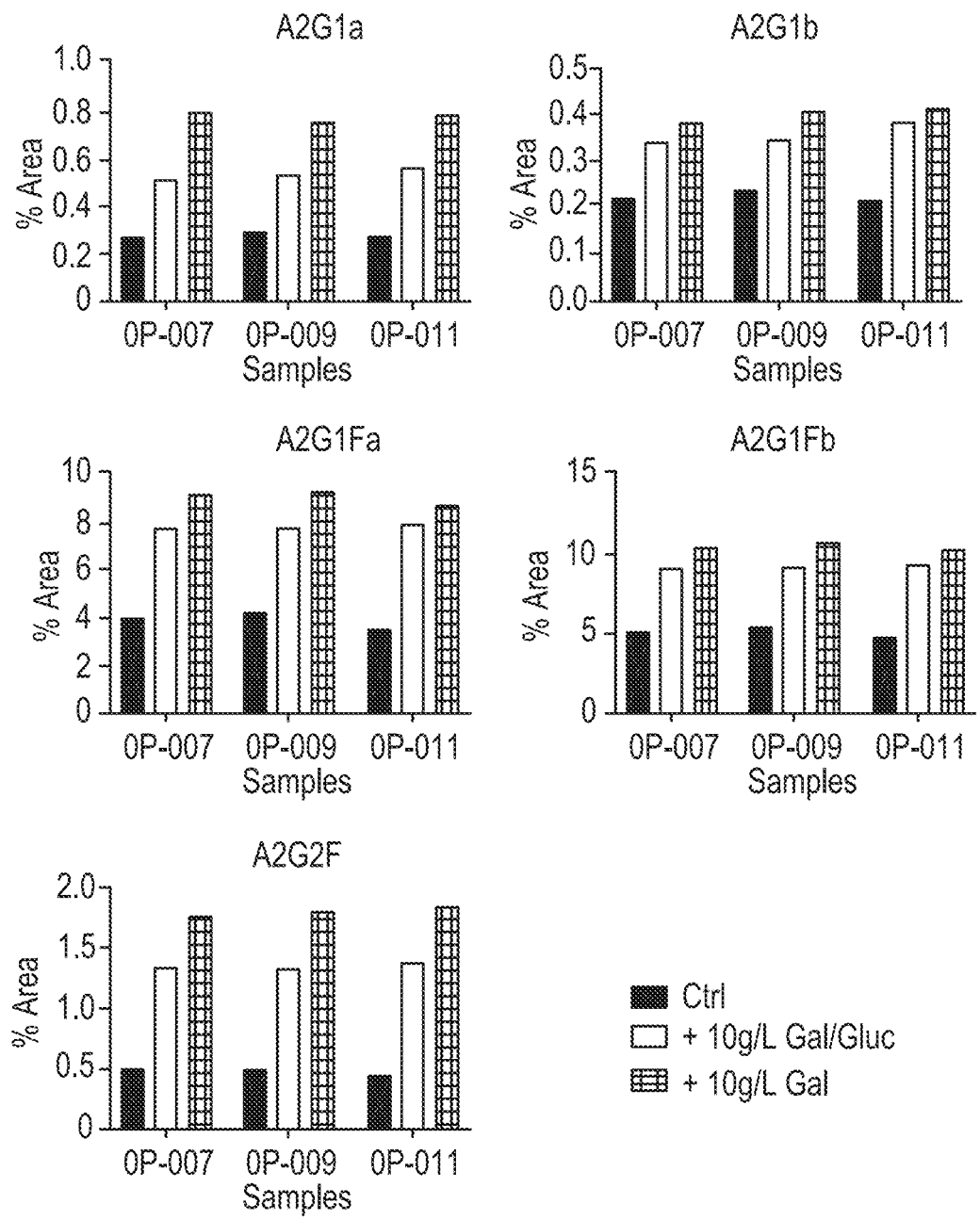
FIG. 12 shows that D-galactose addition increased mono- and bi-galacto glycan residues, but not agalacto residues. Bar-chart showing the reported % area of glycan residue in each pool at the end of 10-day fed batch. Black bars represent the control condition where glucose was supplemented to maintain 10-12 g/L level in the bioreactor during feed days. White bars represent the condition in which 10 g/L galactose was supplemented along with glucose to maintain 10-12 g/L level in the bioreactor during feed days. Hatched bars represent the condition in which 10 g/L galactose was supplemented during feed days while glucose level was allowed to drop by consumption to 1-5 g/L level in the bioreactor.

Analysis of glycan profile further showed that adding galactose supplement during 10-day fed-batch resulted in minimal decrease in agalacto residues, but increased the asialo monogalacto and bigalacto residues. The increase in these residues was inversely proportional to the level of glucose present in the cultures with low glucose condition showing ~2-4 fold increase (FIG. 12).

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following embodiments.

Carbohydrate moieties are described herein with reference to commonly used nomenclature for oligosaccharides. A review of carbohydrate chemistry which uses this nomenclature can be found, for example, in Hubbard and Ivatt, Ann. Rev. Biochem. 50:555-583 (1981). This nomenclature includes, for instance, Man, which represents mannose; Gal which represents galactose; and Glc, which represents glucose. Commonly known glycans are shown in Table 2.

"High-mannose" glycan is a glycan moiety comprising 5-9 mannose units, such as high-mannose 5 (Man-5) glycan, high-mannose 6 (Man-6) glycan, high-mannose 7 (Man-7) glycan, high-mannose 8 (Man-8) glycan, and high-mannose 9 (Man-9) glycan.

The invention claimed is:

1. A method of increasing the level of high-mannose present on denosumab molecules, wherein said denosumab molecules are recombinantly-expressed by a mammalian host cell, comprising:
   (a) incubating said mammalian host cell in a first culture medium during growth phase until the cell density is at least $1\times10^6$ viable cells/mL, wherein said first culture medium comprises from 1 g/L to 20 g/L glucose; and subsequently
   (b) incubating host cells from step (a) in a second culture medium during production phase to express said denosumab molecules, wherein said second culture medium comprises from 0 g/L to 10 g/L glucose and from 5 g/L to 20 g/L galactose;
wherein from 2% to 14% of the denosumab molecules comprise high-mannose glycan at N-298 site.

2. The method of claim 1, wherein during the growth phase, the glucose concentration is maintained at from 4 g/L to 20 g/L by bolus feed or perfusion.

3. The method of claim 2, wherein when the host cells are incubated in the second culture medium during the production phase, the glucose concentration is maintained at from 0 g/L to 8 g/L, and the galactose concentration is maintained at from 7 g/L to 15 g/L, by bolus feed or perfusion.

4. The method of claim 1, wherein during the production phase, the host cells are initially maintained in the first culture medium for about 3 to about 15 days, and subsequently transitioned into the second culture medium by perfusion or bolus feed.

5. The method of claim 1, wherein in step (a), said cell density is from $5\times10^6$ viable cells/mL to $12\times10^6$ viable cells/mL.

6. The method of claim 1, wherein from about 4% to about 11% of the denosumab molecules comprise high-mannose at the N-298 site.

7. The method of claim 1, wherein said mammalian host cell is a CHO cell.

8. The method of claim 1, wherein said mammalian host cell is a CS-9 cell.

9. The method of claim 1, wherein said first culture medium comprises methotrexate (MTX).

10. The method of claim 1, comprising:
   (a) incubating said mammalian host cell in a first culture medium during growth phase, and supplementing the culture with one or more bolus feeds, wherein the glucose concentration is maintained at from about 4 g/L to about 18 g/L during the growth phase;
   (b) transitioning host cells from step (a) from growth phase to production phase, and maintaining the glucose concentration at from about 4 g/L to about 18 g/L for about 3 days to about 15 days; and subsequently
   (c) transitioning the host cells of (b) into a second culture medium, wherein said second culture medium comprises from about 1 g/L to about 5 g/L glucose and from about 10 g/L to about 12 g/L galactose.

* * * * *

SEQUENCE LISTING

```
<160> NUMBER OF SEQ ID NOS: 6

<210> SEQ ID NO 1
<211> LENGTH: 448
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300
```

```
Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 215
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 3
<211> LENGTH: 1401
<212> TYPE: DNA
<213> ORGANISM: Homo sapiens

<400> SEQUENCE: 3
atggagtttg ggctgagctg gcttttctt gtggctattt taaaaggtgt ccagtgtgag      60
gtgcagctgt tggagtctgg gggaggcttg gtacagcctg gggggtccct gagactctcc     120
tgtgcagcct ctggattcac ctttagcagc tatgccatga gctgggtccg ccaggctcca     180
gggaaggggc tggagtgggt ctcaggtatt actgggagtg gtggtagtac atactacgca     240
gactccgtga agggccggtt caccatctcc agagacaatt ccaagaacac gctgtatctg     300
caaatgaaca gcctgagagc cgaggacacg gccgtatatt actgtgcgaa agatccaggg     360
actacggtga ttatgagttg gttcgacccc tggggccagg gaaccctggt caccgtctcc     420
tcagcctcca ccaagggccc atcggtcttc cccctggcgc cctgctccag gagcacctcc     480
gagagcacag cggccctggg ctgcctggtc aaggactact cccccgaacc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc ccccaaaacc caaggacacc ctcatgatct cccggacccc tgaggtcacg     840
tgcgtggtgg tggacgtgag ccacgaagac cccgaggtcc agttcaactg gtacgtggac     900
ggcgtggagg tgcataatgc caagacaaag ccacgggagg agcagttcaa cagcacgttc     960
cgtgtggtca gcgtcctcac cgttgtgcac caggactggc tgaacggcaa ggagtacaag    1020
tgcaaggtct ccaacaaagg cctcccagcc cccatcgaga aaaccatctc caaaaccaaa    1080
gggcagcccc gagaaccaca ggtgtacacc ctgcccccat cccgggagga gatgaccaag    1140
aaccaggtca gcctgacctg cctggtcaaa ggcttctacc ccagcgacat cgccgtggag    1200
tgggagagca atgggcagcc ggagaacaac tacaagacca cacctcccat gctggactcc    1260
gacggctcct tcttcctcta cagcaagctc accgtggaca gagcaggtg gcagcagggg    1320 aacgtcttct catgctccgt gatgcatgag gctctgcaca accactacac gcagaagagc    1380 ctctcccctgt ctccgggtaa a                                            1401

<210> SEQ ID NO 4
<211> LENGTH: 705
<212> TYPE: DNA
<213> ORGANISM: Homo sapiens

<400> SEQUENCE: 4
atggaaaccc cagcgcagct tctcttcctc ctgctactct ggctcccaga taccaccgga     60
gaaattgtgt tgacgcagtc tccaggcacc ctgtctttgt ctccagggga aagagccacc    120
ctctcctgta gggccagtca gagtgttcgc ggcaggtact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgtt ttactgtcag cagtatggta gttcacctcg acgttcggc    360 caagggacca aggtggaaat caaacgaact gtggctgcac catctgtctt catcttcccg     420
ccatctgatg agcagttgaa atctggaact gcctctgttg tgtgcctgct gaataacttc     480
```

```
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                    705
```

<210> SEQ ID NO 5
<211> LENGTH: 467
<212> TYPE: PRT
<213> ORGANISM: Homo sapiens

<400> SEQUENCE: 5

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335
```

```
Lys Glu Tyr Lys Cys Lys Val Ser Asn Lys Gly Leu Pro Ala Pro Ile
                340                 345                 350

Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 6
<211> LENGTH: 235
<212> TYPE: PRT
<213> ORGANISM: Homo sapiens

<400> SEQUENCE: 6

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Arg Gly Arg Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

```
Pro Val Thr Lys Ser Phe Asn Arg Gly Glu Cys
225                 230                 235
```